(12) United States Patent
Toyoda

(10) Patent No.: US 8,557,998 B2
(45) Date of Patent: Oct. 15, 2013

(54) BENZYLPIPERIZINE COMPOUND

(75) Inventor: Tomohiro Toyoda, Suita (JP)

(73) Assignee: Dainippon Sumitomo Pharma Co., Ltd, Osaka (JP)

( * ) Notice: Subject to any disclaimer, the term of this patent is extended or adjusted under 35 U.S.C. 154(b) by 0 days.

(21) Appl. No.: 13/527,612

(22) Filed: Jun. 20, 2012

(65) Prior Publication Data
US 2012/0259122 A1 Oct. 11, 2012

Related U.S. Application Data

(63) Continuation of application No. 13/010,194, filed on Jan. 20, 2011, now Pat. No. 8,232,405, which is a continuation of application No. 12/597,942, filed as application No. PCT/JP2009/051854 on Feb. 4, 2009, now Pat. No. 8,063,223.

(30) Foreign Application Priority Data

Feb. 5, 2008 (JP) .............................. 2008-025676

(51) Int. Cl.
*C07D 211/22* (2006.01)
(52) U.S. Cl.
USPC .......................................... 546/236; 546/241
(58) Field of Classification Search
USPC ................................................ 546/236, 241
See application file for complete search history.

(56) References Cited

U.S. PATENT DOCUMENTS

| | | | |
|---|---|---|---|
| 4,921,863 A | 5/1990 | Sugimoto et al. | |
| 5,698,553 A | 12/1997 | Prucher et al. | |
| 6,124,323 A | 9/2000 | Bigge et al. | |
| 6,284,774 B1 | 9/2001 | Wright et al. | |
| 6,787,560 B2 * | 9/2004 | Kodo et al. | 514/331 |
| 8,063,223 B2 | 11/2011 | Toyoda et al. | |
| 8,232,405 B2 | 7/2012 | Toyoda et al. | |
| 2003/0191126 A1 | 10/2003 | Kodo et al. | |
| 2005/0065140 A1 | 3/2005 | Kodo et al. | |
| 2007/0219179 A1 | 9/2007 | Suzuki et al. | |

FOREIGN PATENT DOCUMENTS

| | | |
|---|---|---|
| AU | 9671774 | 11/1996 |
| CA | 2188485 A1 | 5/1997 |
| EP | 0934932 A1 | 8/1999 |
| FR | 2672286 A1 | 8/1992 |
| FR | 2696741 A1 | 4/1994 |
| FR | 2697251 A1 | 4/1994 |
| JP | 2000-500773 A | 1/2000 |
| WO | 88/02365 A1 | 4/1988 |
| WO | 97/23216 A1 | 7/1997 |
| WO | 98/08816 A1 | 3/1998 |
| WO | 01/43740 A1 | 6/2001 |
| WO | 02/06231 A1 | 1/2002 |
| WO | 03/053928 A1 | 7/2003 |
| WO | 2004/046124 A1 | 6/2004 |
| WO | 2005/108389 A1 | 11/2005 |

OTHER PUBLICATIONS

Y. Sato et al., "Syntheses and Pharmacology of 1-[2-(2-Hydroxyethoxy)-ethyl]-4-p-chlorobenzylpiperidine Hydrochloride (Piclobetol) and the Related Compounds", Ann. Sankyo Res. Lab., vol. 23, 1971, pp. 104-116.

A.M. Ismaiel et al., "Ketanserin Analogues: The Effect of Structural Modification on 5-HT2 Serotonin Receptor Binding", J. Med. Chem., vol. 38, 1995, pp. 1196-1202.

Klaus Rehse et al., "Neuropsychotrope Aktivitat dopaminanaloger Piperidin- und Piperazinderivate", Arch. Pharm. (Weinheim), vol. 312, 1979, pp. 670-681.

Huang et al.; "Guidance for Industry, Drug Interaction Studies—Study Design, Data Analysis, and Implications for Dosing and Labeling"; Sep. 2006; U.S. Food and Drug Administration, pp. 1-52.

Suaer et al.; "Atomoxetine Hydrochloride: Clinical Drug-Drug Interaction Prediction and Outcome"; The Journal of Pharmacology and Experimental Therapeutics, vol. 308, No. 2, 2004; pp. 410-418.

Testino Jr., et al.; "High-Throughput Inhibition Screening of Major Human Cytochrome P450 Enzymes Using an in Vitro Cocktail and Liquid Chromatography—Tandem Mass Spectrometry"; Journal of Pharmaceutical and Biomedical, 30 (2003), pp. 1459-1467.

(Continued)

*Primary Examiner* — Celia Chang
(74) *Attorney, Agent, or Firm* — Sughrue Mion, PLLC

(57) ABSTRACT

Disclosed is a benzylpiperizine compound represented by formula (1) or a pharmaceutically acceptable salt thereof, which is useful as a medicinal agent such as an antidepressant agent. (In the formula (1), $R^1$ represents a hydrogen atom or a methyl group; $R^2$ is a group bound in a p- or m-position relative to a methylene group and represents a chlorine atom bound in a p-position, a bromine atom bound in a p-position, a methyl group bound in a p-position, a chlorine atom bound in a m-position or a bromine atom bound to in a m-position; X represents a methylene or an oxygen atom; and n represents an integer of 1 to 3.)

3 Claims, 6 Drawing Sheets

(56) References Cited

OTHER PUBLICATIONS

Di et al.; "Comparison of Cytochrome P450 Inhibition Assays for Drug Discovery Using Human Liver Microsomes With LC-MS, rhCYP450 Isozymes With Fluorescence, and Double Cocktail With LC-MS"; International Journal of Pharmaceutics, 335 (2007); pp. 1-11.

B. Agai et al., "Convenient, Benign and Scalable Synthesis of 2- and 4-Substituted Benzylpiperidines", Eur. J. Org. Chem., vol. 17, 2004, pp. 3623-2632.

* cited by examiner

BENZYLPIPERIZINE COMPOUND

CROSS REFERENCE TO RELATED APPLICATIONS

This application is a Continuation Application of U.S. Application No. 13/010,194, filed Jan. 20, 2011, now U.S. Pat. No. 8,232,405 now allowed, which is a Continuation Application of U.S. application Ser. No. 12/597,942, filed Oct. 28, 2009, now U.S. Pat. No. 8,063,223, which is a National Stage of International Application No. PCT/JP2009/051854 filed Feb. 4, 2009, which claims priority from Japanese Patent Application No. 2008-025676 filed Feb. 5, 2008, the contents of all of which are incorporated herein by reference in their entirety.

TECHNICAL FIELD

The present invention relates to a novel benzylpiperidine compound or a pharmaceutically acceptable salt thereof, which is useful as a serotonin reuptake inhibitor. More specifically, the benzylpiperidine compound of the present invention is a compound having a piperidine parent skeleton, and this compound has a particular substituted benzyl group at 4-position of piperidine and further has, at 1-position of piperidine, a phenylethyl (phenethyl) group of which the benzene ring moiety is fused with a saturated ring comprising an oxo group. The benzylpiperidine compound of the present invention has a serotonin reuptake inhibitory effect and is therefore useful as, for example, an antidepressant.

BACKGROUND ART

Depression is a chronic disease that affects people of all ages. Of various antidepressants currently used, the most successful one is a selective serotonin reuptake inhibitor (hereinafter, also abbreviated to SSRI). SSRIs have a higher serotonin reuptake inhibitory effect than dopamine and noradrenalin reuptake inhibitory effects. The first drug put on the market as an SSRI was zimelidine. Examples of other SSRIs subsequently launched or under development include fluoxetine, fluvoxamine, citalopram, sertraline, and paroxetine.

Although such SSRIs are widely used as therapeutic drugs for depression, it has been pointed out that they still have some problems. Typical examples thereof include the following problems: even SSRIs have an insufficient therapeutic effect on refractory depression patients, which occupy approximately ⅓ of all depression patients; and they require a period as long as 3 to 8 weeks for the onset of a sufficient antidepressant effect. Thus, the onset of the antidepressant effects of SSRIs is slow, whereas their side effects may immediately occur. Specifically, SSRIs present the problem of a vulnerable period during which patients undergo only the side effects of the drugs without obtaining their therapeutic effects. Therefore; treating physicians often bear a heavy burden of persuading patients to continuously take the same drugs even during the period. Furthermore, due to the slow onset of the antidepressant effect, patients at risk of attempting suicide restore their initiative before experiencing sufficient improvements in the symptoms of depression. Therefore, for example, they are threatened by suicide or needed to be repeatedly hospitalized. It has thus been demanded to develop an antidepressant with rapid onset of the antidepressant effect.

The reason why SSRIs require a period as long as a few weeks for the onset of an antidepressant effect may be as follows:

SSRIs inhibit acute serotonin reuptake of serotonin turnover. This inhibitory effect occurs in the nerve endings of serotonergic neurons and thereby enhances serotonin-mediated neurotransmission, resulting in the antidepressant effect. However, this inhibitory effect also occurs in cell bodies or dendrites of serotonergic neurons present in raphe nuclei and therefore enhances, in the raphe nuclei, serotonin 1A autoreceptor-mediated suppression (negative feedback reaction) of the spontaneous firing of the serotonergic neurons. As a result, neurotransmission in the serotonergic neurons is less enhanced than expected, as a whole, in the initial stage after SSRI administration. On the other hand, continuous SSRI administration for a few weeks desensitizes the serotonin 1A autoreceptor on cell bodies or dendrites of serotonergic neurons in raphe nuclei and thereby eliminates the negative feedback reaction. As a result, the enhanced activities of the serotonergic neurons in cooperation with serotonin uptake inhibition in the nerve endings successfully enhance serotonin neurotransmission, resulting in a sufficient antidepressant effect.

Thus, reduction in the period required for the onset of SSRI effects or potentiation of the antidepressant effect can be achieved by the combined use with a serotonin 1A receptor antagonist, which blocks the serotonin 1A autoreceptor and thereby eliminates the negative feedback reaction of serotonin, or by the combined use with a serotonin 1A receptor agonist, which actively stimulates the serotonin 1A autoreceptor to reduce a period required for desensitization. In actuality, it has been reported that the combined use of SSRI with pindolol having high affinity for serotonin 1A receptors potentiates the effect of the serotonin reuptake inhibitor on depression patients and reduces a period required for the onset of the effect (Arch, Gen. Psychiatry, (1994), 51, 248-251).

When patients take drugs, it is preferred that the drugs be fewer in number or type. Thus, based on the above findings, a compound having a serotonin reuptake inhibitory effect in combination with affinity for serotonin 1A receptors can probably be used as a novel antidepressant by itself without being combined with other drugs, and this novel antidepressant has a strong antidepressant effect and requires a reduced period for the onset of the effect. It has thus been desired to develop such a compound as a drug.

A previously reported compound having a serotonin reuptake inhibitory effect in combination with affinity for serotonin 1A receptors is a benzylpiperidine derivative having a substituted benzyl group at 4-position and a substituted phenylethyl group at 1-position (see e.g., PATENT DOCUMENT 1). Specifically, the document discloses serotonin reuptake inhibitors comprising, as an active ingredient, a cyclic amine or the like represented by the formula (A):

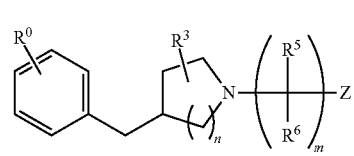

(A)

wherein each of plural $R^0$ present independently represents a hydrogen atom, a halogen atom, an alkyl group, a substituted alkoxy group, or the like; $R^3$ represents a hydrogen atom or the like; n represents an integer of 2 or the like; m represents an integer of 2 or the like; $R^5$ and $R^6$ each independently represent a hydrogen atom or the like; and Z represents a substituted aryl group or the like.

The document further discloses that these serotonin reuptake inhibitors have serotonin 1A antagonistic activity.

On the other hand, a compound having a substituted benzyl group at 4-position of piperidine has been reported in plural documents. Examples thereof include a document that discloses cyclic amine derivatives acting as therapeutic drugs for cerebral vascular disorders (see PATENT DOCUMENT 2) and a document that discloses 4-substituted piperidines acting as NMDA receptor antagonists (see PATENT DOCUMENT 3).

Furthermore, a compound having a substituted phenylethyl group at 1-position of piperidine has also been reported in several documents. Indole derivatives having a piperidine ring having a cyclic ketone structure as a substituent on a phenylethyl group have been reported as 5-HT1A antagonists (see e.g., PATENT DOCUMENT 4). These indole derivatives have structural difference from the benzylpiperidine compounds having a substituted benzyl group at 4-position of piperidine. Moreover, it has not been reported that these indole derivatives also have a serotonin reuptake inhibitory effect.

None of these patent documents specifically disclose or suggest a benzylpiperidine compound that has a substituted benzyl group at 4-position of piperidine and further has, at 1-position of piperidine, a phenylethyl (phenethyl) group of which the benzene ring moiety is fused with a saturated ring comprising an oxo group.

Moreover, many antidepressants such as tricyclic antidepressants (TCAs) and SSRIs are known to have a strong inhibitory effect on the enzyme CYP2D6, one of the molecular species of human cytochrome P450, which participates in drug metabolism. On the other hand, it is also known that many therapeutic agents for psychiatric disorders that may be used in combination with TCA or SSRI in the treatment of depression or anxiety symptoms are metabolized by CYP2D6. Thus, in the combined use of these drugs, the CYP2D6 inhibitory effect of one of the drugs inhibits the metabolism of the other drug. The concentration of the latter drug in blood is increased accordingly, resulting in the possible severe side effects. Thus, an antidepressant having a weaker CYP2D6 inhibitory effect has a smaller drug interaction with a therapeutic agent for psychiatric disorders metabolized by CYP2D6 in the combined use. Therefore, such an antidepressant can be expected to serve as a highly safe drug. It has thus been demanded to develop the drug.

Furthermore, CYP2D6 is known to vary largely in enzyme activity among individuals due to genetic polymorphisms. Drugs metabolized at high rates by CYP2D6 vary largely in in-vivo drug concentration among individuals. Their drug concentrations in blood are highly possibly increased more largely in a poor metabolizer (PM) than in an extensive metabolizer (EM). Moreover, such drugs possibly exhibit a stronger drug interaction with a drug that inhibits CYP2D6 or is metabolized by CYP2D6. Thus, a lower rate of CYP2D6 contribution to drug metabolism offers a smaller pharmacokinetic influence by the genetic polymorphisms of CYP2D6. Therefore, such a drug can be expected to be highly safe. It has also been demanded to develop the drug.
PATENT DOCUMENT 1: U.S. Pat. No. 6,787,560
PATENT DOCUMENT 2: WO88/02365
PATENT DOCUMENT 3: WO97/23216
PATENT DOCUMENT 4: WO2005/108389

DISCLOSURE OF THE INVENTION

Problems to be Solved by the Invention

An object of the present invention is to provide a novel serotonin reuptake inhibitor also having affinity for serotonin 1A receptors. Such a serotonin reuptake inhibitor is expected to serve as a therapeutic drug for, for example, depression or anxiety (anxiety disorder). Thus, an object of the present invention is to provide a more highly safe drug excellent in therapeutic effect. Specifically, an object of the present invention is to provide a drug that has an improved human serotonin reuptake inhibitory activity in combination with affinity for serotonin 1A receptors, has a weaker inhibitory effect on CYP2D6, one of the molecular species of human cytochrome P450, and undergoes small CYP2D6 contribution to drug metabolism in humans.

Means for Solving the Problems

The present inventors have conducted diligent studies to attain the object and consequently found that a benzylpiperidine compound or a pharmaceutically acceptable salt thereof characterized in terms of a chemical structure by having a di-substituted benzyl group having a 2-methoxyethoxy or 2-hydroxyethoxy group at 3-position of the benzene ring moiety and having, at 1-position of piperidine, a phenylethyl group of which the benzene ring moiety is fused with a saturated ring comprising an oxo group, not only has a high human serotonin reuptake inhibitory effect in combination with binding affinity for human 5-HT1A receptors, but also has weaker CYP2D6 inhibition and undergoes small CYP2D6 contribution to metabolism. Based on these findings, the present invention has been completed.

The present invention relates to a benzylpiperidine compound or a pharmaceutically acceptable salt thereof represented by the following [1] to [8], which is useful as a serotonin reuptake inhibitor. Specifically, the present invention relates to:

[1] a compound represented by the formula (1) or a pharmaceutically acceptable salt thereof:

[Formula 2]

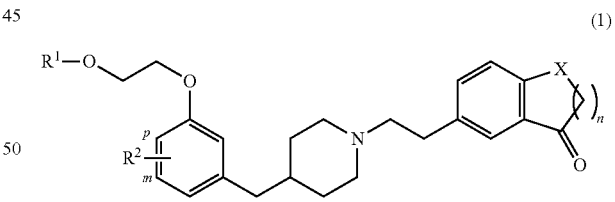

wherein $R^1$ represents a hydrogen atom or a methyl group; $R^2$ represents a group bonded at a p- or m-position in relation to a methylene group bonded to the piperidine ring, specifically, a chlorine atom bonded at the p-position, a bromine atom bonded at the p-position, a methyl group bonded at the p-position, a chlorine atom bonded at the m-position, or a bromine atom bonded at the m-position; X represents a methylene group or an oxygen atom; and n represents an integer of 1 to 3;

[2] the compound according to [1] or a pharmaceutically acceptable salt thereof, wherein X represents a methylene group and n represents an integer of 1 or 2, or wherein X represents an oxygen atom and n represents an integer of 2 or 3;

[3] the compound according to [1] or [2] or a pharmaceutically acceptable salt thereof, wherein R¹ represents a methyl group;

[4] the compound according to any of [1] to [3] or a pharmaceutically acceptable salt thereof, wherein R² represents a bromine atom bonded at the p-position;

[5] the compound according to any of [1] to [4] or a pharmaceutically acceptable salt thereof, wherein X represents an oxygen atom and n represents the integer 2;

[6] the compound according to [1] or [2] or a pharmaceutically acceptable salt thereof, wherein represents a bromine atom bonded at the p-position; X represents an oxygen atom; and n represents the integer 2;

[7] the compound according to [1] or a pharmaceutically acceptable salt thereof, wherein the compound represented by the formula (1) is selected from the group consisting of the following compounds (01) to (15):

(01) 6-(2-{4-[4-Bromo-3-(2-hydroxyethoxy)benzyl]piperidin-1-yl}ethyl)-2,3-dihydro-1H-inden-1-one,
(02) 7-(2-{4-[4-Bromo-3-(2-hydroxyethoxy)benzyl]piperidin-1-yl}ethyl)-3,4-dihydronaphthalen-1(2H)-one,
(03) 6-(2-{4-[4-Bromo-3-(2-hydroxyethoxy)benzyl]piperidin-1-yl}ethyl)-2,3-dihydro-4H-chromen-4-one,
(04) 7-(2-{4-[4-Bromo-3-(2-hydroxyethoxy)benzyl]piperidin-1-yl}ethyl)-3,4-dihydro-1-benzoxepin-5(2H)-one,
(05) 6-(2-{4-[4-Chloro-3-(2-methoxyethoxy)benzyl]piperidin-1-yl}ethyl)-2,3-dihydro-4H-chromen-4-one,
(06) 6-(2-{4-[4-Bromo-3-(2-methoxyethoxy)benzyl]piperidin-1-yl}ethyl)-2,3-dihydro-1H-inden-1-one,
(07) 7-(2-{4-[4-Bromo-3-(2-methoxyethoxy)benzyl]piperidin-1-yl}ethyl)-3,4-dihydronaphthalen-1(2H)-one,
(08) 6-(2-{4-[4-Bromo-3-(2-methoxyethoxy)benzyl]piperidin-1-yl}ethyl)-2,3-dihydro-4H-chromen-4-one,
(09) 7-(2-{4-[4-Bromo-3-(2-methoxyethoxy)benzyl]piperidin-1-yl}ethyl)-3,4-dihydro-1-benzoxepin-5(2H)-one,
(10) 6-(2-{4-[3-(2-Methoxyethoxy)-4-methylbenzyl]piperidin-1-yl}ethyl)-2,3-dihydro-4H-chromen-4-one,
(11) 6-(2-{4-[3-Chloro-5-(2-methoxyethoxy)benzyl]piperidin-1-yl}ethyl)-2,3-dihydro-4H-chromen-4-one,
(12) 6-(2-{4-[3-Bromo-5-(2-methoxyethoxy)benzyl]piperidin-1-yl}ethyl)-2,3-dihydro-1H-inden-1-one,
(13) 7-(2-{4-[3-Bromo-5-(2-methoxyethoxy)benzyl]piperidin-1-yl}ethyl)-3,4-dihydronaphthalen-1(2H)-one,
(14) 6-(2-{4-[3-Bromo-5-(2-methoxyethoxy)benzyl]piperidin-1-yl}ethyl)-2,3-dihydro-4H-chromen-4-one, and
(15) 7-(2-{4-[3-Bromo-5-(2-methoxyethoxy)benzyl]piperidin-1-yl}ethyl)-3,4-dihydro-1-benzoxepin-5(2H)-one; and

[8] A pharmaceutically acceptable salt of a compound according to any of [1] to [7], wherein the pharmaceutically acceptable salt is hydrochloride, hydrobromide, fumarate, benzenesulfonate; or succinate.

Moreover, the present invention relates to a pharmaceutical composition or a therapeutic or preventive drug represented by the following [9] to [12]. Specifically, the present invention relates to:

[9] a pharmaceutical composition comprising a compound according to any of [1] to [7] or a pharmaceutically acceptable salt thereof as an active ingredient;

[10] a serotonin reuptake inhibitor comprising a compound according to any of [1] to [7] or a pharmaceutically acceptable salt thereof as an active ingredient;

[11] an antidepressant or an anxiolytic drug comprising a compound according to any of [1] to [7] or a pharmaceutically acceptable salt thereof as an active ingredient; and

[12] an antidepressant comprising a compound according to any of [1] to [7] or a pharmaceutically acceptable salt thereof as an active ingredient.

Moreover, the present invention relates to an intermediate represented by the following [13] of the benzylpiperidine compound of the present invention according to any of [1] to [7]. Specifically, the present invention relates to:

[13] a compound represented by the formula (11):

[Formula 3]

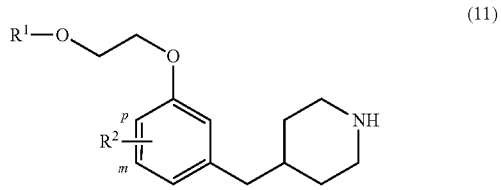

wherein R¹ represents a hydrogen atom or a methyl group; and R² represents a group bonded at a p- or m-position in relation to a methylene group bonded to the piperidine ring, specifically, a chlorine atom bonded at the p-position, a bromine atom bonded at the p-position, a methyl group bonded at the p-position, a chlorine atom bonded at the m-position, or a bromine atom bonded at the m-position.

Moreover, the present invention relates to an intermediate represented by the following [14] of the benzylpiperidine compound of the present invention according to any of [1] to [7]. Specifically, the present invention relates to:

[14] a compound represented by the formula (12):

[Formula 4]

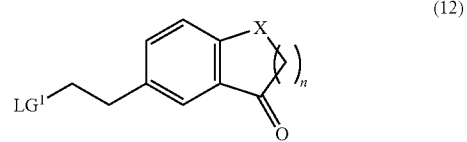

wherein X represents a methylene group or an oxygen atom; n represents an integer of 1 to 3; and LG¹ represents an iodine atom, a bromine atom, a chlorine atom, or a substituted sulfonyloxy group.

Advantages of the Invention

The present invention can provide a benzylpiperidine compound or a pharmaceutically acceptable salt thereof, which is useful as a serotonin reuptake inhibitor that can be used as a therapeutic drug for depression or the like. Specifically, the present invention can provide a benzylpiperidine compound or a pharmaceutically acceptable salt thereof, which has a high human serotonin reuptake inhibitory activity in combination with binding affinity for human 5-HT1A receptors, has weaker CYP2D6 inhibition, and undergoes small CYP2D6 contribution to metabolism.

BEST MODE FOR CARRYING OUT THE INVENTION

Hereinafter, the present invention will be described more specifically.

A benzylpiperidine compound of the present invention represented by the formula (1) is characterized in terms of a chemical structure by having a di-substituted benzyl group having a 2-methoxyethoxy or 2-hydroxyethoxy group at 3-position of the benzene ring moiety and having, at 1-position of piperidine, a phenylethyl group of which the benzene ring moiety is fused with a saturated ring comprising an oxo group.

In the present invention, the term "substituted sulfonyloxy group" means a sulfonyloxy group substituted by an alkyl group or an optionally substituted phenyl group. In this context, examples of the alkyl group include linear or branched alkyl groups having 1 to 6 carbon atoms and specifically include methyl, ethyl, propyl, isopropyl, butyl, isobutyl, sec-butyl, tert-butyl, pentyl, hexyl, and trifluoromethyl groups. Examples of the substituent for the optionally substituted phenyl group include halogen atoms (in this context, examples of the halogen atoms include fluorine, chlorine, bromine, and iodine atoms), alkyl groups (in this context, the alkyl groups refer to linear or branched alkyl groups having 1 to 6 carbon atoms, and examples thereof specifically include methyl, ethyl, propyl, isopropyl, butyl, isobutyl, sec-butyl, tert-butyl, pentyl, and hexyl groups), a trifluoromethyl group, a cyano group, a nitro group, and alkoxy groups (in this context, the alkoxy groups refer to linear or branched alkoxy groups having 1 to 6 carbon atoms, and examples thereof specifically include methoxy, ethoxy, propoxy, isopropoxy, butoxy, isobutoxy, sec-butoxy, tert-butoxy, pentyloxy, and hexyloxy groups). Preferable examples of the substituted sulfonyloxy group include methanesulfonyloxy, benzenesulfonyloxy, and p-toluenesulfonyloxy groups. More preferable examples of the substituted sulfonyloxy group include benzenesulfonyloxy and p-toluenesulfonyloxy groups.

In the formula (1), preferable examples of $R^1$ include a methyl group.

In the formula (1), $R^2$ represents a group bonded at a p- or m-position in relation to a methylene group bonded to the piperidine ring, specifically, a chlorine atom bonded at the p-position, a bromine atom bonded at the p-position, a methyl group bonded at the p-position, a chlorine atom bonded at the m-position, or a bromine atom bonded at the m-position. For example, when $R^2$ represents a chlorine atom bonded at the p-position, a bromine atom bonded at the p-position, or a methyl group bonded at the p-position, the compound of the formula (1) represents a compound represented by the formula (1-p):

[Formula 5]

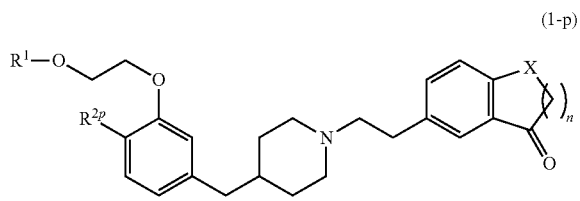

(1-p)

wherein $R^1$, X, and n are as defined above; and $R^{2p}$ represents a chlorine atom, a bromine atom, or a methyl group.

On the other hand, when $R^2$ represents a chlorine atom bonded at the m-position or a bromine atom bonded at the m-position, the compound of the formula (1) represents a compound represented by the formula (1-m):

[Formula 6]

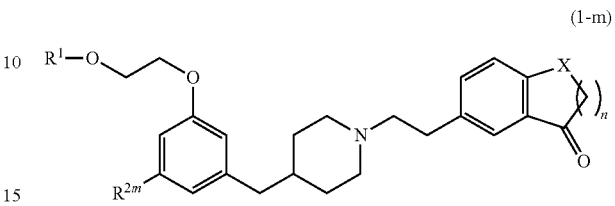

(1-m)

wherein $R^1$, X, and n are as defined above; and $R^{2m}$ represents a chlorine atom or a bromine atom. In the formula (1), preferable examples of $R^2$ include a bromine atom bonded at the p-position. Specifically, a compound represented by the formula (1-p-Br) is preferable:

[Formula 7]

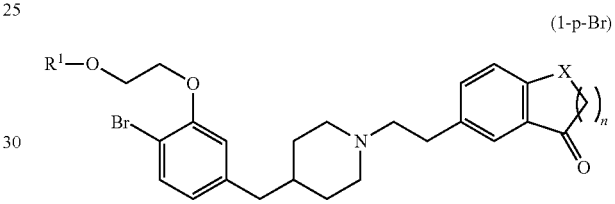

(1-p-Br)

wherein $R^1$, X, and n are as defined above.

The compound of the formula (1) wherein X represents a methylene group and n represents the integer 1 represents a compound represented by the formula (1-C-1):

[Formula 8]

(1-C-1)

wherein $R^1$ and $R^2$ are as defined above.

The compound of the formula (1) wherein X represents a methylene group and n represents the integer 2 represents a compound represented by the formula (1-C-2):

[Formula 9]

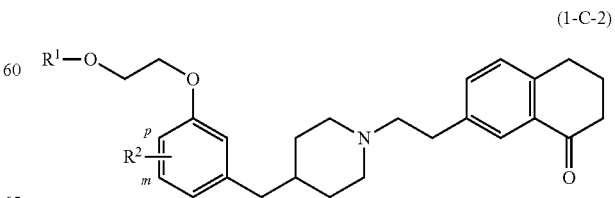

(1-C-2)

wherein $R^1$ and $R^2$ are as defined above.

The compound of the formula (1) wherein X represents a methylene group and n represents the integer 3 represents a compound represented by the formula (1-C-3):

[Formula 10]

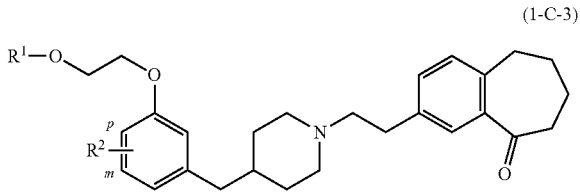

(1-C-3)

wherein R¹ and R² are as defined above.

The compound of the formula (1) wherein X represents an oxygen atom and n represents the integer 1 represents a compound represented by the formula (1-O-1):

[Formula 11]

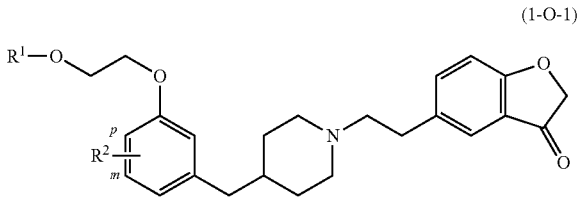

(1-O-1)

wherein R¹ and R² are as defined above.

The compound of the formula (1) wherein X represents an oxygen atom and n represents the integer 2 represents a compound represented by the formula (1-O-2):

[Formula 12]

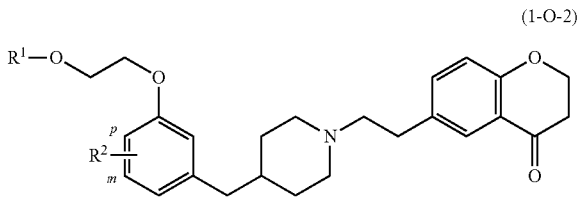

(1-O-2)

wherein R¹ and R² are as defined above.

The compound of the formula (1) wherein X represents an oxygen atom and n represents the integer 3 represents a compound represented by the formula (1-O-3):

[Formula 13]

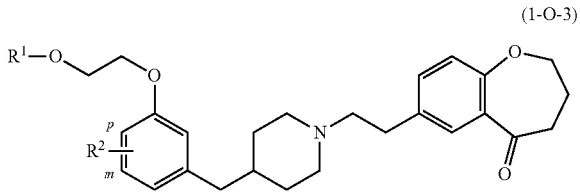

(1-O-3)

wherein R¹ and R² are as defined above.

In the formula (1), the combination of X and n is preferably a combination wherein X represents methylene and n represents an integer of 1 or 2, or wherein X represents an oxygen atom and n represents an integer of 2 or 3. Specifically, the compound represented by the formula (1-C-1), (1-C-2), (1-O-2), or (1-O-3) is preferable. More preferable examples of the combination of X and n include a combination wherein X represents an oxygen atom and n represents the integer 2. Specifically, the compound represented by the formula (1-O-2) is more preferable.

More specifically, the following compounds (01) to (15) are preferable:

(01) 6-(2-{4-[4-Bromo-3-(2-hydroxyethoxy)benzyl]piperidin-1-yl}ethyl)-2,3-dihydro-1H-inden-1-one,
(02) 7-(2-{4-[4-Bromo-3-(2-hydroxyethoxy)benzyl]piperidin-1-yl}ethyl)-3,4-dihydronaphthalen-1(2H)-one,
(03) 6-(2-{4-[4-Bromo-3-(2-hydroxyethoxy)benzyl]piperidin-1-yl}ethyl)-2,3-dihydro-4H-chromen-4-one,
(04) 7-(2-{4-[4-Bromo-3-(2-hydroxyethoxy)benzyl]piperidin-1-yl}ethyl)-3,4-dihydro-1-benzoxepin-5(2H)-one,
(05) 6-(2-{4-[4-Chloro-3-(2-methoxyethoxy)benzyl]piperidin-1-yl}ethyl)-2,3-dihydro-4H-chromen-4-one,
(06) 6-(2-{4-[4-Bromo-3-(2-methoxyethoxy)benzyl]piperidin-1-yl}ethyl)-2,3-dihydro-1H-inden-1-one,
(07) 7-(2-{4-[(4-Bromo-3-(2-methoxyethoxy)benzyl]piperidin-1-yl}ethyl)-3,4-dihydronaphthalen-1(2H)-one,
(08) 6-(2-{4-[4-Bromo-3-(2-methoxyethoxy)benzyl]piperidin-1-yl}ethyl)-2,3-dihydro-4H-chromen-4-one,
(09) 7-(2-{4-[4-Bromo-3-(2-methoxyethoxy)benzyl]piperidin-1-yl}ethyl)-3,4-dihydro-1-benzoxepin-5(2H)-one,
(10) 6-(2-{4-[3-(2-Methoxyethoxy)-4-methylbenzyl]piperidin-1-yl}ethyl)-2,3-dihydro-4H-chromen-4-one,
(11) 6-(2-{4-[3-Chloro-5-(2-methoxyethoxy)benzyl]piperidin-1-yl}ethyl)-2,3-dihydro-4H-chromen-4-one,
(12) 6-(2-{4-[3-Bromo-5-(2-methoxyethoxy)benzyl]piperidin-1-yl}ethyl)-2,3-dihydro-1H-inden-1-one,
(13) 7-(2-{4-[3-Bromo-5-(2-methoxyethoxy)benzyl]piperidin-1-yl}ethyl)-3,4-dihydronaphthalen-1(2H)-one,
(14) 6-(2-{4-[3-Bromo-5-(2-methoxyethoxy)benzyl]piperidin-1-yl}ethyl)-2,3-dihydro-4H-chromen-4-one, and
(15) 7-(2-{4-[3-Bromo-5-(2-methoxyethoxy)benzyl]piperidin-1-yl}ethyl)-3,4-dihydro-1-benzoxepin-5(2H)-one.

The benzylpiperidine compound of the present invention can be produced from compounds known in the art according to methods shown in Production Methods 1 to 5 below, similar methods thereto, or appropriate combinations of synthetic methods well known by those skilled in the art. Some of starting compounds (11), (12), (13), (15), (18), and (19) are novel compounds, which can however be produced according to methods described later in Examples, similar methods thereto, or appropriate combinations of synthetic methods well known by those skilled in the art.

Moreover, in the present specification, the following abbreviations may be used for simplifying the description:

Boc: tert-butoxycarbonyl group,
Piv: tert-butylcarbonyl group,
Me: methyl group,
Et: ethyl group,
Ph: phenyl group,
Bn: benzyl group,
Ms: methanesulfonyl group,
Bs: benzenesulfonyl group,
Ts: p-toluenesulfonyl group,
p: para (e.g., the abbreviation "p-Br" means a bromine atom bonded at a para-position),
m: meta (e.g., the abbreviation "m-Br" means a bromine atom bonded at a meta-position), and
DMSO: dimethyl sulfoxide.

Production Method 1: Production Method for Compound (1)

The compound represented by the formula (1) or a salt thereof can be produced, for example, by the following method:

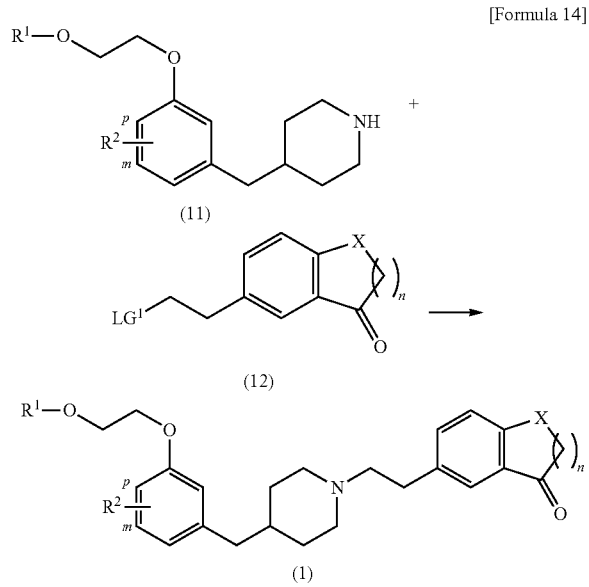

herein $R^1$, $R^2$, X, n and $LG^1$ are as defined above.

The compound (1) of interest or the salt thereof can be obtained by reacting a compound (11) or a salt thereof with a compound (12). The reaction can be carried out in an appropriate inert solvent for 10 minutes to 48 hours in a temperature range of approximately −20° C. to the boiling point of the solvent used, if necessary in the presence of a base and if necessary in the presence of a phase transfer catalyst.

Examples of the base include: organic bases such as triethylamine, diisopropylethylamine, and pyridine; inorganic bases such as potassium carbonate, sodium carbonate, cesium carbonate, potassium bicarbonate, sodium bicarbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and metal alkoxides such as sodium methoxide and potassium tert-butoxide. Preferable examples thereof include potassium carbonate and dipotassium hydrogen phosphate.

Examples of the phase transfer catalyst include tetrabutylammonium hydrogen sulfate.

Examples of the inert solvent include: halogenated hydrocarbons such as chloroform and dichloromethane; aromatic hydrocarbons such as benzene and toluene; ether solvents such as diethyl ether, tetrahydrofuran (THF), and 1,4-dioxane; lower alcohols such as methanol, ethanol, and 2-propanol; aprotic polar solvents such as acetonitrile, acetone, methyl ethyl ketone, dimethylformamide, N-methyl-2-pyrrolidinone, and dimethyl sulfoxide; and mixed solvents thereof. More preferable examples of the solvent include acetonitrile, toluene, dimethylformamide, and N-methyl-2-pyrrolidinone, and mixed solvents thereof.

The leaving group $LG^1$ is preferably a bromine or substituted sulfonyloxy group, more preferably a benzenesulfonyloxy or p-toluenesulfonyloxy group.

Production Method 2: Production Method for Compound (11)

The compound (11) or the salt thereof used as a starting material in Production Method 1 can be produced, for example, by the following method with reference to a document such as U.S. Pat. No. 6,787,560:

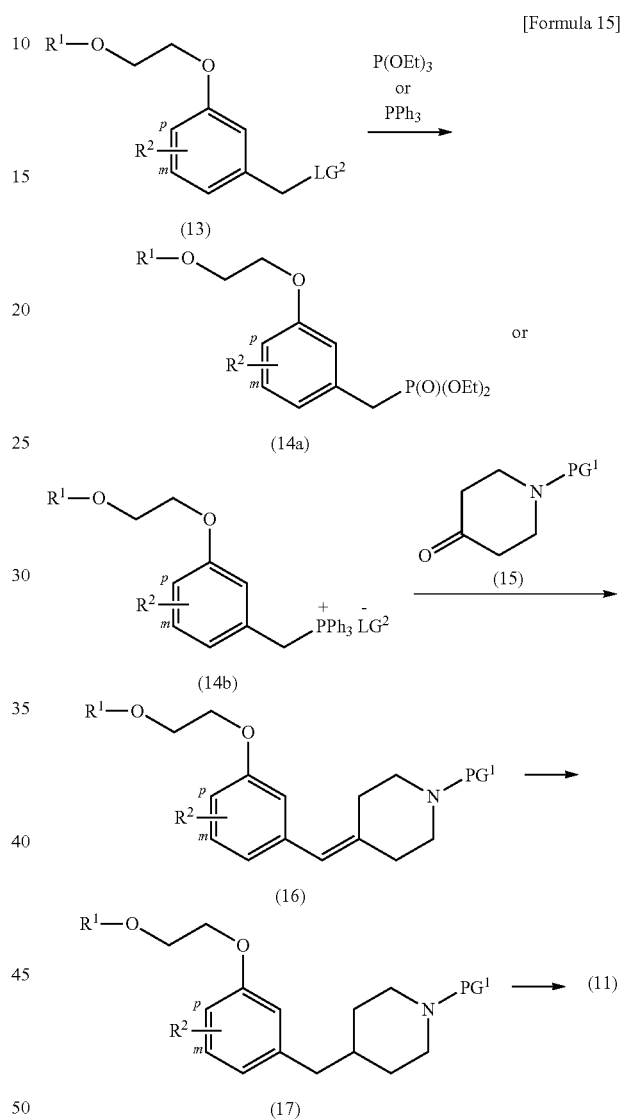

wherein $R^1$ and $R^2$ are as defined above; $PG^1$ represents a protecting group for the nitrogen atom; and $LG^2$ represents a leaving group, wherein examples of the protecting group $PG^1$ for the nitrogen atom include alkyloxycarbonyl groups such as t-butyloxycarbonyl and 9-fluorenylmethyloxycarbonyl groups, and examples of the leaving group $LG^2$ include halogen atoms such as chlorine, bromine, and iodine atoms and substituted sulfonyloxy groups such as p-toluenesulfonyloxy and methanesulfonyloxy groups.

A compound (13) is converted to a phosphonic acid ester (14a) or a phosphonium salt (14b). This conversion to the phosphonic acid ester (14a) can be carried out by reacting triethyl phosphite in the absence of a solvent or in an inert solvent for 1 hour to 3 days at a temperature between an ice-cold temperature and the boiling point of the solvent used or triethyl phosphite. Alternatively, the conversion to the phosphonium salt (14b) can be carried out by reacting triphenylphosphine in an inert solvent for 1 hour to 3 days at a temperature between an ice-cold temperature and the boiling point of the solvent used.

This phosphonic acid ester (14a) or phosphonium salt (14b) can be converted to a compound (16) through reaction with ketone (15) in the presence of a base in an appropriate inert solvent for 10 minutes to 48 hours at a temperature of approximately −20° C. to the boiling point of the solvent used.

Examples of the base include: organic bases such as triethylamine and pyridine; inorganic bases such as potassium carbonate, sodium carbonate, potassium hydroxide, sodium hydroxide, and sodium hydride; and metal alkoxides such as sodium methoxide and potassium tert-butoxide.

Examples of the inert solvent include: halogenated hydrocarbons such as chloroform and dichloromethane; aromatic hydrocarbons such as benzene and toluene; ether solvents such as diethyl ether, tetrahydrofuran, 1,4-dioxane, and 1,2-dimethoxyethane; lower alcohols such as methanol, ethanol, and 2-propanol; aprotic polar solvents such as acetonitrile, dimethylformamide, N-methyl-2-pyrrolidinone, and dimethyl sulfoxide; and mixed solvents thereof.

The compound (16) can be converted to a compound (17) through catalytic hydrogenation. This hydrogenation for the compound wherein $R^2$ represents a bromine atom bonded at the p-position or a bromine atom bonded at the m-position can be carried out by reacting the compound at 0° C. to 50° C. in an appropriate inert solvent at an ambient or pressurized hydrogen atmosphere over a catalyst such as rhodium catalysts (e.g., rhodium carbon), platinum catalysts (e.g., platinum carbon and platinum oxide), ruthenium catalysts (e.g., ruthenium carbon), and palladium chloride. Examples of the appropriate inert solvent include: ethyl acetate; aromatic hydrocarbons such as benzene and toluene; ether solvents such as diethyl ether, tetrahydrofuran, 1,4-dioxane, and 1,2-dimethoxyethane; lower alcohols such as methanol, ethanol, and 2-propanol; aprotic polar solvents such as dimethylformamide, N-methyl-2-pyrrolidinone, and dimethyl sulfoxide; and mixed solvents thereof. More preferable examples of the catalyst include rhodium carbon and platinum carbon. Moreover, in this case, more preferable examples of the solvent include ethyl acetate.

The compound (17) can be deprotected by a conventional method to obtain the compound (11) of interest. When the protecting group is a t-butyloxycarbonyl group, the deprotection is carried out by treating the compound (17) with an inorganic acid (e.g., hydrochloric acid or sulfuric acid) or an organic acid (e.g., trifluoroacetic acid) in an appropriate inert solvent at a temperature between −20° C. and the boiling point of the solvent used. Examples of the inert solvent include: halogenated hydrocarbons such as chloroform and dichloromethane; aromatic hydrocarbons such as benzene and toluene; ether solvents such as diethyl ether, tetrahydrofuran, 1,4-dioxane, and 1,2-dimethoxyethane; lower alcohols such as methanol, ethanol, and 2-propanol; aprotic polar solvents such as acetonitrile, dimethylformamide, N-methyl-2-pyrrolidinone, and dimethyl sulfoxide; and mixed solvents thereof. When the protecting group is a 9-fluorenylmethyloxycarbonyl group, the deprotection is carried out by treating the compound (17) with an organic base (e.g., pyrrolidine, piperidine, morpholine, triethylamine, or diisopropylethylamine) in an appropriate inert solvent at a temperature between −20° C. and the boiling point of the solvent used. Examples of the inert solvent include: halogenated hydrocarbons such as chloroform and dichloromethane; aromatic hydrocarbons such as benzene and toluene; ether solvents such as diethyl ether, tetrahydrofuran, 1,4-dioxane, and 1,2-dimethoxyethane; lower alcohols such as methanol, ethanol, and 2-propanol; aprotic polar solvents such as acetonitrile, dimethylformamide, N-methyl-2-pyrrolidinone, and dimethyl sulfoxide; and mixed solvents thereof.

Production Method 3: Production Method for Compound (12)

The compound (12) used as a starting material in Production Method 1 can be produced, for example, by the following method:

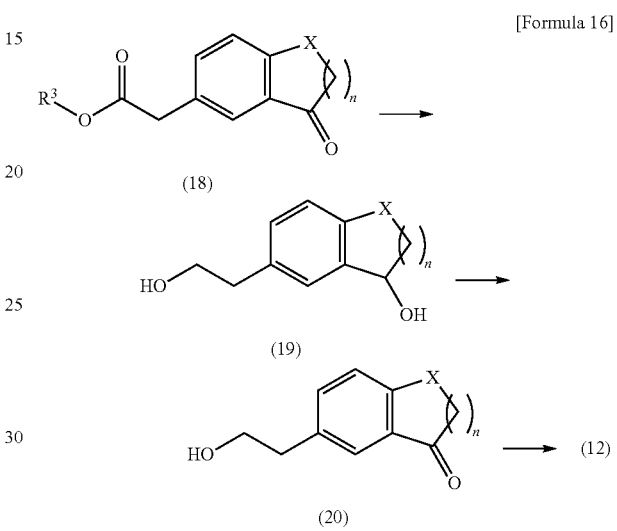

[Formula 16]

wherein X and n are as defined above; and $R^3$ represents a hydrogen atom or an alkyl group, wherein examples of the alkyl group include linear or branched alkyl groups having 1 to 6 carbon atoms and can specifically include methyl, ethyl, propyl, isopropyl, butyl, isobutyl, sec-butyl, tert-butyl, pentyl, isopentyl, neopentyl, tert-pentyl, 1-methylbutyl, and hexyl groups.

A compound (18) can be reacted with an appropriate reducing agent (e.g., lithium aluminum hydride, lithium borohydride, sodium borohydride, or diborane) for 10 minutes to 48 hours in an appropriate inert solvent (e.g., ether solvents such as diethyl ether, tetrahydrofuran (THF), and 1,4-dioxane) at a temperature between −20° C. and the boiling point of the solvent used to obtain a compound (19).

The compound (19) can be oxidized with an oxidizing agent (e.g., manganese dioxide) in an appropriate inert solvent to obtain a compound (20). Examples of the appropriate inert solvent include halogenated solvents such as chloroform and dichloromethane; ether solvents such as acetonitrile, diethyl ether, tetrahydrofuran, 1,4-dioxane, and 1,2-dimethoxyethane; aprotic polar solvents such as acetonitrile, dimethylformamide, N-methyl-2-pyrrolidone, and dimethyl sulfoxide; and mixed solvents thereof.

The hydroxyl group of the compound (20) can be converted by a conventional method to a halogen atom (e.g., a chlorine, bromine, or iodine atom) or a substituted sulfonyloxy group (e.g., a p-toluenesulfonyloxy, benzenesulfonyloxy, or methanesulfonyloxy group) to obtain the compound (12). Specifically, the compound (12) can be obtained by reacting the compound (20) with, for example, methanesulfonyl chloride, benzenesulfonyl chloride, or p-toluenesulfonyl chloride for 10 minutes to 48 hours in the presence of a base in an inert solvent at a temperature between −20° C. and the boiling point of the solvent used. Examples of the appropriate inert solvent include: halogenated solvents such as chloroform and dichloromethane; ether solvents such as diethyl ether, tetrahydrofuran, 1,4-dioxane, and 1,2-dimethoxyethane; aprotic polar solvents such as acetonitrile, dimethylformamide, N-methyl-2-pyrrolidone, and dimethyl sulfoxide; and mixed solvents thereof. Examples of the appropriate base include: organic bases such as triethylamine and pyridine; and inorganic bases such as potassium carbonate and sodium hydroxide. Moreover, the compound (12) wherein $LG^1$ is halogen (e.g., a chlorine or bromine atom) can be obtained by reacting the compound (12) wherein $LG^1$ is a substituted sulfonyloxy group (e.g., a p-toluenesulfonyloxy or methanesulfonyloxy group) with, for example, lithium bromide for 10 minutes to 48 hours in an inert solvent at a temperature between −20° C. and the boiling point of the solvent used. Examples of the appropriate inert solvent include: halogenated solvents such as chloroform and dichloromethane; ether solvents such as diethyl ether, tetrahydrofuran, 1,4-dioxane, and 1,2-dimethoxyethane; aprotic polar solvents such as acetonitrile, dimethylformamide, N-methyl-2-pyrrolidone, and dimethyl sulfoxide; and mixed solvents thereof. Moreover, in an alternative method, the compound (12) can be obtained, for example, by reacting the compound (20) with carbon tetrachloride or carbon tetrabromide in the presence of triphenylphosphine in an appropriate inert solvent.

Production Method 4: Production Method for Compound (12)

The starting compound (12) can also be produced, for example, by the following method:

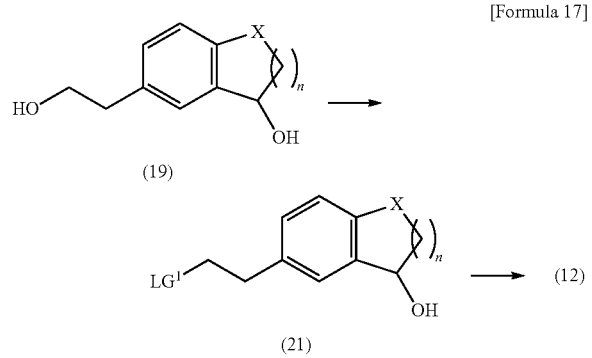

[Formula 17]

wherein X, n, and $LG^1$ are as defined above.

The primary hydroxyl group of the compound (19) can be converted by a conventional method to a substituted sulfonyloxy group (e.g., a p-toluenesulfonyloxy, benzenesulfonyloxy, or methanesulfonyloxy group) to obtain a compound (21). The hydroxyl group of the compound (21) can be oxidized by a conventional method, for example, oxidation with manganese dioxide or dimethyl sulfoxide (DMSO), in an appropriate inert solvent to obtain the compound (12).

Production Method 5: Production Method for Compound (20)

The intermediate compound (20) in Production Method 3 can be produced, for example, by the following method:

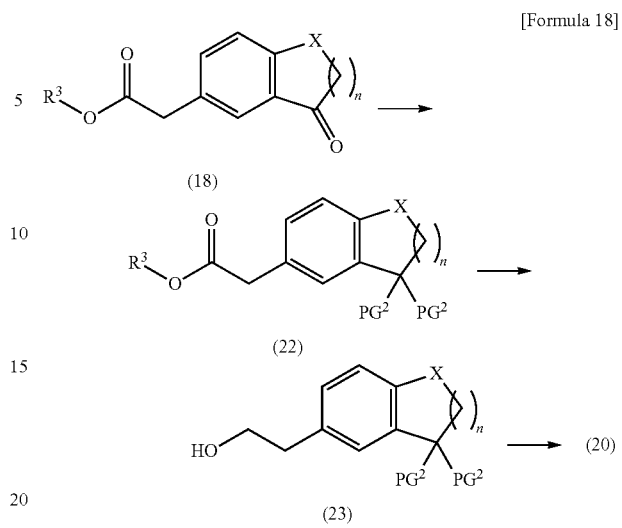

[Formula 18]

wherein $R^3$, X, and n are as defined above; and $PG^2$ represents a methoxy group, a methylthio group, or the like, or two $PG^2$ may together form a ring and represent a cyclic acetal group such as a 1,3-dioxolane or 1,3-dioxane group.

The ketone of the compound (18) is converted by a conventional method to dialkyl acetal or dialkyl thioacetal to obtain a compound (22). This compound is reduced with an appropriate reducing agent (e.g., lithium aluminum hydride, lithium borohydride, sodium borohydride, or diborane) in an appropriate inert solvent to obtain a compound (23). The compound (23) can be deprotected by an appropriate method to obtain the compound (20).

The compound (18) can be synthesized according to a method described in, for example, Journal of Medicinal Chemistry (1994), 37 (21), 3482, Journal of Medicinal Chemistry (1979), 22 (12), 1464, FR Patent No. 2672601, or JP-A-61-236774.

The starting materials and the reagents used in the production methods are commercially available compounds or can be produced from compounds known in the art using methods known in the art, unless otherwise specified. Moreover, functional groups in the compound of the formula (1) may be converted appropriately to obtain another compound of the formula (1). The conversion of functional groups can be carried out according to general methods usually carried out [see e.g., R. C. Larock, Comprehensive Organic Transformations, (1989)].

In the production methods, when any functional group located at a site other than the reaction point is altered under the described reaction conditions or is inappropriate for the described methods, this functional group can be protected with an appropriate protecting group prior to the reaction and then deprotected to obtain the compound of interest. For example, usual protecting groups as described in, for example, T. W. Greene, Protective Groups in Organic Synthesis, John Wiley & Sons Inc., (1981) can be used as the protecting group. Specifically, examples of the protecting group can include: for amines, ethoxycarbonyl, tert-butoxycarbonyl, benzyloxycarbonyl, acetyl, benzoyl, and benzyl; for hydroxyl groups, trialkylsilyl, acetyl, benzoyl, and benzyl; and for ketones, dimethyl acetal, 1,3-dioxane, 1,3-dioxolane, S,S'-dimethyl dithioacetal, 1,3-dithiane, and oxime.

The introduction and deprotection of the protecting group can be carried out according to methods routinely used in synthetic organic chemistry (see e.g., Protective Groups in Organic Synthesis) or methods equivalent thereto.

The intermediates and the compounds of interest in the production methods can be isolated and purified by purification methods routinely used in synthetic organic chemistry, for example, neutralization, filtration, extraction, washing, drying, concentration, recrystallization, and various chromatography techniques. Moreover, the intermediates may be subjected to the subsequent reactions without being particularly purified.

Some of the compounds of the present invention represented by the formula (1) may include tautomers. Examples of the tautomerism include events represented by the formula (24):

[Formula 19]

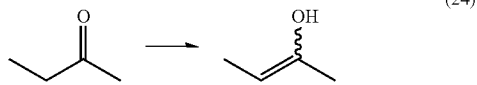

(24)

The present invention encompasses all possible isomers including the tautomers, and mixtures thereof.

The pharmaceutically acceptable salt of the compound represented by the formula (1) is a nontoxic salt routinely used. Examples thereof include: acid addition salts such as organic acid salts (e.g., acetate, propionate, trifluoroacetate, maleate, fumarate, citrate, succinate, tartrate, methanesulfonate, benzenesulfonate, formate, and toluenesulfonate) and inorganic acid salts (e.g., hydrochloride, hydrobromide, hydroiodide, sulfate, nitrate, and phosphate); salts with amino acids (e.g., arginine acid, aspartic acid, and glutamic acid); metal salts such as alkali metal salts (e.g., sodium salts and potassium salts) and alkaline-earth metal salts (e.g., calcium salts and magnesium salts); ammonium salts; and organic base salts such as trimethylamine salts, triethylamine salts, pyridine salts, picoline salts, dicyclohexylamine salts, and N,N'-dibenzylethylenediamine salts.

The pharmaceutically acceptable salt of the compound represented by the formula (1) can be obtained only by directly purifying the compound (1) obtained in the form of a pharmaceutically acceptable salt or by dissolving or suspending the compound (1) obtained in a free from in an appropriate organic solvent and forming a salt by a usual method by the addition of an acid or a base to this solution or suspension. For example, the compound (1) can be mixed with a pharmaceutically acceptable acid or alkali in a solvent such as water, methanol, ethanol, or acetone to form a salt.

Moreover, the compound represented by the formula (1) and the pharmaceutically acceptable salt thereof may be present in the form of hydrates with water or solvates with various solvents such as ethanol. These hydrates and solvates are also encompassed in the present invention.

The obtained crystals of the compound represented by the formula (1) and the pharmaceutically acceptable salt thereof may include crystal polymorphs. These crystal polymorphs are also encompassed in the present invention.

The benzylpiperidine compound of the present invention and the pharmaceutically acceptable salt thereof have a human serotonin reuptake inhibitory effect. Hence, the compound and the salt are useful as therapeutic drugs for diseases mediated by the serotonergic nervous system. Examples of the diseases mediated by the serotonergic nervous system include depression and anxiety. The depression is included in mood disorders in psychiatric disorder classification. The mood disorders are mainly classified into depressive disorders and bipolar disorders. More specifically, examples of the general depression include (i) depressive disorders including major depressive disorder, dysthymic disorder, and depressive disorders not otherwise specified, (ii) depression, and (iii) seasonal affective disorder. The compound and the salt are useful as therapeutic drugs for these diseases or as preventive drugs for relapse thereof. Furthermore, the compound and the salt are also useful as therapeutic drugs for (iv) major depressive episodes in bipolar disorders or as preventive drugs for relapse thereof. On the other hand, the anxiety (anxiety disorder) mainly includes anxiety disorders and phobias. Examples of the anxiety (anxiety disorder) for which the compound and the salt are useful as therapeutic drugs or as preventive drugs for relapse include (v) panic disorder, obsessive compulsive disorder, posttraumatic stress disorder, acute stress disorder, generalized anxiety disorder, and anxiety disorders attributed to general physical diseases, (vi) anxiety disorders including substance-induced anxiety disorder, (vii) agoraphobia, (viii) social phobia, (ix) avoidant personality disorder, and (x) psychosomatic disease. Moreover, the compound and the salt are also useful for depression or anxiety symptoms caused by other diseases (schizophrenia, dementia, etc.). Furthermore, the compound and the salt are also useful for treating or preventing diseases such as: memory disorders including dementia, forgetfulness, and memory disorders associated with aging; eating disorders including anorexia nervosa and bulimia nervosa; obesity; somnipathy; schizophrenia; alcoholism, smoking addiction, nicotine dependence, and drug (narcotic, stimulant drug, psychotropic, etc.) dependence; cluster headache; migraine; pains; Alzheimer's disease; chronic paroxysmal migraine; headache associated with angiopathy; Parkinson's disease including dementia, depression, and anxiety caused by Parkinson's disease, neuroleptic-induced Parkinsonism, and tardive dyskinesia; endocrine abnormality such as hyperprolactinemia; vasospasm (particularly, of the cerebrovascular system); hypertension; kinetic gastrointestinal troubles and gastrointestinal troubles involving a secretion change; and sexual dysfunction including premature ejaculation.

The dose of the benzylpiperidine compound of the present invention or the pharmaceutically acceptable salt thereof differs depending on the age and conditions of a patient. The compound (1) is effective at average one dose of approximately 0.1 mg, 1 mg, 10 mg, 50 mg, 100 mg, 250 mg, 500 mg, or 1000 mg for the diseases such as depression and anxiety. In general, it can be administered to a human at a dose of 0.1 mg/individual to approximately 1,000 mg/individual, preferably 1 mg/individual to approximately 100 mg/individual, per day. Administration is performed once or several times daily. For example, 1, 2, or 3 dose(s) are given each time.

The benzylpiperidine compound of the present invention or the pharmaceutically acceptable salt thereof can be administered orally or parenterally (e.g., intravenously, subcutaneously, intramuscularly, intrathecally, locally, rectally, transdermally, nasally, or pulmonarily) as a pharmaceutical composition used in treatment. Examples of dosage forms for oral administration include dosage forms such as tablets, capsules, pills, granules, fine granules, powders, solutions, syrups, and suspensions. Examples of dosage forms for parenteral administration include preparations in forms such as aqueous injections, non aqueous injections, suppositories, nasal preparations, and transdermal preparations [lotions, emulsion, ointments, creams, jellies, gels, and adhesive skin patches (e.g., tapes, transdermal patch preparations, and poultices), powders for external use, etc.]. These preparations can be prepared using techniques conventionally known in the art and contain a nontoxic and inert carrier or excipient usually used in the pharmaceutical field.

Substances that are routinely used in the pharmaceutical field and are unreactive with the compound represented by the formula (1) or the pharmaceutically acceptable salt thereof are used as pharmaceutical carriers. Specifically, the pharmaceutical composition comprising the compound represented by the formula (1) or the pharmaceutically acceptable salt thereof can contain a pharmaceutical carrier such as excipients, binders, lubricants, stabilizers, disintegrants, buffers, solubilizing agents, tonicity agents, solubilizing agents, pH adjusters, surfactants, emulsifying agents, suspending agents, dispersants, suspension stabilizers, thickeners, viscosity modifiers, gelling agents, soothing agents, preservatives, plasticizers, transdermal absorption promoters, antioxidants, humectants, antiseptics, and flavors. Two or more of these pharmaceutical carrier additives may be selected appropriately for use.

Specific examples of the pharmaceutical carrier additives include lactose, inositol, glucose, sucrose, fructose, mannitol (mannite), dextran, sorbitol (sorbit), cyclodextrin, starch (potato starch, corn starch, amylopectin, etc.), partially pregelatinized starch, saccharose, magnesium aluminometasilicate, synthetic aluminum silicate, sodium alginate, crystalline cellulose, sodium carboxymethylcellulose, hydroxypropyl starch, calcium carboxymethylcellulose, ion-exchanged resins, methylcellulose, gelatin, gum arabic, pullulan, hydroxypropylcellulose, low-substituted hydroxypropylcellulose, hydroxypropylmethylcellulose, carboxymethylcellulose, hydroxyethylcellulose, polyvinylpyrrolidone, polyvinyl alcohol, gelatin, alginic acid, sodium alginate, light anhydrous silicic acid, magnesium stearate, calcium stearate, aluminum stearate, cetostearyl alcohol, wax, paraffin, talc, tragacanth, bentonite, veegum, carboxyvinyl polymers, titanium dioxide, fatty acid esters, sorbitan fatty acid esters, sodium lauryl sulfate, glycerin, fatty acid glycerin ester, purified lanolin, glycerogelatin, polysorbates, macrogol, squalane, silicone oil, vegetable oils (sesame oil, olive oil, soybean oil, cottonseed oil, castor oil, etc.), liquid paraffin, soft paraffin, white petroleum, yellow petroleum, paraffin, wool fat, waxes (beeswax, carnauba wax, white beeswax, etc.), water, propylene glycol, polyethylene glycol, glycerol, lauryl alcohol, myristyl alcohol, oleyl alcohol, cetyl alcohol, ethanol, sodium chloride, sodium hydroxide, hydrochloric acid, citric acid, lauric acid, myristic acid, stearic acid, oleic acid, benzyl alcohol, glutamic acid, glycine, methyl p-hydroxybenzoate, propyl p-hydroxybenzoate, p-hydroxybenzoic acid esters, cholesterol esters, ethylene glycol monoalkyl esters, propylene glycol monoalkyl esters, glycerin monostearate, sorbitan fatty acid esters, isopropyl myristate, isopropyl palmitate, carboxypolymethylene, saccharin, strawberry flavor, peppermint flavor, cacao butter, polyisobutylene, vinyl acetate copolymers, acrylic copolymers, triethyl citrate, acetyl triethyl citrate, diethyl phthalate, diethyl sebacate, dibutyl sebacate, acetylated monoglyceride, diethylene glycol, dodecylpyrrolidone, urea, ethyl laurate, azone, kaolin, bentonite, zinc oxide, agarose, carrageenan, gum acacia, xanthan gum, potassium laurate, potassium palmitate, potassium myristate, sodium cetyl sulfate, sulfated castor oil (turkey-red oil), Span (sorbitan stearate, sorbitan monooleate, sorbitan sesquioleate, sorbitan trioleate, etc.), Tween (polysorbate 20, polysorbate 40, polysorbate 60, polysorbate 65, polysorbate 80, polysorbate 85, polyoxyethylene sorbitan fatty acid ester, etc.), polyoxyethylene hydrogenated castor oil (so-called HCO), polyoxyethylene lauryl ether, polyoxyethylene cetyl ether, polyoxyethylene oleyl ether, polyethylene glycol monolaurate, polyethylene glycol monostearate, poloxamers (so-called Pluronics), lecithin (also including purified phospholipids isolated from lecithin, such as phosphatidylcholine and phosphatidylserine), and hydrogenated lecithin.

The benzylpiperidine compound of the present invention and the pharmaceutically acceptable salt thereof, when used in the pharmaceutical applications as described above, are usually administered in the form of preparations comprising the compound or the salt mixed with pharmaceutical carriers, and these preparations are prepared according to usual methods. For example, the pharmaceutical composition can comprise 0.051 to 99% by weight, preferably 0.05 to 80% by weight, more preferably 0.1 to 70% by weight, even more preferably 0.1 to 50% by weight of the benzylpiperidine compound of the present invention or the pharmaceutically acceptable salt thereof as an active ingredient. These preparations may also contain other therapeutically valuable ingredients.

The benzylpiperidine compound of the present invention or the pharmaceutically acceptable salt thereof can be used in combination with a drug (combined drug) such as antidepressants, anxiolytic drugs, therapeutic drugs for schizophrenia, dopamine receptor agonists, therapeutic drug for Parkinson's disease, antiepileptics, anticonvulsants, analgesics, hormone preparations, therapeutic drugs for migraine, adrenaline β receptor antagonists, therapeutic drugs for dementia, and therapeutic drugs for mood disorder, for the purpose of potentiating its effect. Moreover, it can be used in combination with a drug (combined drug) such as antiemetics, sleep inducing drugs, and anticonvulsants, for the purpose of suppressing its side effects. The timing of administration of the compound of the present invention and the combined drug is not limited. They may be administered simultaneously or at any interval to an administration target. Moreover, the compound of the present invention and the combined drug may be administered as a mixture. The dose of the combined drug can be selected appropriately with respect to doses clinically used. Moreover, the ratio between the compound of the present invention and the combined drug formulated can be selected appropriately according to an administration target, an administration route, a target disease, symptoms, combinations, and so on. For example, when the administration target is a human, 0.01 to 1000 parts by weight of the combined drug can be used with respect to 1 part by weight of the compound of the present invention.

Hereinafter, the present invention will be described more specifically with reference to Reference Examples, Examples, and Test Examples. However, the technical scope of the present invention is not intended to be limited to these Examples. In this context, not all compound names shown in Reference Examples and Examples below follow the IUPAC nomenclature.

The compounds were identified using proton nuclear magnetic resonance absorption spectra ($^1$H-NMR spectra) or the like. For some of the compounds, their $^1$H-NMR spectrum data and melting points are shown. Moreover, purity or the like was also confirmed by liquid chromatography analysis. This analysis was conducted using a column SUMIPAX ODS C-212 (5 μm, 6 mmφ×15 cm) at a measurement wavelength set to 220 nm and a mobile phase flow rate set to 1.0 ml/min. The mobile phase used was a mixed solvent of 0.05% trifluoroacetic acid-acetonitrile (solution A) and 0.05% trifluoroacetic acid-water (solution B). Condition 1 involved increasing the proportion of the solution A in 0.625% increments per 1 minute such that the mixing ratio between the solutions A and B (solution A:solution B) was set to 25:75 at the start of measurement (0 min) and 50:50 after 40 minutes into the measurement. Condition 2 involved allowing the mixing ratio between the solutions A and B to remain constant at 40:60. For some of the compounds, the retention times at which the compounds were detected and the mixing ratio between the solutions A and B (Condition 1 or 2) are also shown.

Reference Example 1

4-[3-Bromo-5-(2-methoxyethoxy)benzyl]piperidine hydrochloride, compound (RE1)

The compound was synthesized according to the following Production Method 1 or 2:

Production Method 1

[Formula 20]

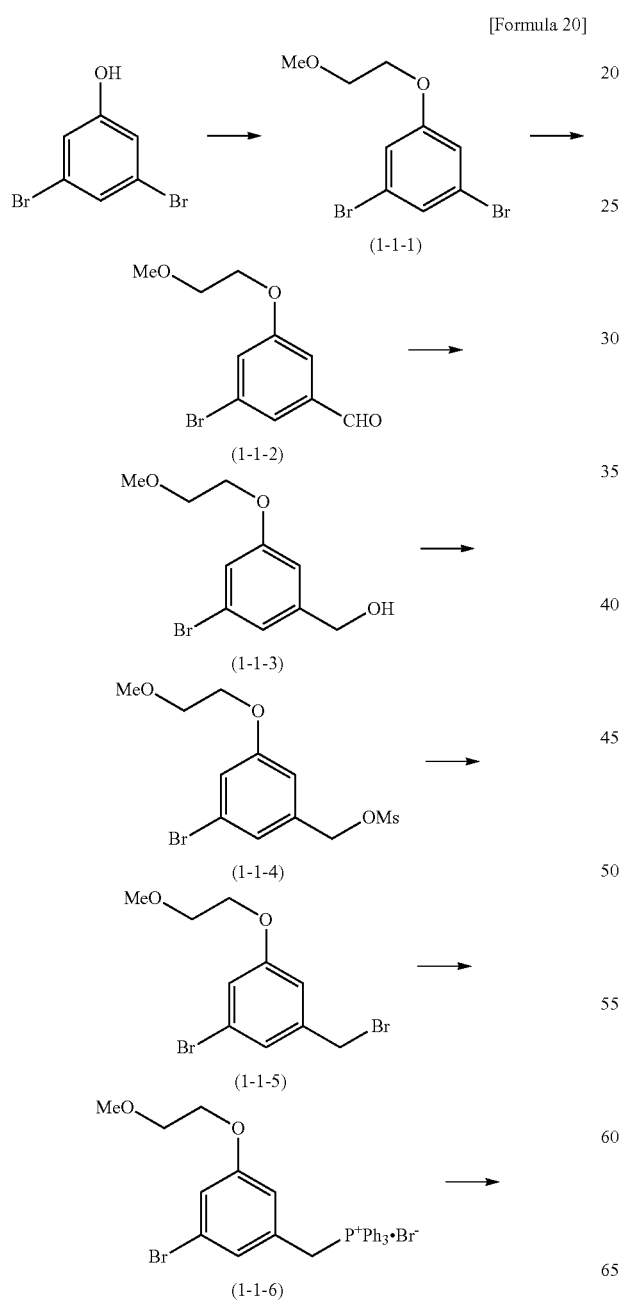

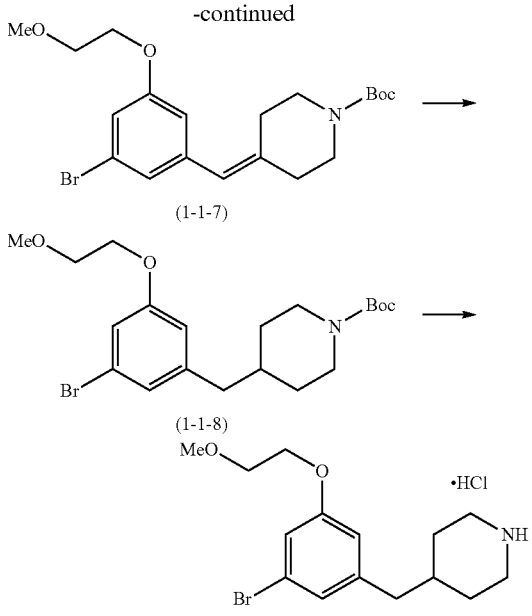

Compound (1-1-1): 1,3-Dibromo-5-(2-methoxyethoxy)benzene

2-Bromoethyl methyl ether (31.2 g, 224 mmol) was added at room temperature to a solution of 3,5-dibromophenol (37.7 g, 150 mmol) and potassium carbonate (41.4 g, 300 mmol) in dimethylformamide (150 mmol), and the reaction mixture was stirred at 80° C. for 9 hours. The mixture was cooled to room temperature and then separated into aqueous and organic layers by the addition of water (300 mL), toluene (150 mL), and ethyl acetate (150 mL). The aqueous layer was extracted with a mixed solution of toluene (50 mL) and ethyl acetate (50 mL). The combined organic layers were washed with water (50×2 mL) and brine (50 mL) and dried over anhydrous sodium sulfate, and the solvent was then distilled off under reduced pressure. The obtained concentrated residue was purified by silica gel column chromatography (n-hexane:ethyl acetate=20:1→15:1) to obtain the title compound (1-1-1) (44.3 g, 95%) as a brown oil.

Compound (1-1-2): 3-Bromo-5-(2-methoxyethoxy)benzaldehyde n-Butylmagnesium chloride (0.89 M solution in tetrahydrofuran, 116 mL, 100 mmol) was added dropwise over 25 minutes to a solution of n-butyllithium (1.6 M solution in n-hexane, 126 mL, 198 mmol) in toluene (120 mL) with the solution temperature kept at 3 to 5° C. by cooling in an ice bath, and the reaction mixture was stirred at this temperature for 30 minutes. A solution of the compound (1-1-1) (46.1 g, 149 mmol) in toluene (420 mL) was added dropwise thereto over 1 hour with the solution temperature kept at 0 to 3° C., and the reaction mixture was stirred for 2 hours. Then, N,N-dimethylformamide (28.7 mL, 373 mmol) was added dropwise thereto at the solution temperature of 4 to 5° C. over 40 minutes, and the reaction mixture was stirred for 2 hours. A 2 N aqueous hydrochloric acid solution (300 mL) was added thereto, and the mixture was warmed to room temperature and separated into aqueous and organic layers. The aqueous layer was subjected to extraction with toluene (100 mL). The combined organic layers were washed with water and brine and then dried over anhydrous sodium sulfate, and the solvent was distilled off under reduced pressure. The obtained concentrated residue was purified by silica gel column chromatography (n-hexane:ethyl acetate=10:1→7:1) to obtain the title compound (1-1-2) (28.8 g, 74%).

Compound (1-1-3): [3-Bromo-5-(2-methoxyethoxy)phenyl]methanol

Sodium borohydride (4.22 g, 112 mmol) was added in small portions at room temperature to a solution of the compound (1-1-2) (28.9 g, 112 mmol) in methanol (112 mL) with water cooling, and the reaction mixture was stirred at room temperature for 3 hours. Water (200 mL) was added thereto, and the methanol was distilled off under reduced pressure, followed by extraction with ethyl acetate (200 mL+50 mL). The organic layer was washed with brine and dried over anhydrous sodium sulfate, and the solvent was then distilled off under reduced pressure to obtain the title compound (1-1-3) (28.7 g, 98%) as a pale yellow oil.

Compound (1-1-4): 3-Bromo-5-(2-methoxyethoxy)benzyl methanesulfonate

A solution of methanesulfonyl chloride (16.0 g, 140 mmol) in toluene (15 mL) was added dropwise over 50 minutes to a solution of the compound (1-1-3) (24.3 g, 93.1 mmol), triethylamine hydrochloride (890 mg, 9.3 mmol), and triethylamine (25.9 mL, 186 mmol) in toluene (186 mL) with the solution temperature kept at 10° C. or lower in a salt-ice bath, and the reaction mixture was stirred at the solution temperature of 5° C. or lower for 1 hour. 2-Diethylaminoethylamine (5.95 g, 51.2 mmol) was added thereto at the solution temperature of 5° C. or lower, and the mixture was stirred for 20 minutes. Subsequently, a 5% aqueous potassium bisulfate solution (250 mL) and water (100 mL) were added to the reaction solution, and the mixture was warmed to room temperature and separated into aqueous and organic layers. The organic layer was washed with water, and the toluene was then distilled off under reduced pressure to obtain the title compound (1-1-4) (33.1 g).

Compound (1-1-5): 1-Bromo-3-(bromomethyl)-5-(2-methoxyethoxy)benzene

Lithium bromide monohydrate (30.7 g, 293 mmol) was added at room temperature to a solution of the compound (1-1-4) (33.1 g, which corresponds to 97.6 mmol) in anhydrous tetrahydrofuran (195 mL), and the reaction mixture was heated under reflux for 1 hour. The mixture was cooled to room temperature and then separated into aqueous and organic layers by the addition of toluene (180 mL) and water. The aqueous layer was extracted with toluene (50 mL). The combined organic layers were washed with brine and dried over anhydrous sodium sulfate, and the toluene was then distilled off under reduced pressure to obtain the title compound (1-1-5) (29.3 g, 93%).

Compound (1-1-6): [3-Bromo-5-(2-methoxyethoxy)benzyl](triphenyl)phosphonium bromide A solution of the compound (1-1-5) (31.8 g, 98 mmol) and triphenylphosphine (28.3 g, 108 mmol) in toluene (98 mL) was heated under reflux for 3 hours. The reaction mixture was gradually cooled to room temperature, and the resulting precipitate was collected by filtration, washed with toluene (40 mL), and dried under reduced pressure to obtain the title compound (1-1-6) (50.1 g, 87%).

Compound (1-1-7): tert-Butyl 4-{[3-bromo-5-(2-methoxyethoxy)phenyl]methylidene}piperidine-1-carboxylate A suspension of the compound (1-1-6) (50.1 g, 85 mmol), 1-tert-butoxycarbonyl-4-piperidone (17.4 g, 87 mmol), and potassium carbonate (23.6 g, 171 mmol) in 2-propanol (250 mL) was stirred at 40° C. for 4 hours, at 50° C. for 2 hours, at 60° C. for 3.5 hours, and then heated under reflux at 80° C. for 7.5 hours. The reaction mixture was cooled to room temperature, and the salt was then filtered off. The filtrate was concentrated under reduced pressure. The obtained concentrated residue was purified by silica gel column chromatography (n-hexane:ethyl acetate=10:1→7:1) to obtain the title compound (1-1-7) (34.6 g, 95%) as a colorless oil.

Compound (1-1-8): tert-Butyl 4-[3-bromo-5-(2-methoxyethoxy)benzyl]piperidine-1-carboxylate The compound (1-1-7) (34.6 g, 81 mmol) was subjected to atmospheric hydrogenation reaction at room temperature for 26 hours in ethyl acetate (80 mL) over 5% rhodium carbon (9.74 g). The catalyst was filtered off. The filtrate was concentrated under reduced pressure to obtain the title compound (1-1-8) (34.2 g, 98%).

Compound (RE1)

A 10% hydrochloric acid-methanol solution (103 mL) was added at room temperature to a solution of the compound (1-1-8) (34.2 g, 80 mmol) in methanol (34 mL), and the reaction mixture was stirred at room temperature for 1 day. The solvent was distilled off under reduced pressure. Then, diethyl ether was added to the obtained concentrated residue, and the resulting precipitate was collected by filtration, washed with diethyl ether and then dried under reduced pressure to obtain a white solid (27.5 g). To this white-solid, acetonitrile (132 mL) was added, and the mixture was heated to 50° C. The complete dissolution thereof was confirmed, and the solution was then gradually cooled and stirred at 40° C. for 30 minutes. Then, the solution was cooled to 0° C. over 1 hour and stirred at 0° C. for 1 hour. The precipitate was collected by filtration, then washed with cold acetonitrile (20 mL), and dried under reduced pressure to obtain the compound (RE1) of interest (22.6 g, 85%) as a white powder.

Retention time (Condition 1): 15.56 minutes
Melting point: 107-108° C.
$^1$H-NMR (400 MHz, d$^6$-DMSO) δ: 1.25-1.40 (2H, m), 1.67 (2H, d like, J=14 Hz), 1.72-1.85 (1H, m), 2.49 (2H, d, J=6.8 Hz), 2.77 (2H, dt, J=2.4, 12 Hz), 3.20 (2H, br d, J=12.6 Hz), 3.34 (3H, s), 3.63 (2H, t like, J=4.5 Hz), 4.09 (2H, t like, J=4.5 Hz), 6.80 (1H, t, J=1.7 Hz), 6.96-6.99 (2H, m).
Production Method 2

[Formula 21]

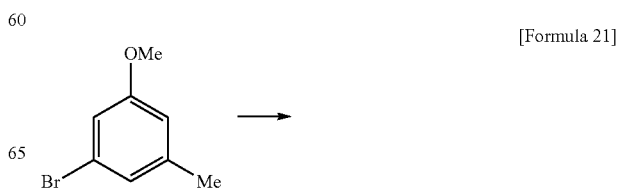

-continued

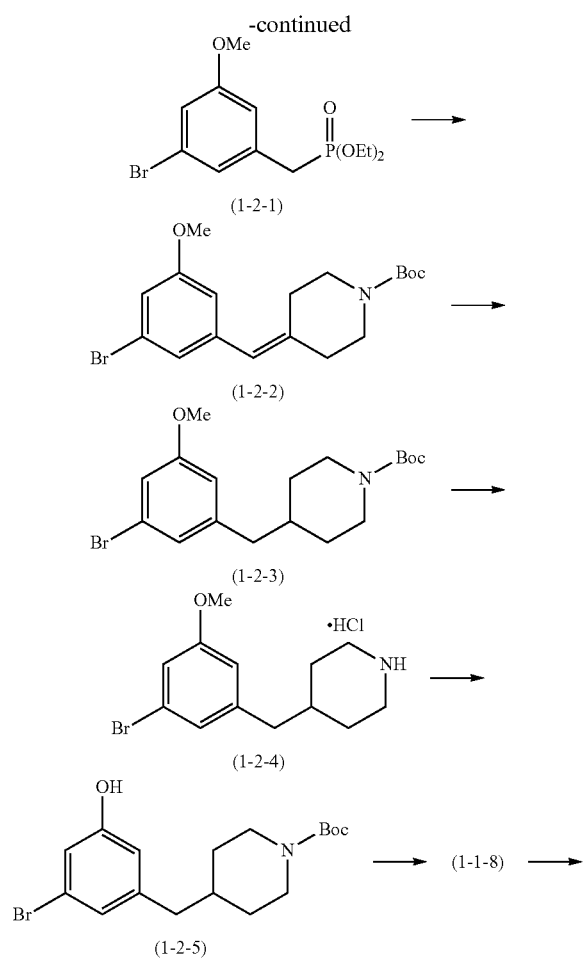

(RE1)

Compound (1-2-1): Diethyl (3-Bromo-5-methoxybenzyl)phosphonate 5,5-Dimethyl-1,3-dibromohydantoin (13.1 g, 46 mmol) and azobisisobutyronitrile (1.50 g, 9.1 mmol) were simultaneously added at 80° C. to a solution of 1-bromo-3-methoxy-5-methylbenzene (17.0 g, 91 mmol) synthesized by a method of the document (J. Med. Chem. 2001, 44, 1866) in monochlorobenzene (500 mL), and the reaction mixture was stirred at 80° C. for 30 minutes. The reaction solution was cooled to room temperature and then poured into a 10% aqueous sodium thiosulfate solution (100 mL), and the mixture was stirred for 30 minutes. The mixture was separated into aqueous and organic layers. The aqueous layer was subjected to extraction with toluene (100 mL). The combined organic layers were dried over anhydrous sodium sulfate, and the solvent was then distilled off under reduced pressure to obtain 1-bromo-3-(bromomethyl)-5-methoxybenzene. Without further purification, this compound was dissolved in triethyl phosphite (14.3 mL, 97 mmol) and toluene (50 mL), and the reaction mixture was heated under reflux for 7 hours. After cooling to room temperature, the solvent was distilled off under reduced pressure. The obtained concentrated residue was purified by silica gel column chromatography (n-hexane:ethyl acetate=1:2) to obtain the title compound (1-2-1) (20.8 g, 64%).

Compound (1-2-2): tert-Butyl 4-(3-bromo-5-methoxybenzylidene)piperidine-1-carboxylate A solution of the compound (1-2-1) (19.0 g, 56 mmol) in anhydrous tetrahydrofuran (100 mL) was added dropwise at 50° C. over 15 minutes to a suspension of sodium hydride (60% suspension, 2.71 g, 68 mmol) in anhydrous tetrahydrofuran (100 mL). The reaction mixture was stirred at 50° C. for 25 minutes. Then, a solution of 1-tert-butoxycarbonyl-4-piperidone (14.5 g, 73 mmol) in anhydrous tetrahydrofuran (100 mL) was added dropwise thereto at 50° C. over 30 minutes, and the reaction mixture was stirred for 1 hour. Subsequently, 1-tert-butoxycarbonyl-4-piperidone (5.00 g, 25 mmol) and sodium hydride (60% suspension, 1.00 g, 25 mmol) were added thereto, and the reaction mixture was stirred for 1.5 hours. After cooling to room temperature, water (100 mL) was added thereto, and the mixture was subjected to extraction with ethyl acetate. The organic layer was washed with brine and then dried over anhydrous magnesium sulfate. The solvent was distilled off under reduced pressure. Then, n-hexane (10 mL) and ethyl acetate (10 mL) were added to the obtained concentrated residue, and the resulting solid was collected by filtration, washed with n-hexane/ethyl acetate (1:1, 5 mL×3), and dried under reduced pressure to obtain the title compound (1-2-2) (11.3 g, 52%).

Compound (1-2-3): (tert-Butyl 4-(3-bromo-5-methoxybenzyl)piperidine-1-carboxylate The compound (1-2-2) (19.0 g, 50 mmol) was subjected to atmospheric hydrogenation reaction at room temperature for 1.5 hours in ethyl acetate (300 mL) over 5% rhodium carbon (10.3 g, 10 mol %). The catalyst was filtered off. The filtrate was concentrated under reduced pressure to obtain the title compound (1-2-3) (20.6 g, quantitative).

Compound (1-2-4): 4-(3-Bromo-5-methoxybenzyl)piperidine hydrochloride

A 10% hydrochloric acid-methanol solution (150 mL) was added at room temperature to a solution of the compound (1-2-3) (20.6 g, 50 mmol) in methanol (30 mL), and the reaction mixture was stirred at 50° C. for 45 minutes. After cooling to room temperature, the solvent was distilled off under reduced pressure. Then, diethyl ether was added to the obtained concentrated residue, and the resulting precipitate was collected by filtration, washed with diethyl ether and then dried under reduced pressure to obtain the title compound (1-2-4) (15.4 g, 97%).

Retention time (Condition 1): 16.40 minutes

Compound (1-2-5): tert-Butyl 4-(3-bromo-5-hydroxybenzyl)piperidine-1-carboxylate A solution of the compound (1-2-4) (15.0 g, 47 mmol) in dichloromethane (200 mL) was cooled in an ice bath, and a 1 M boron tribromide-dichloromethane solution (70 mL, 70 mmol) was added dropwise thereto over 30 minutes. The reaction mixture was stirred for 2 hours with ice cooling, and a 1 M boron tribromide-dichloromethane solution (50 mL, 50 mmol) was further added dropwise thereto with ice cooling. The reaction mixture was stirred for 2 hours, and methanol (50 mL) was then added dropwise thereto with the solution temperature kept at 20° C. or lower. The solvent was distilled off under reduced pressure. The obtained concentrated residue was dissolved by the addition of a 2 N aqueous sodium hydroxide solution (200 mL) and 1,4-dioxane (400 mL), and a solution of di-tert-butyl dicarbonate (10.3 g, 47 mmol) in 1,4-dioxane (50 mL) was added dropwise thereto at room temperature over 30 minutes. The reaction mixture was stirred overnight at room temperature. Then, the 1,4-dioxane was distilled off under reduced pressure, and water (300 mL) was added to the concentrated residue, followed by extraction with ethyl acetate. The organic layer was washed with brine and dried over anhydrous magnesium sulfate, and the solvent was then distilled off under reduced pressure. The obtained concentrated residue was purified by silica gel column chromatography (n-hexane:ethyl acetate=4:1) to obtain the title compound (1-2-5) (15.8 g, 91%).

Compound (1-1-8)

A solution of the compound (1-2-5) (15.8 g, 43 mmol), 2-bromoethyl methyl ether (6.0 mL, 64 mmol), potassium iodide (7.09 g, 43 mmol), and potassium carbonate (11.8 g, 85 mmol) in dimethylformamide (100 mL) was stirred at 60 to 70° C. for 8 hours. 2-Bromoethyl methyl ether (1.0 mL, 11 mmol) was further added thereto, and the reaction mixture was stirred for 2 hours. The mixture was cooled to room temperature and then poured to water (500 mL), followed by extraction with ethyl acetate/toluene (1:1, 200 mL×3). The organic layer was washed with water, and the solvent was then distilled off under reduced pressure. The obtained concentrated residue was purified by silica gel column chromatography (n-hexane:ethyl acetate=5:1) to obtain the title compound (1-1-8) (18.4 g, quantitative).

Compound (RE1)

A 10% hydrochloric acid-methanol solution (200 mL) was added at room temperature to a solution of the compound (1-1-8) (18.4 g, 43 mmol) in methanol (30 mL), and the reaction mixture was stirred overnight at room temperature. The methanol was distilled off under reduced pressure. Diethyl ether (100 mL) was added to the obtained concentrated residue, and the resulting precipitate was collected by filtration, washed with diethyl ether (50 mL) and then dried under reduced pressure to obtain the compound (RE1) of interest (14.7 g, 95%).

Reference Example 2

4-[3-Chloro-5-(2-methoxyethoxy)benzyl]piperidine, compound (RE2)

[Formula 22]

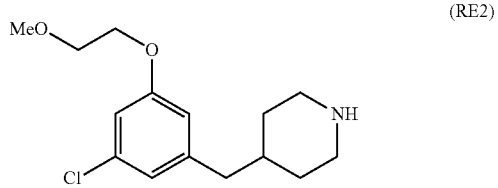

(RE2)

A solution of the compound (1-1-8) (800 mg, 1.8 mmol) and copper(I) chloride (537 mg, 5.4 mmol) in dimethylformamide (5.4 mL) was stirred at 150° C. for 6 hours. After cooling to room temperature, the salt was filtered off. The solvent in the filtrate was distilled off under reduced pressure. A 2 N aqueous sodium hydroxide solution and chloroform were added to the obtained concentrated residue, and the resulting precipitate was filtered off. The filtrate was subjected to extraction with ethyl acetate. The organic layer was dried over anhydrous sodium sulfate, and the solvent was then distilled off under reduced pressure to obtain the title compound (RE2) (520 mg, quantitative).

$^1$H-NMR (300 MHz, CDCl$_3$) δ: 1.04-1.20 (2H, m), 1.52-1.83 (3H, m), 2.45 (2H, bd, J=6.8 Hz), 2.47-2.61 (2H, m), 3.04 (2H, bd, J=11.9 Hz), 3.45 (3H, s), 3.72-3.75 (2H, m), 4.07-4.10 (2H, m), 6.62 (1H, bt, J=1.8 Hz), 6.72-6.78 (2H, m).

Reference Example 3

4-[4-Bromo-3-(2-methoxyethoxy)benzyl]piperidine hydrochloride, compound (RE3)

The compound was synthesized according to the following Production Method 1, 2, or 3:

Production Method 1

[Formula 23]

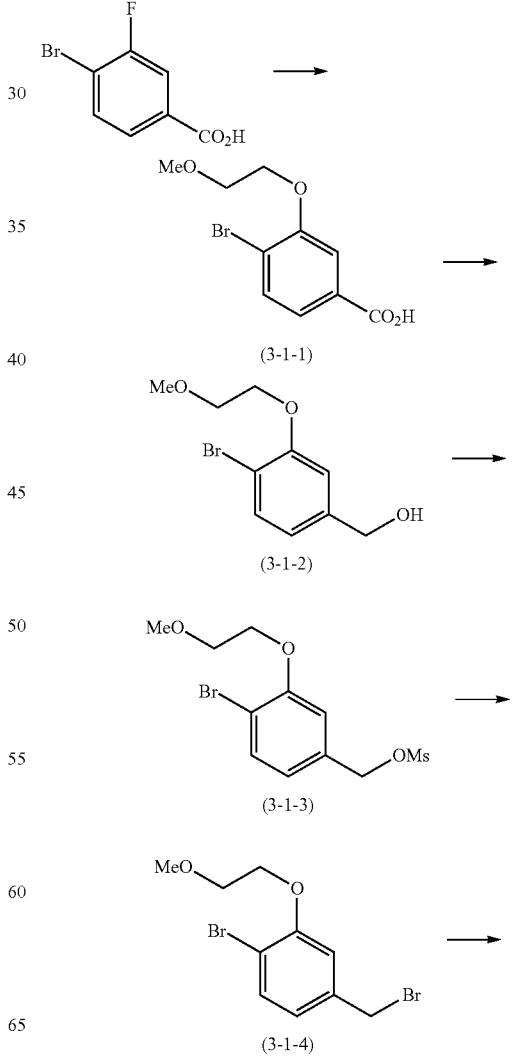

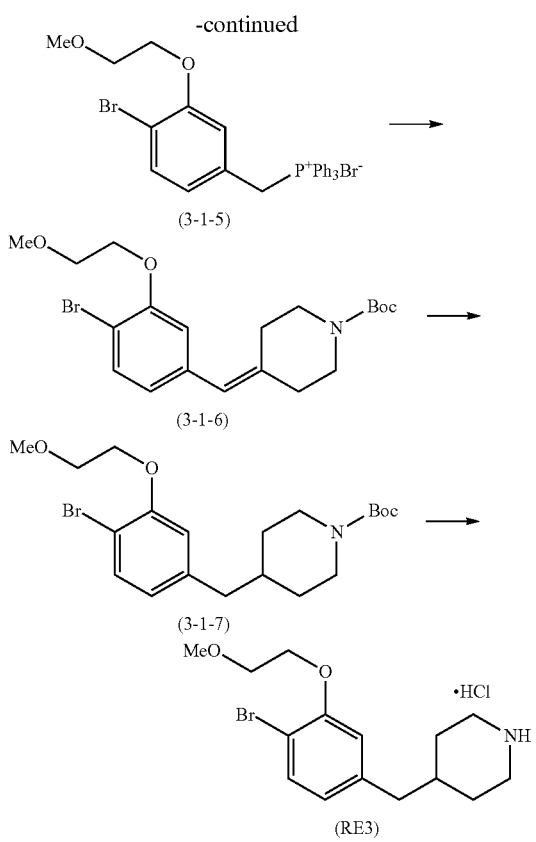

Compound (3-1-1): 4-Bromo-3-(2-methoxyethoxy)benzoic acid

Potassium t-butoxide (24.29 g, 217 mmol) was added at room temperature to a solution of 2-methoxyethanol (16.48 g, 217 mmol) in anhydrous N-methyl-2-pyrrolidinone (175 mL) under nitrogen atmosphere. The dissolution thereof was visually confirmed, and 4-bromo-3-fluorobenzoic acid (19.00 g, 86.8 mmol) was then added thereto in small portions. The reaction mixture was stirred at 90° C. for 6 hours. The mixture was cooled to room temperature and then added dropwise to a solution of concentrated hydrochloric acid (36%, 25 mL) and water (500 mL) over 40 minutes with water cooling. The mixture was stirred at the solution temperature of 20 to 25° C. for 1 hour, and the resulting precipitate was then collected by filtration, washed with water (20 mL×2) and acetonitrile (20 mL×2), and dried under reduced pressure to obtain a white solid (26.41 g). This white solid was added to acetonitrile (380 mL), and the mixture was heated to around a reflux temperature. The dissolution thereof was visually confirmed, and the solution was then cooled to around 75° C. at which crystal deposition started. Then, the mixture was stirred for 1 hour with the temperature kept at 65 to 70° C. Then, the mixture was cooled again to around 30° C. over 2.5 hours and subsequently stirred for 1 hour with the solution temperature kept at 20° C. by water cooling. The resulting precipitate was collected by filtration, washed with acetonitrile (20 mL×2) to obtain the title compound (3-1-1) (20.09 g, 85%) as a light brown needle-like crystal.

Compound (3-1-2): [4-Bromo-3-(2-methoxyethoxy)phenyl]methanol

A boron trifluoride/diethyl ether complex (35 mL, 285 mmol) was added dropwise to a suspension of sodium borohydride (8.08 g, 213.5 mmol) in anhydrous tetrahydrofuran (100 mL) with water cooling, and the mixture was stirred at this temperature for 1 hour. A solution of the compound (3-1-1) (19.50 g, 71.2 mmol) in anhydrous tetrahydrofuran (300 mL) was added dropwise thereto over 30 minutes with the solution temperature kept at 25° C. or lower by water cooling. The reaction mixture was stirred for 3 hours, and water (200 mL) was then added dropwise thereto over 20 minutes with the solution temperature kept at 20° C. or lower by ice cooling. The mixture was separated into aqueous and organic layers by the addition of toluene (200 mL). The aqueous layer was extracted with toluene (200 mL). The combined organic layers were washed with a 3% aqueous sodium bicarbonate solution (200 mL) and water (200 mL), and the toluene was then distilled off under reduced pressure. Toluene (200 mL) was added to the concentrated residue, and the toluene was distilled off under reduced pressure to obtain the title compound (3-1-2) (18.18 g).

Compound (3-1-3): 4-Bromo-3-(2-methoxyethoxy)benzyl methanesulfonate

A toluene (18 mL) solution of methanesulfonyl chloride (8.56 g, 74.7 mmol) was added dropwise over 30 minutes to a solution of the compound (3-1-2) (18.00 g, which corresponds to 71.17 mmol), trimethylamine hydrochloride (467 mg, 7.12 mmol), and triethylamine (19.8 mL, 142 mmol) in toluene (90 mL) with the solution temperature kept at 5° C. or lower in a salt-ice bath, and the reaction mixture was stirred at the solution temperature of 5° C. or lower for 2 hours. The reaction solution was poured into a 5% aqueous potassium bisulfate solution (180 mL) with the temperature kept at 10° C. or lower by cooling in an ice bath, and the mixture was stirred for 30 minutes. The mixture was warmed to room temperature and separated into aqueous and organic layers. The aqueous layer was extracted with toluene (90 mL). The combined organic layers were washed with water (180 mL), and the toluene was distilled off under reduced pressure to obtain the title compound (3-1-3) (22.43 g).

Compound (3-1-4): 1-Bromo-4-(bromomethyl)-2-(2-methoxyethoxy)benzene

Anhydrous lithium bromide (18.54 g, 214 mmol) was added at room temperature to a solution of the compound (3-1-3) (22.43 g, which corresponds to 71.17 mmol) in anhydrous tetrahydrofuran (100 mL), and the reaction mixture was heated under reflux for 1 hour. The mixture was cooled to room temperature and then separated into aqueous and organic layers by the addition of water (100 mL) and toluene (100 mL). The aqueous layer was extracted with toluene (100 mL). The combined organic layers were washed with a 5% aqueous sodium bicarbonate solution (100 mL) and water (100 mL) in this order, and the toluene was distilled off under reduced pressure to obtain the title compound (3-1-4) (19.54 g) as a white solid.

Alternatively, the present title compound (3-1-4) can also be synthesized directly from the compound (3-1-2) as follows without being subjected to the intermediary step with the compound (3-1-3):

A solution of the compound (3-1-2) (16.0 g, 61.3 mmol) in toluene (80 g) and aqueous hydrogen bromide (47%, 53 g) was stirred at the solution temperature of 65 to 70° C. for 2 hours. The mixture was cooled to room temperature and then separated into aqueous and organic layers by the addition of water (16 g). The organic layer was washed with a 5% aqueous sodium bicarbonate solution (48 g) and water (48 g) in this order. The organic layer was concentrated under reduced pressure to obtain the title compound (3-1-4) (17.9 g, 90%).

Compound (3-1-5): [4-Bromo-3-(2-methoxyethoxy)benzyl](triphenyl)phosphonium bromide Triphenylphosphine (18.67 g, 71.17 mmol) was added to a solution of the compound (3-1-4) (19.54 g, which corresponds to 71.17 mmol) in toluene (100 mL), and the reaction mixture was heated under reflux for 3.5 hours. The mixture was cooled to room temperature and then stirred for 1 hour with the temperature kept at 20° C. with water cooling, and the resulting precipitate was then collected by filtration, washed with toluene (40 mL×3), and dried under reduced pressure to obtain the title compound (3-1-5) (32.44 g, 78%).

Compound (3-1-6): tert-Butyl 4-[4-bromo-3-(2-methoxyethoxy)benzylidene]piperidine-1-carboxylate A solution of the compound (3-1-5) (32.00 g, 54.6 mmol), 1-tert-Butoxycarbonyl-4-piperidone (11.42 g, 57.3 mmol), and potassium carbonate (11.30 g, 81.9 mmol) in 2-propanol (160 mL) was heated under reflux for hours. After cooling to room temperature, the salt was separated by filtration, and this residue salt was washed with 2-propanol (30 mL×2). The filtrate was concentrated under reduced pressure to obtain a concentrated residue (41.08 g). Toluene was added thereto and distilled off under reduced pressure (200 mL×2). Subsequently, toluene (96 mL) was added to the concentrated residue, and n-hexane (290 mL) was added dropwise thereto over 30 minutes with the temperature kept at 20 to 25° C. by water cooling. The mixture was stirred at this temperature for 1 hour and then stirred for 1 hour with ice cooling, and the resulting precipitate was separated by filtration. The residue on the filter was washed with toluene/n-hexane (toluene:n-hexane=1:3, 20 mL×2). The solvent in the filtrate was distilled off under reduced pressure to obtain the title compound (3-1-6) (27.93 g) as a pale yellow oil.

Compound (3-1-7): tert-Butyl 4-[4-bromo-3-(2-methoxyethoxy)benzyl]piperidine-1-carboxylate The compound (3-1-6) (27.93 g, which corresponds to 54.6 mmol) was subjected to atmospheric hydrogenation reaction at the solution temperature of 15 to 20° C. for 3 hours in ethyl acetate (232 mL) over 5% rhodium carbon (5.80 g). The catalyst was filtered off through celite. Then, the ethyl acetate was distilled off under reduced pressure to obtain the title compound (3-1-7) (25.73 g) as a white solid.

Compound (RE3)

A solution of the compound (3-1-7) (25.73 g, which corresponds to 54.6 mmol) in 2-propanol (115 mL) was warmed to the solution temperature of 55 to 60° C. Concentrated hydrochloric acid (36%, 23.2 mL) was added dropwise thereto over 5 minutes, and the reaction mixture was stirred at the solution temperature of 55 to 60° C. for 4 hours. After cooling to room temperature, the 2-propanol was distilled off under reduced pressure to obtain a concentrated residue (42.91 g). This concentrated residue was separated into aqueous and organic layers by the addition of water (115 mL) and toluene (115 mL). The organic layer was extracted with water (50 mL). The combined aqueous layers were adjusted to approximately pH 10 with sodium hydroxide and subjected to extraction with toluene (200+100+100 mL). The organic layer was washed with water (50 mL), and the toluene was distilled off under reduced pressure to obtain a concentrated residue (18.57 g). This concentrated residue was dissolved in 2-propanol. To the solution, concentrated hydrochloric acid (36%, 5.58 g, 54.6 mmol) was added at room temperature, and the 2-propanol was distilled off under reduced pressure. 2-Propanol (200 mL×2) was added to the concentrated residue and distilled off under reduced pressure to obtain a concentrated residue (18.61 g) as a white powder. To this concentrated residue, 2-propanol (115 mL) was added. The uniform solution at the solution temperature around 65 to 70° C. was visually confirmed and then allowed to cool slowly. Crystal deposition at around 60° C. was confirmed, and n-hexane (60 mL) was then added dropwise thereto at the solution temperature of 55 to 60° C. over 20 minutes. The suspension was stirred at the solution temperature of 55 to 60° C. for 1 hour and then allowed to cool slowly again to the solution temperature of 30° C. or lower. Then, the suspension was stirred for 1 hour with the solution temperature kept at 15 to 20° C. by water cooling and further stirred at the solution temperature of 5° C. or lower for 1 hour by ice cooling. The precipitate was collected by filtration, washed with a cold n-hexane (23 mL)-2-propanol (12 mL) mixed solution and then dried under reduced pressure to obtain the compound (RE3) of interest (17.30 g) as a white powder.

Retention time (Condition 1): 15.55 minutes

Melting point: 171-172° C.

$^1$H-NMR (300 MHz, CDCl$_3$) δ: 1.47-1.94 (5H, m), 2.55 (2H, d, J=5.5 Hz), 2.79 (2H, t like, J=12 Hz), 3.47 (2H, d like, J=13 Hz), 3.51 (3H, s), 3.81 (2H, t, J=4.8 Hz), 4.15 (2H, t, J=4.8 Hz), 6.62 (1H, dd, J=7.9, 1.8 Hz), 6.68 (1H, d, J=1.7 Hz), 7.43 (1H, d, J=8.1 Hz), 9.50 (2H, br s).

Production Method 2

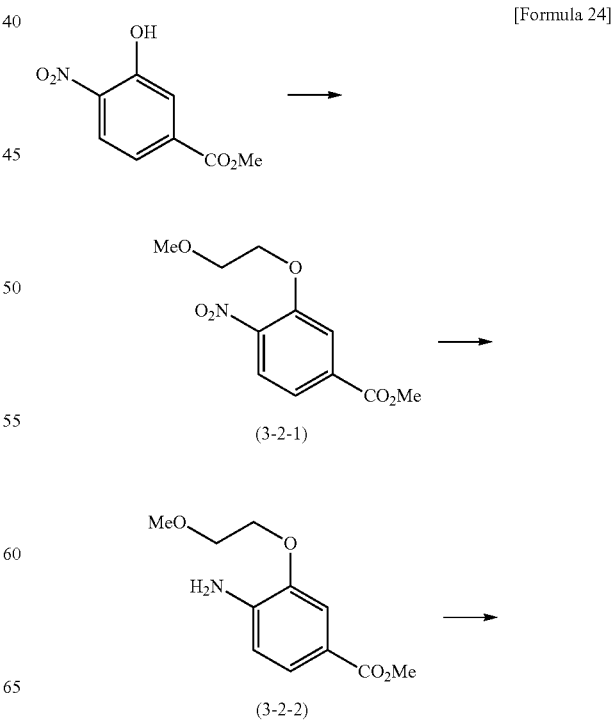

[Formula 24]

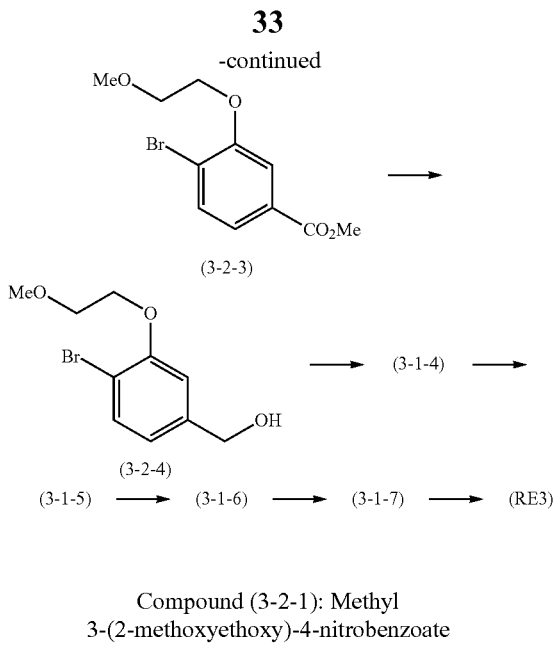

Compound (3-2-1): Methyl 3-(2-methoxyethoxy)-4-nitrobenzoate

A solution of Methyl 3-hydroxy-4-nitrobenzoate (15.0 g, 76 mmol), 2-bromoethyl methyl ether (14.5 g, 99 mmol), potassium iodide (12.6 g, 76 mmol), and potassium carbonate (21.4 g, 155 mmol) in dimethylformamide (250 mL) was stirred at 60 to 70° C. for 3 hours. 2-Bromoethyl methyl ether (5.00 g, 36 mmol) was further added thereto, and the reaction mixture was stirred at 60 to 70° C. for 2 hours and then stirred overnight at room temperature. The reaction mixture was poured into water (600 mL), followed by extraction with ethyl acetate/toluene (1:1, 500 mL×2). The organic layer was washed with a 5% aqueous potassium carbonate solution and water in this order, and the solvent was distilled off under reduced pressure to obtain the title compound (3-2-1) (20.2 g, quantitative).

Compound (3-2-2): Methyl 4-amino-3-(2-methoxyethoxy)benzoate

The compound (3-2-1) (20.2 g, 76 mmol) was subjected to atmospheric hydrogenation reaction at room temperature for 2 hours in methanol (200 mL) over 10% palladium carbon (8.06 g, 10 mol %). The termination of hydrogen absorption was confirmed, and the catalyst was filtered off. The filtrate was concentrated under reduced pressure to obtain the title compound (3-2-2) (16.7 g, 98%).

Compound (3-2-3): Methyl 4-bromo-3-(2-methoxyethoxy)benzoate

A solution of the compound (3-2-2) (10.0 g, 44 mmol) in 48% aqueous hydrobromic acid (50 mL) was cooled in an ice bath. A solution of sodium nitrite (3.07 g, 45 mmol) in water (30 mL) was added dropwise thereto over 30 minutes, and the reaction mixture was stirred for 1 hour. This solution kept at 5° C. or lower was added dropwise over 20 minutes to a solution of copper(I) bromide (4.17 g, 29 mmol) in 48% aqueous hydrobromic acid (50 mL) heated to 60° C., and the reaction mixture was stirred at 60° C. for 1 hour. The mixture was cooled to room temperature and then poured into water (400 mL), followed by extraction with diethyl ether. The organic layer was washed with water and brine in this order. The organic layer was dried over anhydrous magnesium sulfate, and the solvent was then distilled off under reduced pressure. The obtained concentrated residue was purified by silica gel column chromatography (n-hexane:ethyl acetate=4:1) to obtain the title compound (3-2-3) (9.77 g, 76%).

Compound (3-2-4): [4-Bromo-3-(2-methoxyethoxy)phenyl]methanol

A solution of the compound (3-2-3) (10.0 g, 35 mmol) in anhydrous tetrahydrofuran (50 mL) was gradually heated under reflux, while a 1.0 M solution of borane/tetrahydrofuran complex in tetrahydrofuran (140 mL, 140 mmol) was added dropwise thereto. The reaction mixture was heated under reflux for 20 hours. After cooling to room temperature, water was added thereto until the gas evolution ceased. The tetrahydrofuran was distilled off under reduced pressure. An aqueous saturated sodium bicarbonate solution was added to the concentrated residue, followed by extraction with chloroform. The organic layer was dried over anhydrous sodium sulfate, and the solvent was then distilled off under reduced pressure. The obtained concentrated residue was purified by silica gel column chromatography (n-hexane:ethyl acetate=1:1) to obtain the title compound (3-2-4) (9.13 g, quantitative).

Compound (3-1-4)

Carbon tetrabromide (15.5 g, 48 mmol) was added at the solution temperature of 20° C. or lower to a solution of the compound (3-2-4) (9.00 g, 34.5 mmol) and triphenylphosphine (10.9 g, 41 mmol) in dichloromethane (200 mL) with ice cooling, and the reaction mixture was stirred for 1.5 hours with ice cooling. The solvent was distilled off under reduced pressure. The obtained concentrated residue was purified by silica gel column chromatography (chloroform) to obtain the title compound (3-1-4) (9.88 g, 88%).

Compound (3-1-5)

A solution of the compound (3-1-4) (9.85 g, 30 mmol) and triphenylphosphine (9.57 g, 36.5 mmol) in toluene (200 mL) was heated under reflux for 16 hours. The reaction mixture was gradually cooled to room temperature and subsequently stirred for 30 minutes in an ice bath, and the resulting precipitate was then collected by filtration, washed with toluene (10 mL×2), and dried under reduced pressure to obtain the title compound (3-1-5) (19.4 g, quantitative).

Compound (3-1-6)

A suspension of the compound (3-1-5) (19.0 g, 32 mmol), 1-tert-butoxycarbonyl-4-piperidone (7.10 g, 36 mmol), and potassium carbonate (6.71 g, 49 mmol) in 2-propanol (200 mL) was heated under reflux for 11.5 hours. The reaction mixture was cooled to room temperature, and the salt was then filtered off. The filtrate was concentrated under reduced pressure. n-Hexane/ethyl acetate (4:1, 200 mL) was added to the obtained concentrated residue, and the resulting triphenylphosphine oxide was filtered off. The filtrate was concentrated under reduced pressure. The obtained concentrated residue was purified by silica gel column chromatography (n-hexane:ethyl acetate=4:1) to obtain the title compound (3-1-6) (14.2 g, quantitative).

Compound (3-1-7)

The compound (3-1-6) (4.00 g, 9.4 mmol) was subjected to atmospheric hydrogenation reaction at room temperature for 2.5 hours in ethyl acetate (100 mL) over 5% rhodium carbon (1.91 g, 10 mol %). The catalyst was filtered off. The filtrate was concentrated under reduced pressure. The obtained concentrated residue was purified by silica gel column chromatography (n-hexane:ethyl acetate=4:1) to obtain the title compound (3-1-7) (3.88 g, 97%).

Compound (RE3)

A 10% hydrochloric acid-methanol solution (20 mL) was added at room temperature to a solution of the compound (3-1-7) (3.88 g, 9.1 mmol) in methanol (5 mL), and the reaction mixture was stirred at room temperature for 5 hours. The solvent was distilled off under reduced pressure. The obtained concentrated residue was solidified by the addition of a small amount of 2-propanol and triturated with diethyl ether. The precipitate was collected by filtration and washed with diethyl ether to obtain the compound (RE3) of interest (2.45 g, 74%).
Production Method 3

[Formula 25]

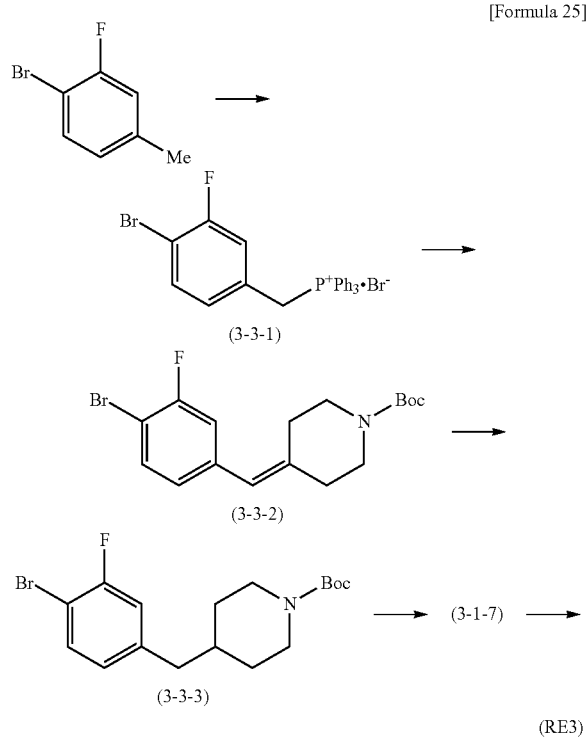

Compound (3-3-1): (4-Bromo-3-fluorobenzyl)(triphenyl)phosphonium bromide

A solution of 4-bromo-3-fluorotoluene (25.0 g, 132 mmol), 5,5-dimethyl-1,3-dibromohydantoin (18.9 g, 66.1 mmol), and azobisisobutyronitrile (1.09 g, 6.64 mmol) in chlorobenzene (400 mL) was stirred at the solution temperature of 80 to 90° C. for 1 hour. The reaction mixture was cooled in an ice bath. Then, water (200 mL) and sodium thiosulfate (33 g, 132 mmol) were added thereto, and the mixture was stirred. The mixture was separated into aqueous and organic layers. The organic layer was washed with water (200 mL), then dried over anhydrous sodium sulfate, and then concentrated until the whole volume reached approximately 100 mL. Triphenylphosphine (34.69 g, 132 mmol) and chlorobenzene (30 mL) were added thereto, and the mixture was heated under reflux for 3 hours. The reaction mixture was cooled to room temperature. Then, the precipitate was collected by filtration, washed with toluene and then dried under reduced pressure to obtain the title compound (3-3-1) (47.0 g).

Compound (3-3-2): tert-Butyl 4-[(4-bromo-3-fluorophenyl)methylidene]piperidine-1-carboxylate A solution of the compound (3-3-1) (15.0 g, 28.3 mmol), 1-tert-Butoxycarbonyl-4-piperidone (3.76 g, 18.9 mmol), and potassium carbonate (5.21 g, 37.7 mmol) in 2-propanol (28 mL) was heated under reflux for 3 hours. The reaction mixture was cooled to room temperature, and the salt was filtered off. Then, toluene (300 mL) was added to the filtrate. The organic layer was washed with water (100 mL) and brine (100 mL). After drying over anhydrous magnesium sulfate, the solvent was distilled off under reduced pressure. n-Hexane (107 mL) was added to the concentrated residue, and the mixture was heated under reflux for 1 hour. Then, the mixture was cooled to room temperature and stirred for 1 hour. Then, the mixture was stirred for 1 hour with cooling in an ice bath. The deposited triphenylphosphine oxide was separated by filtration and washed with n-hexane. Then, the filtrate was concentrated under reduced pressure to obtain the title compound (3-3-2) (8.08 g) as a yellow solid.

Compound (3-3-3): tert-Butyl 4-(4-bromo-3-fluorobenzyl)piperidine-1-carboxylate

The compound (3-3-2) (8.08 g) was subjected to atmospheric hydrogenation reaction for hours in ethyl acetate (57 mL) over 5% platinum carbon (800 mg). The catalyst was filtered off through celite. The filtrate was concentrated to obtain the title compound (3-3-3) (8.61 g) as a pale yellow solid.

Compound (3-1-7)

Potassium t-butoxide (4.23 g, 37.7 mmol) was added at room temperature to a solution of the compound (3-3-3) (8.61 g, which corresponds to 18.9 mmol) and 2-methoxyethanol (2.98 mL, 37.7 mmol) in N-methyl-2-pyrrolidinone (38 mL), and the reaction mixture was stirred at the solution temperature of 90° C. for 2.5 hours. Then, potassium t-butoxide (1.06 g, 9.43 mmol) was added thereto, and the mixture was stirred at 90° C. for 30 minutes. Potassium t-butoxide (1.06 g, 9.43 mmol) was further added thereto, and the mixture was stirred at 90° C. for 30 minutes. The reaction mixture was cooled in an ice bath, and an aqueous saturated ammonium chloride solution (80 mL) was added thereto, followed by extraction with toluene (80 mL×3). The combined organic layers were washed with water (40 mL×2) and brine (40 mL) and dried over anhydrous magnesium sulfate, and the solvent was then distilled off under reduced pressure. n-Hexane (162 mL) was added to the concentrated residue, and the mixture was heated to 60° C. The dissolution thereof was confirmed, and the solution was then gradually cooled to room temperature and stirred overnight at room temperature. Then, the mixture was cooled in an ice bath and stirred for 1 hour. The deposit was collected by filtration, washed with n-hexane and then dried under reduced pressure to obtain the title compound (3-1-7) (6.34 g) as a light brown powder.

Compound (RE3)

A 10% hydrochloric acid-methanol solution (24 mL) was added at room temperature to a solution of the compound (3-1-7) (6.00 g, 14.0 mmol) in methanol (24 mL), and the reaction mixture was stirred at 50° C. for 5 hours. After cooling to room temperature, the solvent was distilled off under reduced pressure. To the concentrated residue, acetonitrile (6 mL) was added, and concentration under reduced pressure was repeated 4 times. Acetonitrile (38 mL) was added to the concentrated residue, and the mixture was heated in an oil bath at 80° C. The dissolution of the solid matter was confirmed, and the solution was then cooled to room temperature over 1 hour. The solution was cooled in an ice bath and stirred at 20° C. for 1 hour and then in an ice bath for 1 hour. Then, the precipitate was collected by filtration, washed with cold acetonitrile (30 mL), and dried under reduced pressure to obtain the title compound (RE3) (4.56 g, 89%) as a white powder.

Reference Example 4

4-[4-Chloro-3-(2-methoxyethoxy)benzyl]piperidine, compound (RE4)

The compound was synthesized according to the following production method:

Production Method

[Formula 26]

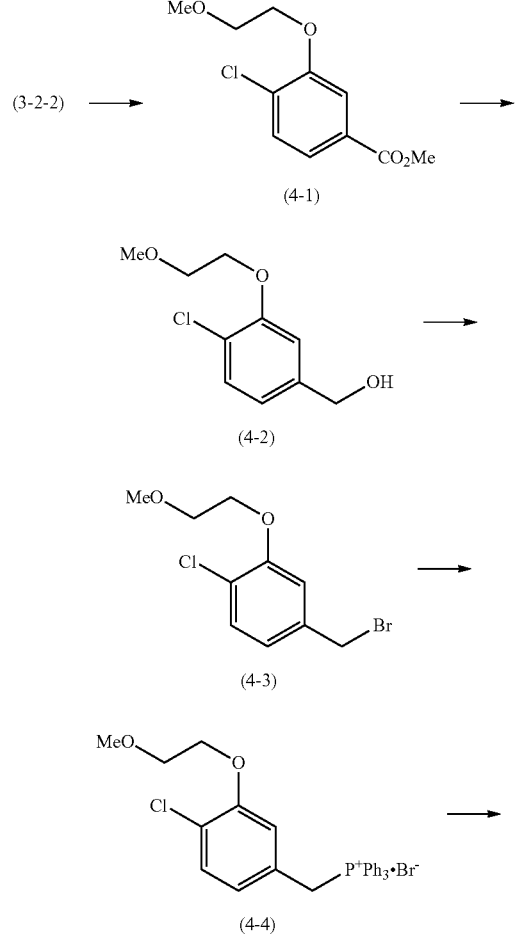

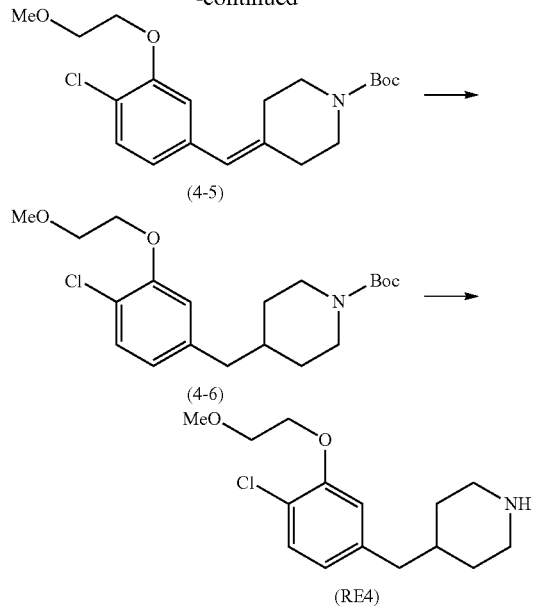

Compound (4-1): Methyl 4-chloro-3-(2-methoxyethoxy)benzoate

A solution of the compound (3-2-2) (5.20 g, 23 mmol) in concentrated hydrochloric acid (36%, 50 mL) was cooled in an ice bath. A solution of sodium nitrite (1.59 g, 23 mmol) in water (20 mL) was added dropwise thereto over 10 minutes, and the reaction mixture was stirred for 20 minutes. This solution kept at 5° C. or lower was added dropwise over 10 minutes to a solution of copper(I) chloride (1.51 g, 15 mmol) in concentrated hydrochloric acid (36%, 50 mL) warmed to 60° C., and the reaction mixture was stirred at 60° C. for 50 minutes. The mixture was cooled to room temperature and then diluted with water, followed by extraction with diethyl ether. The organic layer was washed with an aqueous saturated sodium bicarbonate solution and brine in this order and dried over anhydrous magnesium sulfate, and the solvent was then distilled off under reduced pressure. The obtained concentrated residue was purified by silica gel column chromatography (n-hexane:ethyl acetate=4:1→1:1) to obtain the title compound (4-1) (4.43 g, 78%) as a white solid.

Compound (4-2): [4-Chloro-3-(2-methoxyethoxy)phenyl]methanol

A 1.0 M solution of borane/tetrahydrofuran complex in tetrahydrofuran (106 mL, 106 mmol) was added dropwise at room temperature to a solution of the compound (4-1) (4.33 g, 18 mmol) in anhydrous tetrahydrofuran (50 mL), and the reaction mixture was subsequently heated under reflux for 27.5 hours. After cooling to room temperature, methanol was added thereto until the gas evolution ceased. The solvent was distilled off under reduced pressure. The obtained concentrated residue was purified by silica gel column chromatography (n-hexane:ethyl acetate=3:1→1:1) to obtain the title compound (4-2) (3.62 g, 94%).

Compound (4-3): 4-(Bromomethyl)-1-chloro-2-(2-methoxyethoxy)benzene

Triphenylphosphine (6.54 g, 25 mmol) and carbon tetrabromide (8.26 g, 25 mmol) were simultaneously added at room temperature to a solution of the compound (4-2) (3.60 g, 16.6 mmol) in diethyl ether (50 mL), and the reaction mixture was stirred for 16 hours. The precipitate was separated by filtration. The filtrate was concentrated under reduced pressure. The obtained concentrated residue was purified by silica gel column chromatography (n-hexane-→n-hexane:ethyl acetate=7:1) to obtain the title compound (4-3) (3.93 g, 85%) as a colorless oil.

Compound (4-4): [4-Chloro-3-(2-methoxyethoxy)benzyl](triphenyl)phosphonium bromide A solution of the compound (4-3) (3.90 g, 14 mmol) and triphenylphosphine (4.41 g, 36.17 mmol) in toluene (100 mL) was heated under reflux for 5 hours. The reaction mixture was gradually cooled to room temperature and subsequently stirred for 1 hour in an ice bath. Then, the precipitate was collected by filtration, washed with toluene, and dried under reduced pressure to obtain the title compound (4-4) (7.24 g, 95%) as a white powder.

Compound (4-5): tert-Butyl 4-{[4-chloro-3-(2-methoxyethoxy)phenyl]methylidene}piperidine-1-carboxylate A suspension of the compound (4-4) (7.24 g, 13 mmol), 1-tert-butoxycarbonyl-4-piperidone (2.40 g, 12 mmol), and potassium carbonate (2.78 g, 20 mmol) in 2-propanol (100 mL) was heated under reflux for 8 hours. The reaction mixture was stirred for 1 hours with ice cooling. Then, the deposit was filtered off. The filtrate was concentrated under reduced pressure. The obtained concentrated residue was purified by silica gel column chromatography (n-hexane:ethyl acetate=10:1→8:1) to obtain the title compound (4-5) (4.52 g, quantitative) as a colorless oil.

Compound (4-6): tert-Butyl 4-[4-chloro-3-(2-methoxyethoxy)benzyl]piperidine-1-carboxylate The compound (4-5) (4.52 g, 12 mmol) was subjected to atmospheric hydrogenation reaction at room temperature for 1.5 hours in ethyl acetate (200 mL) over 5% rhodium carbon (1.53 g). The catalyst was filtered off through celite. The filtrate was concentrated under reduced pressure. Then, the obtained concentrated residue was purified by silica gel column chromatography (n-hexane:ethyl acetate=8:1→4:1) to obtain the title compound (4-6) (4.34 g, 96%).

Compound (RE4)

A solution of the compound (4-6) (4.34 g, 11 mmol) in 1,4-dioxane (50 mL) was added to a 4 N hydrochloric acid-1,4-dioxane solution (50 mL), and the reaction mixture was stirred at room temperature for 15.5 hours. The solvent was distilled off under reduced pressure to obtain a hydrochloride of the title compound (3.24 g, 90%). A 2 g aliquot thereof was added to a 2 N aqueous sodium hydroxide solution, followed by extraction with chloroform. The organic layer was dried over anhydrous sodium sulfate, and the solvent was then concentrated under reduced pressure to obtain the compound (RE4) of interest (1.91 g) as a pale yellow oil.

Retention time (Condition 1): 13.71 minutes $^1$H-NMR (300 MHz, CDCl$_3$) δ: 1.03-1.26 (2H, m), 1.48-1.69 (3H, m), 2.48 (2H, t, J=5.2 Hz), 2.54 (2H, td, J=12.5, 2.6 Hz), 3.06 (2H, br d, J=11.9 Hz), 3.49 (3H, s), 3.80 (2H, t, J=4.8 Hz), 4.17 (2H, t, J=4.8 Hz), 6.69 (1H, dd, J=7.9, 1.8 Hz), 6.73 (1H, d, J=1.8 Hz), 7.26 (1H, d, J=8.1 Hz).

Reference Example 5

(2-[2-Bromo-5-(piperidin-4-ylmethyl)phenoxy]ethanol, compound (RE5)

[Formula 27]

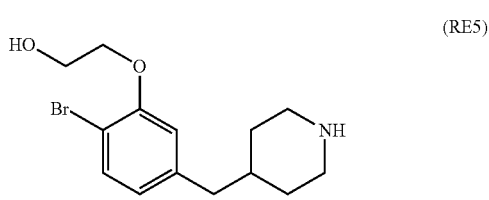

(RE5)

A solution of the compound (RE3) (3.00 g, 8.3 mmol) in dichloromethane (100 mL) was cooled in a salt-ice bath. A 1 M boron tribromide-dichloromethane solution (7.8 mL, 7.8 mmol) was added dropwise thereto at 0° C. over 30 minutes, and the reaction mixture was stirred for 1.5 hours with ice cooling. Methanol (20 mL) was added thereto, and the solvent was distilled off under reduced pressure. A 5% aqueous potassium carbonate solution (50 mL) was added to the obtained concentrated residue, followed by extraction with chloroform. The organic layer was dried over anhydrous sodium sulfate. The solvent was distilled off under reduced pressure to obtain the title compound (RE5) (3.03 g, quantitative).

Retention time (Condition 1): 7.56 minutes $^1$H-NMR (400 MHz, CDCl$_3$) δ: 1.15-1.30 (2H, m), 1.40-1.55 (1H, m), 1.55-1.70 (2H, m), 2.49 (2H, d, J=6.7 Hz), 2.58 (2H, dt, J=2.4, 12 Hz), 3.11 (2H, d like, J=12 Hz), 3.98 (2H, t, J=4.6 Hz), 4.14 (2H, t, J=4.6 Hz), 6.66 (1H, dd, J=8.0, 1.8 Hz), 6.70 (1H, d, J=1.8 Hz), 7.42 (1H, d, J=8.0 Hz).

Reference Example 6

4-[3-(2-Methoxyethoxy)-4-methylbenzyl]piperidine, compound (RE6)

The compound was synthesized according to the following production method:

Production Method (3-1-7) ⟶

[Formula 28]

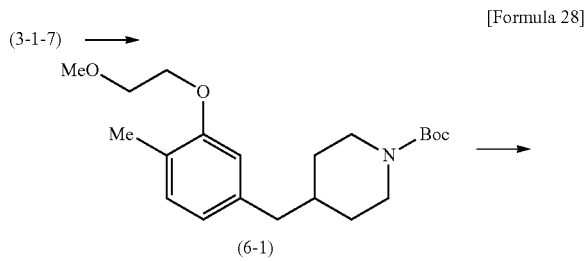

(6-1)

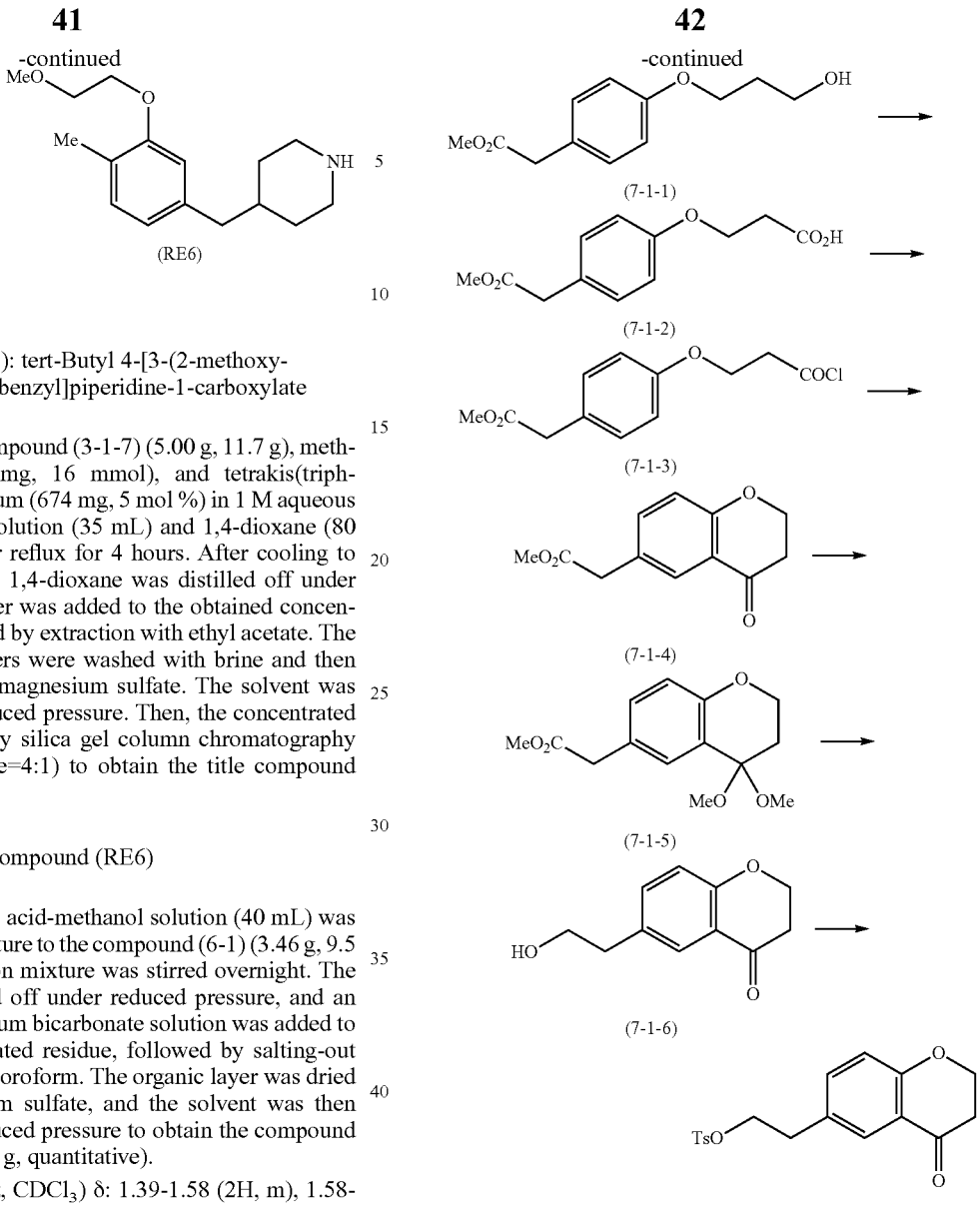

Compound (6-1): tert-Butyl 4-[3-(2-methoxyethoxy)-4-methylbenzyl]piperidine-1-carboxylate A solution of the compound (3-1-7) (5.00 g, 11.7 g), methylboronic acid (978 mg, 16 mmol), and tetrakis(triphenylphosphine)palladium (674 mg, 5 mol %) in 1 M aqueous potassium carbonate solution (35 mL) and 1,4-dioxane (80 mL) was heated under reflux for 4 hours. After cooling to room temperature, the 1,4-dioxane was distilled off under reduced pressure. Water was added to the obtained concentrated residue, followed by extraction with ethyl acetate. The combined organic layers were washed with brine and then dried over anhydrous magnesium sulfate. The solvent was distilled off under reduced pressure. Then, the concentrated residue was purified by silica gel column chromatography (n-hexane:ethyl acetate=4:1) to obtain the title compound (6-1) (3.46 g, 82%).

Compound (RE6)

A 10% hydrochloric acid-methanol solution (40 mL) was added at room temperature to the compound (6-1) (3.46 g, 9.5 mmol), and the reaction mixture was stirred overnight. The methanol was distilled off under reduced pressure, and an aqueous saturated sodium bicarbonate solution was added to the obtained concentrated residue, followed by salting-out and extraction with chloroform. The organic layer was dried over anhydrous sodium sulfate, and the solvent was then distilled off under reduced pressure to obtain the compound (RE6) of interest (2.56 g, quantitative).

$^1$H-NMR (300 MHz, CDCl$_3$) δ: 1.39-1.58 (2H, m), 1.58-1.74 (1H, m), 1.77 (2H, d like, J=13.9 Hz), 2.20 (3H, s), 2.52 (2H, d, J=7.1 Hz), 2.70 (2H, t like, J=12.6 Hz), 3.33 (2H, d like, J=12.4 Hz), 3.47 (3H, s), 3.77 (2H, t, J=4.8 Hz), 4.10 (2H, t, J=4.8 Hz), 6.59 (1H, s), 6.63 (1H, d, J=7.6 Hz), 7.03 (1H, d, J=7.6 Hz).

Reference Example 7

(2-(4-Oxo-3,4-dihydro-2H-chromen-6-yl)ethyl 4-methylbenzenesulfonate, compound (RE7)

The compound was synthesized according to the following Production Method 1, 2, or 3:

Production Method 1

[Formula 29]

Compound (7-1-1): Methyl [4-(3-hydroxypropoxy)phenyl]acetate

Potassium carbonate (91.5 g, 662 mmol) and 3-bromo-1-propanol (35.3 mL, 391 mmol) were added in this order at room temperature to a solution of 4-hydroxyphenylacetic acid methyl ester (50.0 g, 301 mmol) in acetonitrile (1000 mL) and water (10 mL), and the reaction mixture was heated under reflux for 3 hours. After cooling to room temperature, the salt was filtered off, and the residue on the filter was washed with acetonitrile (50 mL×2). The filtrate was concentrated under reduced pressure, and the obtained concentrated residue was separated into aqueous and organic layers by addition of toluene (500 mL) and water (250 mL). The aqueous layer was extracted with toluene (125 mL×2). The combined organic layers were washed with a 0.5 N aqueous sodium hydroxide solution (100 mL) and a 1% aqueous potassium bisulfate solution (100 mL). The organic layer was dried over anhydrous magnesium sulfate, and the solvent was then distilled off under reduced pressure to obtain the title compound (7-1-1) (70.2 g) as a yellow oil.

Compound (7-1-2): 3-[4-(2-Methoxy-2-oxoethyl)phenoxy]propanoic acid

A 0.25 M aqueous potassium dihydrogen phosphate solution (400 mL), a 0.25 M aqueous disodium hydrogen phosphate solution (400 mL), 80% sodium chlorite (54.5 g, 482 mmol), and a 5% aqueous sodium hypochlorite solution (6.52 mL, 4.82 mmol) were added in this order to a solution of a 2,2,6,6-tetramethyl-1-piperidinyloxy radical (TEMPO) (4.71 g, 30.1 mmol) in acetonitrile (160 mL). Subsequently, a solution of the compound (7-1-1) (56.2 g, which corresponds to 241 mmol) in acetonitrile (800 mL) was added dropwise thereto over approximately 1 hour with the solution temperature kept at 20 to 25° C. by water cooling. The reaction mixture was stirred at this temperature for 2 hours. Then, a 20% aqueous sodium bisulfite solution (400 mL) was added dropwise thereto over 30 minutes with the solution temperature kept at 15° C. or lower by ice cooling. The solution was gradually warmed to room temperature, and the acetonitrile was distilled off under reduced pressure. Water (400 mL) was added thereto, and the mixture was stirred at room temperature for 30 minutes. The resulting precipitate was collected by filtration and washed with water (100 mL×2). The precipitate on the filter was dissolved in ethyl acetate (400 mL), then washed with brine (100 mL), and dried over anhydrous sodium sulfate, and the solvent was then distilled off under reduced pressure to obtain the title compound (7-1-2) (47.87 g).

Compound (7-1-3): Methyl [4-(3-chloro-3-oxopropoxy)phenyl]acetate

Thionyl chloride (42.7 mL, 592 mmol) was added at room temperature to a solution of the compound (7-1-2) (47.0 g, 197 mmol) in toluene (470 mL), and the reaction mixture was stirred at 60° C. for 3 hours. After cooling to room temperature, the toluene was distilled off to obtain the title compound (7-1-3) (56.52 g) as a pale yellow oil.

Compound (7-1-4): Methyl (4-oxo-3,4-dihydro-2H-chromen-6-yl)acetate

A solution of the compound (7-1-3) (56.52 g, which corresponds to 197 mmol) in dichloromethane (140 mL) was added dropwise over 30 minutes to a solution of aluminum chloride (52.5 g, 394 mmol) in dichloromethane (330 mL) with the solution temperature kept at 20 to 25° C. by water cooling, and the reaction mixture was stirred at this temperature for 1.5 hours. The reaction mixture was cooled, and a 2 N aqueous hydrochloric acid solution (470 mL) was added thereto with the solution temperature kept at 15° C. or lower by cooling in an ice bath. The mixture was warmed to room temperature and then separated into aqueous and organic layers. The aqueous layer was extracted with chloroform (120 mL). The combined organic layers were washed with water (240 mL) and an aqueous saturated sodium bicarbonate solution (240 mL) in this order and dried over anhydrous magnesium sulfate, and the solvent was then distilled off under reduced pressure to obtain the title compound (7-1-4) (38.91 g) as a brown solid.

Compound (7-1-5): Methyl (4,4-dimethoxy-3,4-dihydro-2H-chromen-6-yl)acetate p-Toluenesulfonic acid monohydrate (3.02 g, 15.9 mmol) and Methyl orthoformate (210 mL) were added to a solution of the compound (7-1-4) (35.0 g, 159 mmol) in methanol (105 mL), and the reaction mixture was stirred at room temperature (15 to 20° C.) for 20 hours. The reaction solution was added dropwise over 15 minutes to a 5% aqueous sodium bicarbonate solution (175 mL) with the solution temperature kept at 15° C. or lower by ice cooling, and the mixture was separated into aqueous and organic layers by the addition of toluene (175 mL) and water (88 mL). The aqueous layer was extracted with toluene (88 mL). The combined organic layers were washed with water (44 mL) and then dried over anhydrous sodium sulfate. The solvent was distilled off to obtain the title compound (7-1-5) (46.49 g) as a yellow oil.

Compound (7-1-6): 6-(2-Hydroxyethyl)-2,3-dihydro-4H-chromen-4-one

A solution of the compound (7-1-5) (46.0 g, which corresponds to 159 mmol) in tetrahydrofuran (90 mL) was added dropwise over 30 minutes to a suspension of lithium aluminum hydride (9.05 g, 239 mmol) in tetrahydrofuran (600 mL) with the solution temperature kept at 30° C. or lower by water cooling, and the reaction mixture was stirred at this temperature for 1 hour. Tetrahydrofuran-water (1:2, 12 mL) was added dropwise thereto with the solution temperature kept at 15° C. or lower by ice cooling (during which insoluble matter was deposited and made stirring difficult). Subsequently, a 3 N aqueous hydrochloric acid solution (460 mL) was added dropwise thereto with the solution temperature kept at 15° C. or lower. The mixture was directly stirred at 20 to 25° C. for 1.5 hours and separated into aqueous and organic layers by the addition of toluene (460 mL). The aqueous layer was extracted with toluene (230 mL). The combined organic layers were washed with a 3 N aqueous hydrochloric acid solution (230 mL×2) and dried over anhydrous magnesium sulfate, and the solvent was then distilled off under reduced pressure to obtain the title compound (7-1-6) (30.0 g) as a colorless oil.

Compound (RE7)

Trimethylamine hydrochloride (497 mg, 5.20 mmol) and triethylamine (14.4 mL, 104 mmol) were added to a solution of the compound (7-1-6) (10.0 g, which corresponds to 52 mmol) in acetonitrile (150 mL). p-Toluenesulfonyl chloride (11.9 g, 62.4 mmol) was added thereto in small portions at the solution temperature of 15° C. or lower by cooling in an ice bath, and the reaction mixture was stirred at the solution temperature of 5° C. or lower for 1.5 hours. A 5% aqueous sodium bicarbonate solution (75 mL) was added thereto at the solution temperature of 10° C. or lower, and the mixture was heated to room temperature and then separated into aqueous and organic layers by the addition of toluene (75 mL). The aqueous layer was extracted with toluene (75 mL). The combined organic layers were washed with a 1% aqueous potassium bisulfate solution (38 mL×2) and dried over anhydrous magnesium sulfate, and the solvent was then distilled off under reduced pressure to obtain a concentrated residue (16.61 g). Toluene (50 mL) was added thereto, and the mixture was stirred at 50° C. for 1.5 hours and subsequently cooled to room temperature (20 to 25° C.) over 30 minutes. The mixture was stirred at the solution temperature of 20 to 25° C. for 1 hour by water cooling. Then, the precipitate was collected by filtration, then washed with toluene (10 mL×2), and dried under reduced pressure to obtain the compound (RE7) of interest (10.65 g) as a pale yellow powder.

Retention time (Condition 2): 15.50 minutes

Melting point: 121-122° C.

¹H-NMR (300 MHz, CDCl₃) δ: 2.44 (3H, s), 2.79 (2H, t, J=6.5 Hz), 2.91 (2H, t, J=6.9 Hz), 4.18 (2H, t, J=6.9 Hz), 4.51 (2H, t, J=6.4 Hz), 6.88 (1H, d, J=8.4 Hz), 7.26 (1H, dd, J=8.5, 2.5 Hz), 7.30 (2H, d, J=8.5 Hz), 7.60 (1H, d, J=2.2 Hz), 7.71 (2H, d, J=8.3 Hz).

Production Method 2

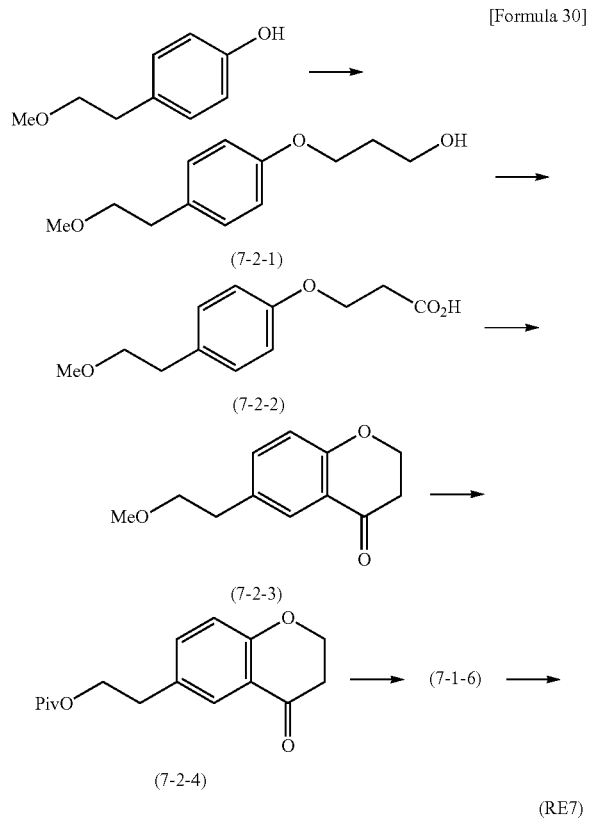

[Formula 30]

Compound (7-2-1): 3-[4-(2-Methoxyethyl)phenoxy]propan-1-ol

A solution of 4-(2-Methoxyethyl)phenol (1.00 g, 6.57 mmol), 3-Bromo-1-propanol (771 μL, 8.54 mmol), potassium carbonate (2.00 g, 14.5 mmol), and water (200 μL) in acetonitrile (20 mL) was heated under reflux for 3 hours. After cooling to room temperature, the salt was separated by filtration. The filtrate was concentrated under reduced pressure. The obtained concentrated residue was separated into aqueous and organic layers by the addition of water (5 mL) and toluene (5 mL). The aqueous layer was extracted with toluene (5 mL×2). The combined organic layers were washed with a 0.5 N aqueous sodium hydroxide solution (2 mL) and 1% potassium bisulfate (2 mL) and dried over anhydrous sodium sulfate, and the solvent was then distilled off under reduced pressure to obtain the title compound (7-2-1) (1.56 g).

Compound (7-2-2): 3-[4-(2-Methoxyethyl)phenoxy]propanoic acid

The title compound (7-2-2) (1.30 g, 88%) was obtained as a white powder using the compound (7-2-1) (1.56 g, which corresponds to 6.57 mmol) in the same way as in Example (7-1-2).

Compound (7-2-3): 6-(2-Methoxyethyl)-2,3-dihydro-4H-chromen-4-one

Thionyl chloride (1.25 mL) was added at room temperature to a solution of the compound (7-2-2) (1.30 g, 5.80 mmol) in toluene (13 mL), and the reaction mixture was stirred at 60° C. for 3 hours. After cooling to room temperature, the solvent was distilled off under reduced pressure to obtain acid chloride (1.46 g). A solution of a 292 mg (which corresponds to 1.16 mmol) aliquot thereof in dichloromethane (1 mL) was added dropwise at room temperature over 5 minutes to a suspension of aluminum chloride (309 mg, 2.32 mmol) in dichloromethane (2 mL) with water cooling, and the reaction mixture was stirred for 1 hour. The reaction solution was poured into a 2 N aqueous hydrochloric acid solution (3 mL) and ice, followed by extraction with toluene. The organic layer was washed with water, an aqueous saturated sodium bicarbonate solution, and brine in this order and dried over anhydrous sodium sulfate, and the solvent was then distilled off under reduced pressure to obtain the title compound (7-2-3) (235 mg).

Compound (7-2-4): 2-(4-Oxo-3,4-dihydro-2H-chromen-6-yl)ethyl 2,2-dimethylpropanoate Pivaloyl chloride (298 μL, 2.43 mmol) was added at 40° C. to a solution of the compound (7-2-3) (100 mg, 0.485 mmol), sodium iodide (436 mg, 2.91 mmol), and water (3 μL) in acetonitrile (0.6 mL), and the reaction mixture was stirred at 40° C. for 1.5 hours. The mixture was cooled to room temperature, then diluted with toluene, and separated into aqueous and organic layers by the addition of water. The aqueous layer was extracted with toluene. The combined organic layers were washed with an aqueous saturated sodium bicarbonate solution and brine in this order and dried over anhydrous sodium sulfate, and the solvent was then distilled off under reduced pressure to obtain the title compound (7-2-4) (148 mg) as a brown oil.

Compound (7-1-6)

A solution of the compound (7-2-4) (105 mg, 0.354 mmol) in concentrated hydrochloric acid (36%, 2 mL) and methanol (1 mL) was stirred at 50° C. for 3 hours. The reaction mixture was cooled to room temperature and then poured into ice, followed by extraction with toluene. The organic layer was washed with an aqueous saturated sodium bicarbonate solution and brine. The organic layer was dried over anhydrous sodium sulfate, and the solvent was then distilled off under reduced pressure to obtain the title compound (7-1-6) (62 mg).

Compound (RE7)

p-Toluenesulfonyl chloride (81 mg, 0.43 mmol) was added to a solution of the compound (7-1-6) (62 mg, 0.354 mmol), trimethylamine hydrochloride (3.4 mg, 0.035 mmol), and triethylamine (98 μL) in dichloromethane (1 mL) with cooling in an ice bath, and the reaction mixture was stirred at this temperature for 1.5 hours. An aqueous saturated sodium bicarbonate solution was added thereto, and the mixture was warmed to room temperature, followed by extraction with toluene. The combined organic layers were washed with a 1% aqueous potassium bisulfate solution and brine and then dried over anhydrous sodium sulfate. The solvent was distilled off under reduced pressure. Then, toluene (1 mL) was added to the obtained concentrated residue, and the mixture was stirred at 50° C. for 1 hour. The mixture was gradually cooled to room temperature, while it was stirred. Then, the mixture was stirred at room temperature for 2 hours. The precipitate was collected by filtration, washed with toluene, and then dried under reduced pressure to obtain the compound (RE7) of interest (35 mg, 29%).

Production Method 3

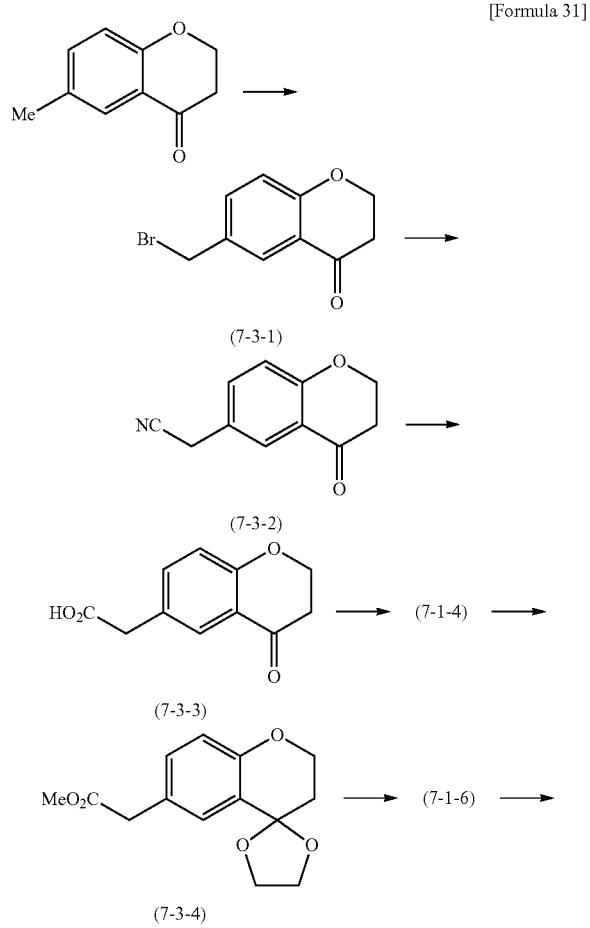

(RE7)

Compound (7-3-1): 6-(Bromomethyl)-2,3-dihydro-4H-chromen-4-one

A solution of 6-Methyl-2,3-dihydro-4H-chromen-4-one (7.2 g, 44 mmol), 5,5-Dimethyl-1,3-dibromohydantoin (7.7 g, 27 mmol), and Azobisisobutyronitrile (1.5 g, 9 mmol) in monochlorobenzene (140 mL) was stirred at 80° C. for 3 hours. The reaction solution was poured into ice water (100 mL), and the mixture was warmed to room temperature and then separated into aqueous and organic layers. The aqueous layer was extracted with dichloromethane (50 mL×2). The combined organic layers were washed with brine. The organic layer was dried over anhydrous magnesium sulfate, and the solvent was then distilled off under reduced pressure. The obtained concentrated residue was purified by silica gel column chromatography (n-hexane/ethyl acetate) to obtain the title compound (7.8 g, 73%).

Compound (7-3-2): (4-Oxo-3,4-dihydro-2H-chromen-6-yl)acetonitrile

A solution of the compound (7-3-1) (500 mg, 2.1 mmol) and potassium cyanide (135 mg, 2.1 mmol) in 1,4-dioxane (7.5 mL) and water (2.5 mL) was stirred at 50° C. for 3 hours. The reaction solution was cooled to room temperature, and brine (30 mL) was then added thereto, followed by extraction with toluene (30 mL×2). The combined organic layers were dried over anhydrous magnesium sulfate, and the solvent was then distilled off under reduced pressure. The obtained concentrated residue was purified by silica gel column chromatography (n-hexane/ethyl acetate) to obtain the title compound (311 mg, 70%).

Compound (7-1-4)

A solution of the compound (7-3-2) (276 mg, 1.5 mmol) in concentrated sulfuric acid (2 mL), acetic acid (2 mL), and water (2 mL) was stirred at 80° C. for 5 hours. The reaction solution was cooled to room temperature and then adjusted to pH 10 to 11 with a 10% aqueous sodium hydroxide solution, followed by extraction with dichloromethane (30 mL×2). The combined organic layers were washed with brine and then dried over anhydrous magnesium sulfate, and the solvent was distilled off under reduced pressure to obtain a crude product of the compound (7-3-3) (4-oxo-3,4-dihydro-2H-chromen-6-yl)acetic acid. This crude product was dissolved together with concentrated sulfuric acid (0.05 mL) in methanol (5 mL) without further purification, and the reaction mixture was heated under reflux for 2 hours. After cooling to room temperature, water (10 mL) was added thereto, and the methanol was distilled off under reduced pressure. The concentrated residue was subjected to extraction with ethyl acetate (30 mL×2). The combined organic layers were washed with brine and dried over anhydrous magnesium sulfate, and the solvent was then distilled off under reduced pressure. The obtained concentrated residue was purified by silica gel column chromatography (n-hexane/ethyl acetate) to obtain the title compound (251 mg, 88%).

Compound (7-3-4): Methyl 2,3-dihydrospiro[chromene-4,2'-[1,3]dioxolan]-6-ylacetate A solution of the compound (7-1-4) (419 mg, 1.9 mmol), ethylene glycol (0.21 mL, 3.8 mmol), Methyl orthoformate (0.42 mL, 3.8 mmol), and p-Toluenesulfonic acid monohydrate (72 mg, 0.38 mmol) in toluene (8 mL) was heated under reflux for 3 hours. After cooling to room temperature, toluene (10 mL) was added thereto, and the mixed solution was washed with an aqueous saturated sodium bicarbonate solution (10 mL), water, and brine in this order. The organic layer was dried over anhydrous magnesium sulfate, and the solvent was then distilled off under reduced pressure to obtain a crude product of the title compound (502 mg).

Compound (7-1-6)

A solution of the compound (7-3-4) (502 mg) in tetrahydrofuran (3 mL) was added dropwise at 0° C. to a suspension of lithium aluminum hydride (72 mg, 1.9 mmol) in tetrahydrofuran (5 mL). The reaction mixture was gradually warmed to room temperature, while it was stirred for 1 hour. Diethyl ether (8 mL) and water were added thereto, and the resulting precipitate was separated by filtration. The solvent in the filtrate was distilled off under reduced pressure. A 10% aqueous hydrochloric acid solution (8 mL) and tetrahydrofuran (8 mL) were added to the obtained concentrated residue, and the mixed solution was stirred at room temperature for 30 minutes. The tetrahydrofuran was distilled off under reduced pressure, followed by extraction with ethyl acetate. The organic layer was distilled off under reduced pressure with brine and then dried over anhydrous magnesium sulfate, and the solvent was distilled off under reduced pressure. The obtained concentrated residue was purified by silica gel column chromatography (n-hexane/ethyl acetate) to obtain the title compound (254 mg, 69%).

Compound (RE7)

The compound (RE7) was obtained in the same way as in Production Method 1 in Reference Example 7 using the compound (7-1-6).

Reference Example 8

2-(8-Oxo-5,6,7,8-tetrahydronaphthalen-2-yl)ethyl 4-methylbenzenesulfonate, compound (RE8)

The compound was synthesized according to the following production method:
Production Method

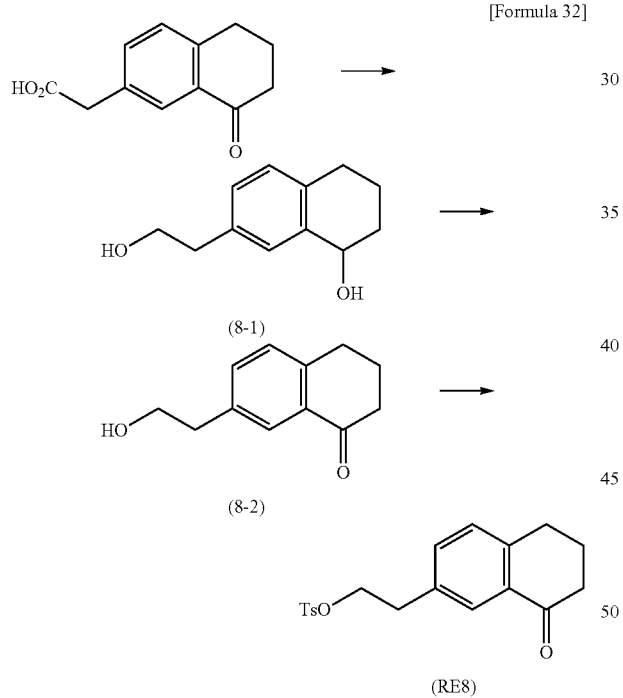

Compound (8-1): 7-(2-Hydroxyethyl)-1,2,3,4-tetrahydronaphthalen-1-ol

A solution of (8-Oxo-5,6,7,8-tetrahydronaphthalen-2-yl) acetic acid (50 mg, 0.25 mmol) synthesized according to a method described in the document (J. Med. Chem. 1994, 37 (21), 3485) in anhydrous tetrahydrofuran (1 mL) was added to a suspension of lithium aluminum hydride (33 mg, 0.86 mmol) in anhydrous tetrahydrofuran (2 mL) under heating to reflux, and the reaction mixture was heated under reflux for 1 hour. The reaction solution was cooled to room temperature and then cooled in an ice bath, and water (32 µL) was added thereto. Subsequently, a 15% aqueous sodium hydroxide solution (32 µL) and water (96 µL) were added thereto, and the solution was stirred at this temperature for 30 minutes. The resulting precipitate was filtered off. The filtrate was concentrated to obtain the title compound (8-1) (45 mg, 95%).

Compound (8-2): 7-(2-Hydroxyethyl)-3,4-dihydronaphthalen-1(2H)-one

A suspension of the compound (8-1) (45 mg, 0.23 mmol) and manganese dioxide (20 mg, 2.3 mmol) in dichloromethane (2 mL) was stirred at room temperature for 5 days. The manganese dioxide was filtered off. The filtrate was concentrated under reduced pressure. The obtained concentrated residue was purified by silica gel column chromatography (n-hexane:ethyl acetate=2:1) to obtain the title compound (8-2) (28 mg, 63%).

Compound (RE8)

A solution of the compound (8-2) (28 mg, 0.15 mmol), triethylamine (41 µL, 0.29 mmol), and triethylamine hydrochloride (1.4 mg, 0.015 mmol) in dichloromethane (2 mL) was cooled in an ice bath. p-Toluenesulfonyl chloride (42 mg, 0.22 mmol) was added thereto, and the reaction mixture was stirred for 40 minutes with ice cooling. Water (20 mL) was added thereto, followed by extraction with chloroform (40 mL×2). The organic layer was dried over anhydrous magnesium sulfate. The solvent was distilled off under reduced pressure. The obtained concentrated residue was purified by silica gel column chromatography (n-hexane:ethyl acetate=5:1→2:1) to obtain the compound (RE8) of interest (49 mg, 96%).

Retention time (Condition 2): 22.59 minutes
$^1$H-NMR (300 MHz, CDCl$_3$): 7.74 (d, J=2.0 Hz, 1H, Ar), 7.71 (d, J=8.4 Hz, 2H, Ar), 7.32-7.26 (m, 3H, Ar), 7.17 (d, J=7.7 Hz, 1H, Ar), 4.20 (t, J=7.0 Hz, 2H, CH2), 3.00-2.90 (m, 4H), 2.64 (5, J=6.5 Hz, 2H, CH2), 2.44 (s, 3H, CH3), 2.18-2.08 (m, 2H).

Reference Example 9

2-(3-Oxo-2,3-dihydro-1H-inden-5-yl)ethyl 4-methylbenzenesulfonate, compound (RE9)

[Formula 33]

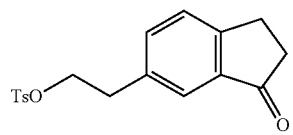

(RE9)

The title compound (RE9) was produced in the same way as in Reference Example 8 using (3-Oxo-2,3-dihydro-1H-inden-5-yl)acetic acid produced according to a method described in the document (J. Med. Chem. 1979, 22 (12), 1464).

$^1$H-NMR (300 MHz, CDCl$_3$) δ: 7.69 (d, J=8.5 Hz, 2H, Ar), 7.44 (s, 1H, Ar), 7.41-7.38 (m, 2H, Ar), 7.28 (d, J=8.5 Hz, 2H,

Ar), 4.22 (t, J=6.8 Hz, 2H, CH2), 3.11 (5, J=6.0 Hz, 2H, CH2), 3.01 (t, J=6.8 Hz, 2H, CH2), 2.69 (t, J=6.0 Hz, 2H, CH2), 2.44 (s, 3H, CH3).

Reference Example 10

2-(5-Oxo-2,3,4,5-tetrahydro-1-benzoxepin-7-yl)ethyl 4-methylbenzenesulfonate, compound (RE10)

[Formula 34]

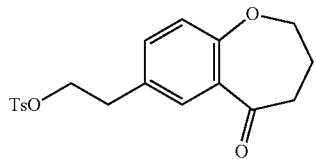

(RE10)

The title compound (RE10) was produced in the same way as in Reference Example 8 using (5-Oxo-2,3,4,5-tetrahydro-1-benzoxepin-7-yl)acetic acid produced according to a method described in the patent document (JP-A-61-236774).

Retention time (Condition 2): 19.93 minutes
$^1$H-NMR (300 MHz, CDCl$_3$) δ: 2.16-2.25 (2H, m), 2.44 (3H, s), 2.81-2.99 (4H, m), 4.13-4.27 (4H, m), 6.98 (1H, d, J=8.3 Hz), 7.21 (1H, dd, J=8.3, 2.3 Hz), 7.30 (2H, d, J=8.1 Hz), 7.48 (1H, d, J=2.4 Hz), 7.72 (2H, d, J=8.3 Hz).

Reference Example 11

(2-(4-Oxo-3,4-dihydro-2H-chromen-6-yl)ethyl benzenesulfonate), compound (RE11)

[Formula 35]

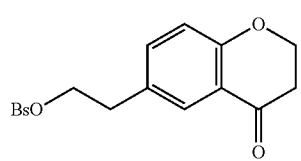

(RE11)

The title compound was obtained in the same way as in Production Method 1 in Reference Example 7 using the compound (7-1-6) and benzenesulfonyl chloride.

$^1$H-NMR (300 MHz, CDCl$_3$) δ: 2.85 (2H, t, J=6.2 Hz), 2.90 (2H, t, J=7.0 Hz), 4.19 (2H, t, J=7.0 Hz), 4.22 (2H, t, J=6.2), 6.79 (2H, d, J=8.6 Hz), 7.01 (2H, d, J=8.6 Hz), 7.45-7.52 (2H, m), 7.57-7.65 (1H, m), 7.75-7.82 (2H, m).

Example 1

(6-(2-{4-[4-Bromo-3-(2-methoxyethoxy)benzyl] piperidin-1-yl}ethyl)-2,3-dihydro-1H-inden-1-one

[Formula 36]

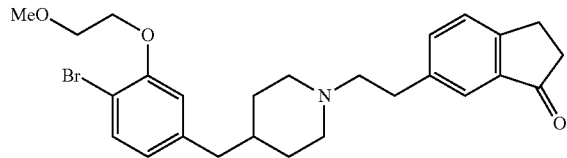

A solution of the compound (RE3) (99 mg, 0.30 mmol), the compound (RE9) (100 mg, 0.30 mmol), and potassium carbonate (0.39 mmol) in acetonitrile (3 mL) was stirred at 60° C. for 27 hours. The reaction mixture was cooled to room temperature, and water (20 mL) was then added thereto, followed by extraction with ethyl acetate (40 mL). The organic layer was dried over anhydrous sodium sulfate, and the solvent was then distilled off under reduced pressure. The obtained concentrated residue was purified by preparative thin-layer silica gel chromatography (chloroform:methanol=10:1) to obtain the title compound (137 mg, 93%) as a pale yellow oil.

Retention time (Condition 1): 27.44 minutes
$^1$H-NMR (300 MHz, CDCl$_3$) δ: 1.33 (2H, m), 1.44-1.71 (3H, m), 1.97 (2H, bt, J=9.9 Hz), 2.49 (2H, d, J=6.8 Hz), 2.58 (2H, bt, J=8.1 Hz), 2.67-2.73 (2H, m), 2.88 (2H, bt, J=8.0 Hz), 2.99 (2H, bd, J=11.2 Hz), 3.11 (2H, t, J=5.9 Hz), 3.50 (3H, s), 3.81 (2H, dd, J=5.3, 4.2 Hz), 4.17 (2H, dd, J=5.3, 4.2 Hz), 6.64 (1H, dd, J=8.1, 1.8 Hz), 6.71 (1H, d, J=1.8 Hz), 7.37-7.47 (3H, m), 7.58 (1H, bs).

Example 2

7-(2-{4-[4-Bromo-3-(2-methoxyethoxy)benzyl]piperidin-1-yl}ethyl)-3,4-dihydronaphthalen-1(2H)-one

[Formula 37]

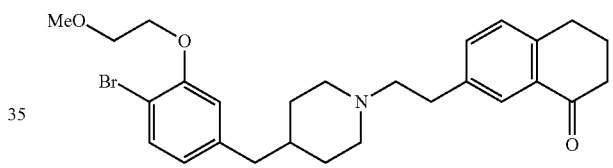

The title compound was synthesized in the same way as in Example 1 using the compound (RE8) instead of the compound (RE9).

Retention time (Condition 1): 31.95 minutes
$^1$H-NMR (400 MHz, CDCl$_3$) δ: 1.26-1.37 (2H, m), 1.46-1.54 (1H, m), 1.64 (2H, bd, J=12.2 Hz), 1.95 (2H, dt, J=16.2, 5.8 Hz), 2.09-2.15 (2H, m), 2.49 (2H, d, J=7.1 Hz), 2.55 (2H, bt, J=8.4 Hz), 2.64 (2H, t, J=6.6 Hz), 2.81 (2H, bt, J=8.4 Hz), 2.93 (2H, t, J=6.6 Hz), 2.96 (2H, d, J=12.2 Hz), 3.50 (3H, s), 3.81 (2H, dd, J=5.5, 4.3 Hz), 4.17 (2H, dd, J=5.5, 4.3 Hz), 6.64 (1H, dd, J=8.0, 2.0 Hz), 6.71 (1H, d, J=2.0 Hz), 7.17 (1H, d; J=7.8 Hz), 7.32 (1H, dd, J=7.8, 1.8 Hz), 7.41 (1H, d, J=8.0 Hz), 7.86 (1H, d, J=1.8 Hz).

Example 3

(6-(2-{4-[4-Bromo-3-(2-methoxyethoxy)benzyl] piperidin-1-yl}ethyl)-2,3-dihydro-4H-chromen-4-one

[Formula 38]

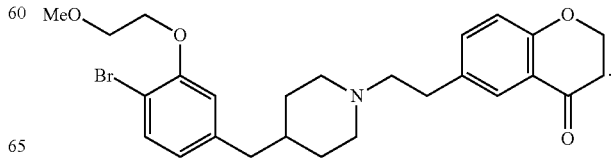

The compound (RE3) (52.0 g, 143 mmol) was added to a 5% aqueous potassium carbonate solution (350 mL), followed by extraction with toluene (700 mL×3). The combined organic layers were dried over anhydrous sodium sulfate, and the solvent was distilled off under reduced pressure to obtain 4-[4-Bromo-3-(2-methoxyethoxy)benzyl]piperidine (48.1 g). Next, a solution of the 4-[4-Bromo-3-(2-methoxyethoxy)benzyl]piperidine (2.00 g, 6.1 mmol), the compound (RE7) (2.01 g, 5.8 mmol), and potassium carbonate (1.66 g, 12 mmol) in acetonitrile (20 mL) was stirred at 70 to 80° C. for 7 hours. After cooling to room temperature, water (100 mL) was added thereto, followed by extraction with chloroform. The chloroform layer was dried over anhydrous sodium sulfate. The solvent was distilled off under reduced pressure. Then, the obtained concentrated residue was purified by silica gel column chromatography (n-hexane:ethyl acetate=1: 1→chloroform:methanol=20:1) to obtain the title compound (3.07 g, quantitative).

Retention time (Condition 1): 29.11 minutes $^1$H-NMR (300 MHz, CDCl$_3$) δ: 1.24-1.39 (2H, m), 1.40-1.73 (3H, m), 1.93 (2H, t, J=10.6 Hz), 2.40-2.61 (2H, m), 2.48 (2H, d, J=7.2 Hz), 2.66-2.87 (2H, m), 2.79 (2H, t, J=6.4 Hz), 2.95 (2H, d, J=11.7 Hz), 3.49 (3H, s), 3.81 (2H, t, J=4.9 Hz), 4.17 (2H, t, J=4.9 Hz), 4.51 (2H, t, J=6.4 Hz), 6.64 (1H, dd, J=8.1, 1.8 Hz), 6.71 (1H, d, J=1.8 Hz), 6.89 (1H, d, J=8.4 Hz), 7.32 (1H, dd, J=8.4, 2.2 Hz), 7.41 (1H, d, J=8.1 Hz), 7.70 (1H, d, J=2.2 Hz).

Example 4

6-(2-{4-[4-Bromo-3-(2-methoxyethoxy)benzyl]piperidin-1-yl}ethyl)-2,3-dihydro-4H-chromen-4-one hydrochloride

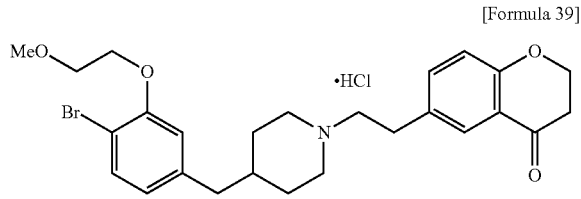 [SMILES: COCCOc1cc(CC2CCN(CCc3ccc4c(c3)C(=O)CCO4)CC2)ccc1Br]

[Formula 39]

An aqueous concentrated hydrochloric acid solution (36%, 760 μL, 8.5 mmol) was added at room temperature to a solution of the compound (3.07 g, 5.8 mmol) obtained in Example 3 in 2-propanol (20 mL), and the solution was stirred at room temperature for 15.5 hours. The precipitate was collected by filtration, washed with 2-propanol (2 mL×2), and dried under reduced pressure to obtain the title compound (2.26 g, 72%) as a white powder.

Melting point: 156-157° C.

Example 5

6-(2-{4-[4-Bromo-3-(2-methoxyethoxy)benzyl]piperidin-1-yl}ethyl)-2,3-dihydro-4H-chromen-4-one benzenesulfonate

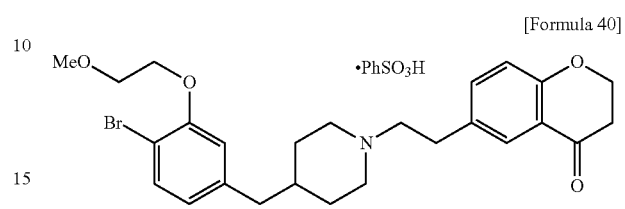

[Formula 40]

A solution of the compound (1.00 g, 2.0 mmol) obtained in Example 3 and benzenesulfonic acid monohydrate (316 mg, 2.0 mmol) in 2-propanol (5 mL) was heated to 70° C. The dissolution of the solid matter was confirmed, and the solution was then stirred with cooling to room temperature over 4 hours. The resulting precipitate was collected by filtration, then washed with 2-propanol (1 mL×2), and then dried under reduced pressure to obtain a crude product of the title compound (1.13 g). A 500 mg aliquot thereof was added to a mixed solution of acetone (10 mL) and water (100 μL), and the mixture was heated. The dissolution thereof was confirmed, and the solution was then gradually cooled and stirred at 35 to 40° C. for 1 hour. Then, the solution was further cooled and stirred at 20 to 25° C. for 1 hour. The precipitate was collected by filtration and washed with acetone (1 mL) to obtain the title compound (323 mg).

Melting point: 143-144° C.

Compounds shown in Examples 6 to 20 below were produced by the same synthetic method as in Example 1. The corresponding compounds were appropriately selected from among the compounds (RE1) to (RE10) shown in Reference Examples and used as starting materials.

Example 6

7-(2-{4-[4-Bromo-3-(2-methoxyethoxy)benzyl]piperidin-1-yl}ethyl)-3,4-dihydro-1-benzoxepin-5(2H)-one Retention time (Condition 1): 30.84 minutes $^1$H-NMR (300 MHz, CDCl$_3$) δ: 1.25-1.42 (2H, m), 1.44-1.72 (3H, m), 1.96 (2H, bt, J=11.0 Hz), 2.15-2.24 (2H, m), 2.49 (2H, d, J=7.0 Hz), 2.55 (2H, bdd, J=9.9, 5.7 Hz), 2.79 (2H, bdd, J=9.9, 5.7 Hz), 2.89 (2H, t, J=6.9 Hz), 2.99 (2H, bd, J=11.0 Hz), 3.50 (3H, s), 3.81 (2H, dd, J=5.3, 4.2 Hz), 4.14-4.25 (4H, m), 6.64 (1H, dd, J=8.0, 1.8 Hz), 6.71 (1H, d, J=1.8 Hz), 6.99 (1H, d, J=8.3 Hz), 7.27 (1H, dd, J=8.3, 2.5 Hz), 7.41 (1H, d, J=8.1 Hz), 7.58 (1.0H, d, J=2.5 Hz).

Example 7

6-(2-{4-[4-Chloro-3-(2-methoxyethoxy)benzyl]piperidin-1-yl}ethyl)-2,3-dihydro-4H-chromen-4-one Retention time (Condition 1): 27.43 minutes $^1$H-NMR (400 MHz, CDCl$_3$) δ: 1.23-1.37 (2H, m), 1.43-1.56 (1H, m), 1.60-1.78 (2H, m), 1.94 (2H, t like, J=12 Hz), 2.49 (2H, d, J=7.2 Hz), 2.50-2.55 (2H, m), 2.72-2.80 (2H, m), 2.79 (2H, t, J=6.4 Hz), 2.96 (2H, d like, J=11.5 Hz), 3.49 (3H, s), 3.81 (2H, t, J=4.8 Hz), 4.18 (2H, t, J=4.8 Hz), 4.51 (2H, t, J=6.4 Hz), 6.69 (1H, dd, J=8.0, 1.8 Hz), 6.74 (1H, d, J=1.8 Hz), 6.89 (1H, d, J=8.5 Hz), 7.24 (1H, d, J=8.0 Hz), 7.31 (1H, dd, J=8.5, 2.2 Hz), 7.70 (1H, d, J=2.2 Hz).

Example 8

6-(2-{4-[3-(2-Methoxyethoxy)-4-methylbenzyl]piperidin-1-yl}ethyl)-2,3-dihydro-1H-inden-1-one Retention time (Condition 1): 25.84 minutes
$^1$H-NMR (300 MHz, CDCl$_3$) δ: 1.20-1.60 (3H, m), 1.66 (2H, d, J=13.0 Hz), 1.95 (2H, t, J=11.7 Hz), 2.21 (3H, s), 2.49 (2H, d, J=7.0 Hz), 2.53-2.58 (2H, m), 2.69 (2H, t, J=5.9 Hz), 2.86 (2H, t, J=8.6 Hz), 2.96 (2H, d, J=11.4 Hz), 3.10 (2H, t, J=6.1 Hz), 3.47 (3H, s), 3.78 (2H, t, J=4.6 Hz), 4.12 (2H, t, J=5.5 Hz), 6.62 (1H, s), 6.65 (1H, d, J=7.9 Hz), 7.03 (1H, d, J=7.5 Hz), 7.39 (1H, d, J=7.9 Hz), 7.44 (1H, d, J=7.9 Hz), 7.58 (1H, s).

Example 9

7-(2-{4-[3-(2-Methoxyethoxy)-4-methylbenzyl]piperidin-1-yl}ethyl)-3,4-dihydronaphthalen-1(2H)-one Retention time (Condition 1): 30.36 minutes
$^1$H-NMR (300 MHz, CDCl$_3$) δ: 1.30-1.80 (5H, m), 1.99 (2H; t, J=11.9 Hz), 2.12 (2H, quint, J=6.2 Hz), 2.21 (3H, s), 2.50 (2H, d, J=6.6 Hz), 2.54-2.70 (4H, m), 2.80-2.90 (2H, m), 2.93 (2H, t, J=5.9 Hz), 3.01 (2H, d, J=10.8 Hz), 3.47 (3H, s), 3.78 (2H, t, J=4.6 Hz), 4.12 (2H, t, J=5.5 Hz), 6.61 (1H, s), 6.65 (1H, d, J=7.5 Hz), 7.03 (1H, d, J=7.5 Hz), 7.18 (1H, d, J=7.7 Hz), 7.33 (1H, dd, J=1.5, 7.9 Hz), 7.86 (1H, d, J=1.7 Hz).

Example 10

6-(2-{4-[(3-(2-Methoxyethoxy)-4-methylbenzyl]piperidin-1-yl}ethyl)-2,3-dihydro-4H-chromen-4-one Retention time (Condition 1): 27.01 minutes
$^1$H-NMR (CDCl$_3$) δ: 1.20-1.41 (2H, m), 1.43-1.73 (3H, m), 1.93 (2H, t like, J=10.9 Hz), 2.20 (3H, s), 2.41-2.62 (2H, m), 2.49 (2H, d, J=7.1 Hz), 2.67-2.87 (4H, m), 2.95 (2H, d, J=10.7 Hz), 3.47 (3H, s), 3.77 (2H, t, J=4.8 Hz), 4.12 (2H, t, J=4.9 Hz), 4.51 (2H, t, J=6.3 Hz), 6.61 (1H, s), 6.65 (1H, d, J=7.6 Hz), 6.89 (1H, d, J=8.5 Hz), 7.03 (1H, d, J=7.6 Hz), 7.32 (1H, dd, J=8.4, 2.3 Hz), 7.70 (1H, d, J=2.2 Hz).

Example 11

6-(2-{4-[4-Bromo-3-(2-hydroxyethoxy)benzyl]piperidin-1-yl}ethyl)-2,3-dihydro-1H-inden-1-one Retention time (Condition 1): 17.50 minutes
$^1$H-NMR (400 MHz, CDCl$_3$) δ: 1.38-1.26 (2H, m), 1.46-1.68 (3H, m), 1.96 (2H, bt, J=11.1 Hz), 2.50 (2H, d, J=7.1 Hz), 2.57 (2H, bt, J=7.8 Hz), 2.67-2.71 (2H, m), 2.86 (2H, bt, J=7.8 Hz), 2.98 (2H, bd, J=11.1 Hz), 3.10 (2H, bt, J=5.9 Hz), 3.99 (2H, bt, J=4.5 Hz), 4.15 (2H, bt, J=4.5 Hz), 6.67 (1H, dd, J=8.0, 1.7 Hz), 6.71 (1H, d, J=1.7 Hz), 7.39 (1H, d, J=7.8 Hz), 7.42 (1H, d, J=8.0 Hz), 7.44 (1H, dd, J=7.8, 1.5 Hz), 7.58 (1H, bs).

Example 12

7-(2-{4-[4-Bromo-3-(2-hydroxyethoxy)benzyl]piperidin-1-yl}ethyl)-3,4-dihydronaphthalen-1(2H)-one Retention time (Condition 1): 21.91 minutes
$^1$H-NMR (400 MHz, CDCl$_3$) δ: 1.24-1.39 (2H, m), 1.46-1.70 (3H, m), 1.95 (2H, bt, J=12.2 Hz), 2.09-2.15 (2H, m), 2.50 (2H, d, J=7.1 Hz), 2.51-2.59 (2H, m), 2.64 (2H, t, J=6.6 Hz), 2.78-2.83 (2H, m), 2.93 (2H, t, J=6.6 Hz), 2.96 (2H, d, J=12.2 Hz), 3.99 (2H, bt, J=4.4 Hz), 4.15 (2H, t, J=4.5 Hz), 6.67 (1H, dd, J=8.0, 2.0 Hz), 6.71 (1H, d, J=2.0 Hz), 7.17 (1H, d, J=7.8 Hz), 7.31 (1H, dd, J=7.8, 2.0 Hz), 7.42 (1H, d, J=8.0 Hz), 7.86 (1H, d, J=2.0 Hz).

Example 13

6-(2-{4-[4-Bromo-3-(2-hydroxyethoxy)benzyl]piperidin-1-yl}ethyl)-2,3-dihydro-4H-chromen-4-one Retention time (Condition 1): 18.91 minutes
$^1$H NMR (300 MHz, CDCl$_3$) δ: 1.28-1.42 (2H, m), 1.62-1.78 (1H, m), 1.66 (2H, bd, J=12.7 Hz), 2.00 (2H, bt, J=11.6 Hz), 2.50 (2H, d, J=7.0 Hz), 2.58 (2H, dd, J=11.0, 7.7 Hz), 2.76-2.81 (4H, m), 3.01 (2H, bd, J=11.6 Hz), 3.99 (2H, bt, J=4.5 Hz), 4.15 (2H, bd. J=4.5 Hz), 4.51 (2H, t, J=6.8 Hz), 6.66 (1H, dd, J=8.1, 1.8 Hz), 6.71 (1H, d, J=1.8 Hz), 6.90 (1H, d, J=8.5 Hz), 7.33 (1H, dd, J=8.5, 2.4 Hz), 7.42 (1H, d, J=8.1 Hz), 7.70 (1H, d, J=2.4 Hz).

Example 14

7-(2-{4-[4-Bromo-3-(2-hydroxyethoxy)benzyl]piperidin-1-yl}ethyl)-3,4-dihydro-1-benzoxepin-5(2H)-one Retention time (Condition 1): 20.89 minutes
$^1$H-NMR (300 MHz, CDCl$_3$) δ: 1.25-1.45 (2H, m), 1.44-1.70 (3H, m), 1.96 (2H, bt, J=11.2 Hz), 2.15-2.24 (2H, m), 2.50 (2H, d, J=6.6 Hz), 2.54 (2H, bdd, J=9.9, 6.1 Hz), 2.78 (2H, bdd, J=9.9, 6.1 Hz), 2.89 (2H, t, J=6.6 Hz), 2.98 (2H, bd, J=11.2 Hz), 3.99 (2H, bt, J=4.4 Hz), 4.15 (2H, t, J=4.4 Hz), 4.21 (2H, t, J=6.6 Hz), 6.67 (1H, dd, J=8.1, 2.0 Hz), 6.71 (1H, d, J=2.0 Hz), 6.99 (1H, d, J=8.3 Hz), 7.26 (1H, dd, J=8.3, 2.4 Hz), 7.42 (1H, d, J=8.1 Hz), 7.58 (1H, d, J=2.4 Hz).

Example 15

6-(2-{4-[3-Bromo-5-(2-methoxyethoxy)benzyl]piperidin-1-yl}ethyl)-2,3-dihydro-1H-inden-1-one Retention time (Condition 1): 27.89 minutes
$^1$H-NMR (300 MHz, CDCl$_3$) δ: 1.24-1.42 (2H, m), 1.46-1.70 (3H, m), 1.97 (2H, bt, J=10.3 Hz), 2.47 (2H, d, J=7.0 Hz), 2.58 (2H, bt, J=7.8 Hz), 2.67-2.71 (2H, m), 2.87 (2H, bt, J=7.8 Hz), 2.98 (2H, bd, J=10.3 Hz), 3.11 (2H, t, J=5.9 Hz), 3.45 (3H, s), 3.72-3.75 (2H, m), 4.07-4.10 (2H, m), 6.66 (1H, td, J=1.9, 0.3 Hz), 6.89-6.92 (2H, m), 7.39 (1H, d, J=8.0 Hz), 7.45 (1H, dd, J=8.0, 1.6 Hz), 7.58 (1H, d, J=1.6 Hz).

Example 16

7-(2-{4-[3-Bromo-5-(2-methoxyethoxy)benzyl]piperidin-1-yl}ethyl)-3,4-dihydronaphthalen-1(2H)-one Retention time (Condition 1): 32.39 minutes
$^1$H-NMR (400 MHz, CDCl$_3$) δ: 1.28-1.40 (2H, m), 1.46-1.56 (1H, m), 1.64 (2H, bd, J=12.6 Hz), 1.98 (2H, bt, J=11.0 Hz), 2.08-2.15 (2H, m), 2.46 (2H, d, J=7.0 Hz), 2.52-2.60 (2H, m), 2.64 (2H, t, J=6.1 Hz), 2.80-2.87 (2H, m), 2.93 (2H, t, J=6.1 Hz), 2.98 (2H, d, J=11.0 Hz), 3.45 (3H, s), 3.73 (2H, t, J=4.6 Hz), 4.08 (2H, t, J=4.6 Hz), 6.66 (1H, bs), 6.88-6.92 (2H, m), 7.17 (1H, dt, J=7.8 Hz), 7.32 (1H, dd, J=7.8, 1.7 Hz), 7.85 (1H, d, J=1.7 Hz).

Example 17

6-(2-{4-[(3-Bromo-5-(2-methoxyethoxy)benzyl]piperidin-1-yl}ethyl)-2,3-dihydro-4H-chromen-4-one Retention time (Condition 1): 29.33 minutes
$^1$H-NMR (400 MHz, CDCl$_3$) δ: 1.26-1.37 (2H, m), 1.45-1.68 (3H, m), 1.94 (2H, bt, J=11.5 Hz), 2.46 (2H, d, J=7.1 Hz), 2.49-2.55 (2H, m), 2.73-2.81 (4H, m), 2.96 (2H, bd, J=11.5 Hz), 3.45 (3H, s), 3.72-3.75 (2H, m), 4.07-4.11 (2H, m), 4.51 (2H, t, J=6.3 Hz), 6.62 (1H, bt, J=1.8 Hz), 6.88-6.90 (3H, m), 7.32 (1H, dd, J=8.5, 2.3 Hz), 7.70 (1H, d, J=2.3 Hz).

Example 18

7-(2-{4-[3-Bromo-5-(2-methoxyethoxy)benzyl]piperidin-1-yl}ethyl)-3,4-dihydro-1-benzoxepin-5(2H)-one Retention time (Condition 1): 31.43 minutes
$^1$H-NMR (300 MHz, CDCl$_3$) δ: 1.25-1.41 (2H, m), 1.44-1.69 (3H, m), 1.96 (2H, bt, J=11.6 Hz), 2.15-2.24 (2H, m), 2.46 (2H, d, J=7.0 Hz), 2.54 (2H, bdd, J=9.9, 6.4 Hz), 2.79 (2H, bdd, J=9.9, 6.4 Hz), 2.89 (2H, t, J=7.0 Hz), 2.97 (2H, bd, J=11.6 Hz), 3.72-3.75 (2H, m), 3.45 (3H, s), 4.07-4.10 (2H, m), 4.21 (2H, t, J=6.7 Hz), 6.66 (1H, t, J=1.8 Hz), 6.88-6.92 (2H, m), 6.99 (1H, d, J=8.3 Hz), 7.27 (1H, dd, J=8.3, 2.4 Hz), 7.58 (1H, d, J=2.4 Hz).

Example 19

6-(2-{4-[3-Chloro-5-(2-methoxyethoxy)benzyl]piperidin-1-yl}ethyl)-2,3-dihydro-1H-inden-1-one Retention time (Condition 1): 26.77 minutes
$^1$H-NMR (300 MHz, CDCl$_3$) δ: 1.25-1.39 (2H, m), 1.47-1.58 (1H, m), 1.65 (2H, bd, J=12.7 Hz), 1.96 (2H, bt, J=11.1 Hz), 2.47 (2H, d, J=7.1 Hz), 2.55-2.59 (2H, m), 2.68-2.71 (2H, m), 2.84-2.88 (2H, m), 2.98 (2H, bd, J=11.5 Hz), 3.10 (2H, t, J=5.7 Hz), 3.45 (3H, s), 3.73-3.75 (2H, m), 4.08-4.10 (2H, m), 6.62 (1H, bt, J=1.8 Hz), 6.73-6.77 (2H, m), 7.39 (1H, d, J=7.8 Hz), 7.44 (1H, dd, J=7.8, 1.7 Hz), 7.58 (1H, bs).

Example 20

6-(2-{4-[3-Chloro-5-(2-methoxyethoxy)benzyl]piperidin-1-yl}ethyl)-2,3-dihydro-4H-chromen-4-one Retention time (Condition 1): 28.33 minutes
$^1$H-NMR (300 MHz, CDCl$_3$) δ: 1.20-1.39 (2H, m), 1.45-1.58 (1H, m), 1.65 (2H, bd, J=13.4 Hz), 1.96 (2H, bt, J=10.6 Hz), 2.47 (2H, d, J=7.0 Hz), 2.50-2.59 (2H, m), 2.73-2.82 (4H, m), 2.98 (2H, bd, J=11.6 Hz), 3.45 (3H, s), 3.72-3.76 (2H, m), 4.07-4.10 (2H, m), 4.51 (2H, t, J=6.4 Hz), 6.62 (1H, bt, J=1.7 Hz), 6.73-6.78 (2H, m), 6.90 (1H, d, J=8.4 Hz), 7.32 (1H, dd, J=8.4, 2.4 Hz), 7.70 (1H, d, J=2.4 Hz).

The structural formulae of the compounds of Examples 6 to 20 are shown in Table 1 below.

TABLE 1

General Formula:

| Example No. | R$^1$ | R$^2$ | X | n |
|---|---|---|---|---|
| 6 | Me | p-Br | O | 3 |
| 7 | Me | p-Cl | O | 2 |
| 8 | Me | p-Me | CH$_2$ | 1 |
| 9 | Me | p-Me | CH$_2$ | 2 |
| 10 | Me | p-Me | O | 2 |
| 11 | H | p-Br | CH$_2$ | 1 |
| 12 | H | p-Br | CH$_2$ | 2 |
| 13 | H | p-Br | O | 2 |
| 14 | H | p-Br | O | 3 |
| 15 | Me | m-Br | CH$_2$ | 1 |
| 16 | Me | m-Br | CH$_2$ | 2 |
| 17 | Me | m-Br | O | 2 |
| 18 | Me | m-Br | O | 3 |
| 19 | Me | m-Cl | CH$_2$ | 1 |
| 20 | Me | m-Cl | O | 2 |

Example 21

6-(2-{4-[4-Bromo-3-(2-methoxyethoxy)benzyl]piperidin-1-yl}ethyl)-2,3-dihydro-4H-chromen-4-one fumarate

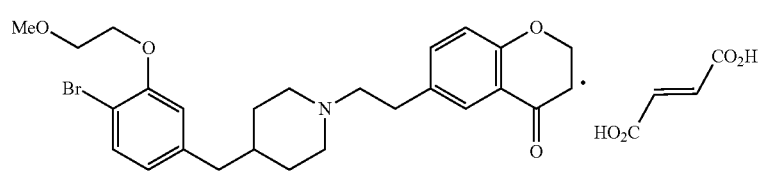

[Formula 41]

A solution of the compound (503 mg, 1.00 mmol) obtained in Example 3 and fumaric acid (58 mg, 0.50 mmol) in ethanol (10 mL) was concentrated under reduced pressure to obtain a concentrated residue (557 mg). A 100 mg aliquot thereof was added to acetone (3 mL), and the mixture was stirred at room temperature for 1 hour. Then, the precipitate was collected by filtration and dried under reduced pressure to obtain the title compound (42 mg).

Melting point: 149-150° C.

Example 22

6-(2-{4-[4-Bromo-3-(2-hydroxyethoxy)benzyl]piperidin-1-yl}ethyl)-2,3-dihydro-4H-chromen-4-one hydrochloride

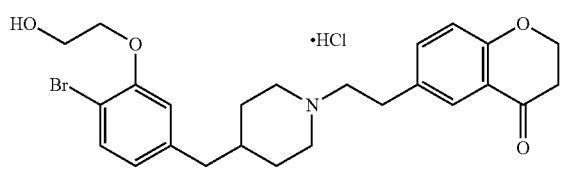

[Formula 42]

An aqueous concentrated hydrochloric acid solution (36%, 860 μL, 10 mmol) was added at room temperature to a solution of the compound (3.96 g, 8.1 mmol) obtained in Example 13 in 2-propanol (40 mL) and dichloromethane (50 mL), and the solvent was removed by concentration under reduced pressure. 2-Propanol (72 mL) was added to the obtained concentrated residue (3.61 g), and the mixture was heated under reflux for 2 hours and stirred with cooling to 20° C. over 3 hours. The mixture was stirred at 20° C. for 1 hour and then stirred for 1 hour with ice cooling. The precipitate was collected by filtration and washed with cold 2-propanol (4 mL×2) to obtain a white solid (3.35 g). To this white solid, 2-propanol (100 mL) and aqueous concentrated hydrochloric acid solution (36%, 500 μL) were added, and the mixture was heated to a reflux temperature. The dissolution of the solid matter was confirmed, and the solution was then cooled to 60° C. Precipitation was confirmed, and the mixture was then stirred at 55 to 60° C. for 1 hour. Subsequently, the mixture was stirred with cooling to 20° C. over 2 hours and then stirred at 20° C. for 1 hour. The precipitate was collected by filtration and washed with 2-propanol (4 mL×2) to obtain the title compound (3.10 g, 73%) as a white powder.

Melting point: 177-178° C.

Example 23

6-(2-{4-[4-Bromo-3-(2-methoxyethoxy)benzyl]piperidin-1-yl}ethyl)-2,3-dihydro-4H-chromen-4-one hydrobromide

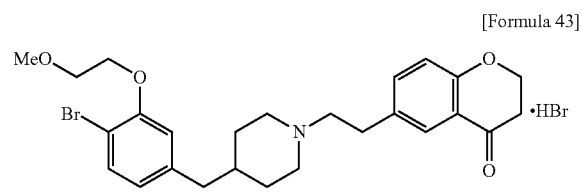 [SMILES: COCCOc1cc(CC2CCN(CCc3ccc4c(c3)C(=O)CCO4)CC2)ccc1Br ; Br]

[Formula 43]

A 48% aqueous hydrobromic acid solution (170 μL, 2.4 mmol) was added with ice cooling to a solution of the compound (1.00 g, 2.00 mmol) obtained in Example 3 in 2-propanol (10 mL), and the solution was warmed to room temperature and stirred overnight. The resulting precipitate was collected by filtration, then washed with 2-propanol (1 mL×2), and then dried under reduced pressure to obtain a crude crystal of the title compound (797 mg). The crude crystal (750 mg) was added to 2-propanol (30 mL), and the mixture was heated under reflux. The dissolution of the solid matter was confirmed. The solution was then gradually cooled to room temperature, while it was stirred for 19 hours. The resulting precipitate was collected by filtration, then washed with 2-propanol (1 mL×2), and then dried under reduced pressure to obtain the title compound (613 mg) as a white crystalline solid.

Melting point: 148-150° C.

Example 24

6-(2-{4-[4-Bromo-3-(2-methoxyethoxy)benzyl]piperidin-1-yl}ethyl)-2,3-dihydro-4H-chromen-4-one butanedioate

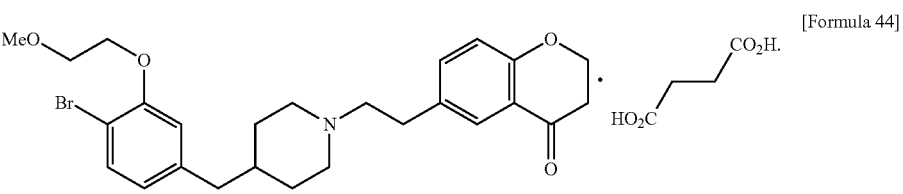 [SMILES: COCCOc1cc(CC2CCN(CCc3ccc4c(c3)C(=O)CCO4)CC2)ccc1Br ; O=C(O)CCC(=O)O]

[Formula 44]

The compound (218 mg, 0.43 mmol) obtained in Example 3 and Succinic acid (26 mg, 0.22 mmol) were added to ethanol (10 mL). The dissolution thereof was confirmed, and the solvent was then distilled off under reduced pressure to obtain a concentrated residue (244 mg). The concentrated residue (105 mg) was stirred for 1 hour in 2-butanone/n-hexane (1:1, 1 mL). The resulting precipitate was collected by filtration and dried under reduced pressure at room temperature to obtain the title compound (36 mg, 62%) as a white powder.

Melting point: 100-101° C.

$^1$H-NMR (DMSO-$d_6$) δ: 1.10-1.25 (2H, m), 1.45-1.60 (3H, m), 1.94-2.07 (2H, m), 2.39 (4H, s), 2.47 (2H, d, J=6.6 Hz), 2.53-2.58 (2H, m), 2.68-2.75 (2H, m), 2.76 (2H, t, J=6.5 Hz), 2.92-3.01 (2H, m), 3.34 (3H, s), 3.68 (2H, t, J=4.5 Hz), 4.16 (2H, t, J=4.5 Hz), 4.50 (2H, t, J=6.3 Hz), 6.69 (1H, dd, J=8.0, 1.5 Hz), 6.94 (1H, d, J=1.5 Hz), 6.95 (1H, d, J=8.5 Hz), 7.42 (1H, dd, J=8.5, 2.4 Hz), 7.44 (1H, d, J=8.0 Hz), 7.58 (1H, d, J=2.4 Hz).

Example 25

6-(2-{4-[4-Bromo-3-(2-methoxyethoxy)benzyl]piperidin-1-yl}ethyl)-2,3-dihydro-4H-chromen-4-one benzenesulfonate The compound (RE3) (10.0 g, 27.4 mmol) was added to an aqueous potassium hydroxide solution (prepared from potassium hydroxide [2.15 g, 32.9 mmol] and water [50 mL]), followed by extraction with toluene (50 mL×2). All the organic layers were combined, and the solvent was distilled off under reduced pressure to obtain a concentrated residue 1. To this concentrated residue 1, the compound (RE11) (9.57 g, 28.8 mmol), dipotassium hydrogen phosphate (14.3 g, 82.3 mmol), N-methyl-2-pyrrolidinone (3.0 mL), and toluene (100 mL) were added, and the mixture was stirred at 110 to 120° C. for 6.5 hours. After cooling to 40 to 50° C., water (100 mL), tetrahydrofuran (50 mL), and toluene (50 mL) were added thereto. The organic layer was washed with water (50 mL). The solvent was distilled off under reduced pressure to obtain a concentrated residue 2, which was in turn used in separate portions in the subsequent reactions without further purification. A solution of a 1/5 volume (which corresponds to 5.5 mmol) of the concentrated residue 2 in acetone (8 mL) was added at 40 to 50° C. to a suspension of benzenesulfonic acid ammonium (0.96 g, 5.48 mmol) in acetone (32 mL). The mixture was stirred at 50° C. for 1 hour. The complete dissolution of the solid matter was confirmed, and the solvent was then distilled off under reduced pressure. Acetone (20 mL) was added to the concentrated residue, and the mixture was heated to 50° C. for dissolution. Then, a seed crystal (5.0 mg) was added thereto at 40° C. The mixture was stirred at 40° C. for 1 hour and gradually cooled to room temperature. Then, the mixture was stirred for 3 hours in an ice bath, and the precipitate was collected by filtration, washed with cold acetone (4.0 mL×2), and dried under reduced pressure to obtain the title compound (2.85 g, 79%).

Example 26

6-(2-{4-[4-Bromo-3-(2-methoxyethoxy)benzyl]piperidin-1-yl}ethyl)-2,3-dihydro-4H-chromen-4-one benzenesulfonate A suspension of the compound (RE3) (30.0 g, 82.3 mmol), the compound (RE7) (29.9 g, 86.4 mmol), and potassium carbonate (34.11 g, 247 mmol) in acetonitrile (236 g) was heated under reflux for 6.5 hours. The reaction mixture was cooled to room temperature and then separated into aqueous and organic layers by the addition of toluene (519 g) and water (600 g). The organic layer was washed with water (300 g), and the solvent was then distilled off under reduced pressure to obtain a concentrated residue (44.6 g). Acetone (170 g) was added to the concentrated residue, and the mixture was filtered. The residue on the filter was washed with acetone (40 g). To all the filtrates, water (3 g) was added, and the mixture was warmed to 40° C. Benzenesulfonic acid monohydrate (15.2 g, 96 mmol) and then a seed crystal (0.15 g) were added thereto, and the mixture was stirred at 40° C. for 1 hour. Subsequently, the mixture was gradually cooled to 2° C., while it was stirred. The mixture was stirred at the solution temperature of 2° C. for 1 hour. Then, the precipitate was collected by filtration, washed with cold acetone (47.5 g×2), and dried under reduced pressure at 40° C. to obtain the title compound (36.8 g, 68%) as a white crystalline solid.

Example 27

Form 1-type Crystal of 6-(2-{4-[4-Bromo-3-(2-methoxyethoxy)benzyl]piperidin-1-yl}ethyl)-2,3-dihydro-4H-chromen-4-one hydrochloride The compound (RE3) (52.0 g, 143 mmol) was added to a 5% aqueous potassium carbonate solution (350 mL), followed by extraction with toluene (700 mL×3). The combined organic layers were dried over anhydrous sodium sulfate, and the solvent was distilled off under reduced pressure to obtain 4-[4-Bromo-3-(2-methoxyethoxy)benzyl]piperidine (48.1 g). This compound was added together with the compound (RE7) (47.0 g, 143 mmol) and potassium carbonate (37.5 g, 271 mmol) to acetonitrile (470 mL), and the reaction mixture was stirred at the solution temperature of 55 to 60° C. for 25 hours. The mixture was cooled to room temperature and then separated into aqueous and organic layers by the addition of water (940 mL) and toluene (940 mL). The aqueous layer was extracted with toluene (470 mL). The combined organic layers were dried over anhydrous sodium sulfate, and the solvent was then distilled off under reduced pressure. 2-Propanol (1.1 L) was added to the obtained concentrated residue (76.6 g). An aqueous concentrated hydrochloric acid solution (36%, 14 mL, 171 mmol) was added dropwise thereto at 15 to 20° C. over 5 minutes with water cooling, and the solution was stirred for 2 hours at 15 to 20° C. for 22 hours. Then, the solution was cooled in an ice bath and stirred for 4.5 hours. The precipitate was collected by filtration, then washed with cold 2-propanol (55 mL×2), and dried under reduced pressure to obtain a concentrated residue (61.6 g). To this concentrated residue, 2-propanol (900 mL) and a 36% aqueous concentrated hydrochloric acid solution (36%, 9.0 mL) were added, and the mixture was heated. The complete dissolution thereof at around 60° C. was confirmed, and the solution was then cooled to 20° C. and stirred at 15 to 20° C. for 14.5 hours. Then, the solution was cooled in an ice bath and stirred for 5 hours. The precipitate was collected by filtration, then washed with cold 2-propanol (70 mL×2), and dried under reduced pressure to obtain the title compound (51.1 g, 70%) as a colorless crystalline solid.

Melting point: 157-159° C.

Elemental Analysis

TABLE 2

| Element | C | H | N | Cl | Br |
| --- | --- | --- | --- | --- | --- |
| Found Ratio (%) | 57.72 | 6.07 | 2.72 | 6.46 | 14.71 |
| Theoretical Ratio (%) | 57.95 | 6.17 | 2.60 | 6.58 | 14.83 |

Example 28

Form A-type Crystal of 6-(2-{4-[4-Bromo-3-(2-methoxyethoxy)benzyl]piperidin-1-yl}ethyl)-2,3-dihydro-4H-chromen-4-one benzenesulfonate A solution of the compound (1.00 g, 2.00 mmol) obtained in Example 3 and benzenesulfonic acid (316 mg, 2.0 mmol) in 2-propanol (5 mL) was warmed to 70° C. The dissolution of the solid matter was confirmed, and the solution was then stirred with cooling to room temperature over 4 hours. The resulting precipitate was collected by filtration, then washed with 2-propanol (1 mL×2), and then dried under reduced pressure to obtain a concentrated residue (1.13 g). A 1.05 g aliquot thereof was added to 2-propanol (32 mL), and the mixed solution was heated under reflux. The dissolution of the solid matter was confirmed, and the solution was then stirred with cooling. A seed crystal (2 mg) was added thereto at 65° C., and the mixture was stirred at 60 to 65° C. for 1 hour. Subsequently, the mixture was stirred with cooling to 30° C. over 2 hours and stirred for 1 hour with water cooling (25° C.). Then, the precipitate was collected by filtration, then washed with 2-propanol (2 mL×2), and then dried under reduced pressure to obtain the title compound (963 mg) as a colorless crystalline solid.

Melting point: 142-143° C.
Elemental Analysis

TABLE 3

| Element | C | H | N | S | Br |
| --- | --- | --- | --- | --- | --- |
| Found Ratio (%) | 58.18 | 5.83 | 2.30 | 4.87 | 12.07 |
| Theoretical Ratio (%) | 58.18 | 5.80 | 2.12 | 4.85 | 12.10 |

Example 29

Form B-type Crystal of 6-(2-{4-[4-Bromo-3-(2-methoxyethoxy)benzyl]piperidin-1-yl}ethyl)-2,3-dihydro-4H-chromen-4-one benzenesulfonate The compound (RE3) (2.00 g, 5.5 mmol) was added to a 10% aqueous potassium carbonate solution (20 mL), followed by extraction with toluene (20 mL×2). The solvent in the combined organic layers was distilled off under reduced pressure to obtain 4-[4-Bromo-3-(2-methoxyethoxy)benzyl]piperidine (1.95 g). Next, a solution of the 4-[4-Bromo-3-(2-methoxyethoxy)benzyl]piperidine (1.95 g, 5.5 mmol), the compound (RE7) (1.80 g, 5.2 mmol), and potassium carbonate (1.44 g, 10 mmol) in acetonitrile (10 mL) was stirred at 55 to 60° C. for 19 hours. The reaction solution was cooled to room temperature, and water (30 mL) was then added thereto, followed by extraction with toluene (30 mL×3). The combined organic layers were washed with a 5% aqueous sodium bicarbonate solution (30 mL) and water (30 mL) in this order, and the solvent was then distilled off under reduced pressure. The obtained concentrated residue was dissolved in acetone (40 mL), and benzenesulfonic acid monohydrate (1.06 g, 6.0 mmol) was added thereto. The dissolution of the solid matter was confirmed, and the solvent was then distilled off under reduced pressure. Acetone (40 mL) and water (0.4 mL) were added to the obtained concentrated residue, and the mixture was heated to 40° C. A seed crystal (5 mg) was added thereto, and the mixture was stirred at 35 to 40° C. for 1.5 hours. Subsequently, the mixture was cooled to 20° C. over 1 hour and then stirred for 1 hour with ice cooling. The precipitate was collected by filtration, then washed with cold acetone (5 mL×2), and then dried under reduced pressure at room temperature to obtain the title compound (2.45 g, 71%) as a colorless crystalline solid.

Melting point: 143-144° C.
Elemental Analysis

TABLE 4

| Element | C | H | N | S | Br |
| --- | --- | --- | --- | --- | --- |
| Found Ratio (%) | 58.09 | 5.80 | 2.25 | 4.85 | 12.10 |
| Theoretical Ratio (%) | 58.18 | 5.80 | 2.12 | 4.85 | 12.10 |

Example 30

Form C-type Crystal of 6-(2-{4-[4-Bromo-3-(2-methoxyethoxy)benzyl]piperidin-1-yl}ethyl)-2,3-dihydro-4H-chromen-4-one benzenesulfonate The compound (7.76 g, 15.5 mmol) obtained in Example 3 was dissolved in 1% (v/v) hydrated acetone (100 mL), and the solution was warmed to 40 to 45° C. Then, benzenesulfonic acid monohydrate (2.93 g, 17 mmol) was added thereto, and the mixture was stirred. The dissolution of the solid matter was confirmed. Then, a seed crystal (50 mg) was added thereto, and the mixture was stirred at 40 to 45° C. for 1 hour. Subsequently, the mixture was stirred with cooling to 25° C. over 3 hours and then stirred at room temperature for 17.5 hours. Subsequently, the mixture was cooled to 5° C. or lower over 1 hour and stirred at this temperature for 1 hour. The precipitation was collected by filtration, and the residue on the filter was washed with cold acetone (10 mL×2) and then dried under reduced pressure to obtain the title compound (8.83 g, 88%) as a colorless crystalline solid.

Melting point: 143-145° C. (Transition to Form A occurred at 128° C.)

$^1$H-NMR (400 MHz, DMSO-$d_6$) δ: 1.30-1.46 (2H, m), 1.72-1.86 (3H, m), 2.52 (2H, d, J=6.4 Hz), 2.78 (2H, t, J=6.5 Hz), 2.82-3.00 (4H, m), 3.18-3.30 (2H, m), 3.34 (3H, s), 3.48-3.58 (2H, m), 3.66-3.72 (2H, m), 4.12-4.20 (2H, m), 4.51 (2H, t, J=6.5 Hz), 6.72 (1H, dd, J=8.1, 2.0 Hz), 6.96 (1H, d, J=2.0 Hz), 7.01 (1H, d, J=8.5 Hz), 7.27-7.34 (3H, m), 7.44 (1H, dd, J=8.5, 2.2 Hz), 7.47 (1H, d, J=8.1 Hz), 7.56-7.61 (2H, m), 7.67 (1H, d, J=2.2 Hz), 9.02 (1H, br s).

Elemental Analysis

TABLE 5

| Element | C | H | N | S | Br |
| --- | --- | --- | --- | --- | --- |
| Found Ratio (%) | 58.42 | 5.83 | 2.26 | 4.86 | 12.11 |
| Theoretical Ratio (%) | 58.18 | 5.80 | 2.12 | 4.85 | 12.10 |

Example 31

Form A-type Crystal of 6-(2-{4-[4-Bromo-3-(2-methoxyethoxy)benzyl]piperidin-1-yl}ethyl)-2,3-dihydro-4H-chromen-4-one monofumarate The compound (3.0 g, 6.0 mmol) obtained in Example 3 was dissolved in ethanol (75 mL), and a solution of fumaric acid (693 mg, 6.0 mmol) in ethanol (25 mL) and further methanol (100 mL) were added thereto. The dissolution thereof was confirmed, and the solvent was then distilled off under reduced pressure to obtain a concentrated residue. To this concentrated residue, acetone (110 mL) was added, and the mixture was stirred at room temperature for 2.5 hours. The resulting precipitate was collected by filtration and dried under reduced pressure (40° C., 1 mmHg, 18 hours) to obtain the title compound (3.26 g, 88%) as a colorless crystalline solid.

Melting point: 149-151° C.

$^1$H-NMR (400 MHz, DMSO-d6) δ: 1.17-1.40 (2H, m), 1.47-1.73 (3.0H, m), 2.15-2.32 (2H, m), 2.48 (2H, d, J=6.4 Hz), 2.63-2.85 (6H, m), 3.05-3.17 (2H, m), 3.34 (3H, s), 3.65-3.72 (2H, m), 4.13-4.20 (2H, m), 4.50 (2H, t, J=6.4 Hz), 6.56 (2H, s), 6.70 (1H, dd, J=8.0, 1.7 Hz), 6.95 (2H, d, J=1.7 Hz), 6.97 (2H, d, J=8.6 Hz), 7.42 (2H, dd, J=8.6, 2.2 Hz), 7.45 (1H, d, J=8.0 Hz), 7.60 (1H, d, J=2.2 Hz).

Example 32

Form A+-type Crystal of 6-(2-{4-[4-Bromo-3-(2-methoxyethoxy)benzyl]piperidin-1-yl}ethyl)-2,3-dihydro-4H-chromen-4-one monofumarate The Form A-type crystal (500 mg) obtained in Example 31 was added to 1% hydrated acetone (25 mL), and the mixture was heated to 65° C. The dissolution thereof was confirmed. Then, the solution was gradually cooled to room temperature, while it was stirred for 17 hours. The resulting precipitate was collected by filtration and dried under reduced pressure (40° C., 1 mmHg, 24 hours) to obtain the title compound (403 mg, 80%) as a colorless crystalline solid.

Melting point: 148-149° C.

$^1$H-NMR: The same data as in Example 31 was obtained.

Example 33

6-(2-{4-[4-Bromo-3-(2-methoxyethoxy)benzyl]piperidin-1-yl}ethyl)-2,3-dihydro-4H-chromen-4-one benzenesulfonate 4-[4-Bromo-3-(2-methoxyethoxy)benzyl]piperidine hydrochloride (2.0 g, 5.48 mmol) was added to an aqueous potassium hydroxide solution (prepared from potassium hydroxide [0.43 g, 6.58 mmol] and water [10 ml]), followed by extraction with toluene (10 ml×2). All the organic layers were combined, and the solvent was distilled off under reduced pressure. 6-(2-p-Benzenesulfonyloxyethyl)-2,3-dihydro-4H-chromen-4-one (1.91 g, 5.76 mmol), dipotassium hydrogen phosphate (2.87 g, 16.5 mmol), N-methyl-2-piperidone (0.6 ml), and toluene (20 ml) were added to the concentrated residue, and the mixture was stirred at 110 to 120° C. for 6 hours. After cooling to 40 to 50° C., water (20 ml), tetrahydrofuran (10 ml), and toluene (10 ml) were added thereto. The organic layer was washed with water (10 ml). The solvent was distilled off under reduced pressure to obtain a concentrated residue. The obtained concentrated residue was dissolved in acetone (6.0 ml) without further purification, and a solution of benzenesulfonic acid (0.93 g, 5.76 mmol) in acetone (4.0 ml) was added dropwise thereto at 50 to 60° C. The mixture was stirred at 50 to 60° C. for 30 minutes. Then, n-butyl acetate (20.0 ml) was added dropwise thereto, and the mixture was further stirred for 1 hour. After cooling to room temperature, n-butyl acetate (10 ml) was added dropwise thereto, and the mixture was stirred for 3.5 hours in an ice bath. The precipitate was collected by filtration, washed with cold acetone (4.0 ml×2), and dried under reduced pressure to obtain the title compound (3.21 g, 89%).

Example 34

Form C-type Crystal of 6-(2-{4-[4-Bromo-3-(2-methoxyethoxy)benzyl]piperidin-1-yl}ethyl)-2,3-dihydro-4H-chromen-4-one benzenesulfonate 0.5% Hydrated acetone (15.2 mL) was added to 6-(2-{4-[4-Bromo-3-(2-methoxyethoxy)benzyl]piperidin-1-yl}ethyl)-2,3-dihydro-4H-chromen-4-one benzenesulfonate (1.0 g, 1.51 mmol), and the compound was dissolved at 50° C. or higher. The solution was cooled to 40 to 50° C. A seed crystal (Form C-type crystal obtained in Example 30) (5 mg) was added thereto, and the mixture was stirred at 40 to 50° C. for 1 hour. The mixture was cooled to room temperature and stirred at room temperature for 1 hour, and n-heptane (8.8 mL) was then added thereto. The mixture was stirred for 3 hours in an ice bath. Then, the precipitate was collected by filtration, then washed with acetone (2.5 mL), and then dried under reduced pressure at 50° C. to obtain the title compound (0.92 g, 92%) as a Form C-type crystal.

Test Example 1

Screening Test Using [$^3$H]Citalopram Binding for Evaluating Human Serotonin Reuptake Inhibitory Effect 1-1 Cells Used and Preparation of Membrane Preparation CHO cells containing a human serotonin transporter (h-SERT) expressed therein (h-SERT/CHO) were used in the experiment. The cells were cultured in F12 containing 10% FCS, 500 μg/ml Geneticin, and 100 U/ml penicillin-100 μg/ml streptomycin (all manufactured by Sigma-Aldrich Corp.) in a 5% $CO_2$ incubator and dissociated/collected using a SERT buffer (50 mM Tris-HCl (pH=7.4) containing 120 mM NaCl and 5 mM KCl). The resulting cells were homogenized using a Teflon (registered trademark) homogenizer and then centrifuged (50,000×g, 30 min, 4° C.). The pellet was resuspended in an appropriate amount of a SERT buffer and stored at −80° C. until use. The amount of the protein in the membrane preparation was quantified using Dye Reagent Concentrate (manufactured by Bio-Rad Laboratories, Inc.) with bovine serum albumin (manufactured by Sigma-Aldrich Corp.) as a standard.

1-2 Receptor Binding Experiment

[$^3$H]Citalopram binding was measured according to the method of Owens et al. [Owens M. J. et al., J. Pharm. Exp. Ther., 283, 1305-1322 (1997)]. Specifically, 50 μl of [$^3$H] citalopram (final concentration: approximately 2 nM) diluted with a SERT buffer, 149 μl of the h-SERT/CHO membrane preparation (40 μg/well in terms of the amount of the protein), and 1 μl of a solution of a test drug dissolved in dimethyl sulfoxide were mixed to prepare 200 μl in total of a solution. This solution was reacted at room temperature for 60 minutes and then rapidly filtered by suction at a low pressure through glass fiber filter paper coated with a 0.05% aqueous polyethyleneimine solution. The glass fiber filter paper was washed twice with 250 μl of a SERT buffer and then transferred to a glass vial containing 4 ml of ACS-II (manufactured by Amersham Biosciences). Radioactivity remaining on the filter paper was measured using a liquid scintillation counter. The amount of [$^3$H]citalopram bound in the presence of 1 μM clomipramine was used as the amount of [$^3$H]citalopram bound non-specifically.

An IC$_{50}$ value was calculated according to the Hill analysis [see Hill A. V., J. Physiol., 40, 190-200 (1910)]. A h-SERT binding inhibition constant (Ki) was calculated according to the equation:

$$h\text{-SERT binding inhibition constant}(Ki)=IC_{50}/(1+S/Kd)$$

wherein S represents the concentration of [$^3$H]citalopram added; and the Kd value represents the dissociation constant of [$^3$H]citalopram, wherein the Kd value used was the value (2.16 nM) calculated by a saturation binding experiment separately conducted using the same cell membrane as above. A smaller value of the h-SERT binding inhibition constant Ki means a higher human serotonin reuptake inhibitory effect.

Test Example 2

[$^3$H]8-OH-DPAT Binding Test for Evaluating Affinity for Human Serotonin 1A Receptor 2-1 Cells Used and Preparation of Membrane Preparation CHO cells containing a human serotonin 1A receptor (h-5-HT$_{1A}$) expressed therein (h-5-HT$_{1A}$/CHO) were used in the experiment. The cells were cultured in F12 containing 10% FCS, 500 μg/ml Geneticin, and 100 U/ml penicillin-100 μg/ml streptomycin (all manufactured by Sigma-Aldrich Corp.) in a 5% CO$_2$ incubator. The membrane preparation was prepared according to the method of Yabuuchi et al[3]. Specifically, the cells were dissociated/collected using 50 mM Tris-HCl (pH=7.4). The resulting cells were homogenized using a Teflon (registered trademark) homogenizer and then centrifuged (48,000×g, 20 min, 4° C.). The pellet was resuspended in an appropriate amount of 50 mM Tris-HCl (pH=7.4) and stored at −80° C. until use. The amount of the protein in the membrane preparation was quantified using Dye Reagent Concentrate (manufactured by Bio-Rad Laboratories, Inc.) with bovine serum albumin (manufactured by Sigma-Aldrich Corp.) as a standard.

2-2 Receptor Binding Experiment

The experiment was conducted according to the method of Yabuuchi et al. [Yabuuchi K. et al., Biogenic Amines, 18, 319-328 (2004)]. 50 μl of [$^3$H]8-OH-DPAT (final concentration: 0.5 nM), 1 μl of a test drug solution, and 149 μl of the h-5-HT$_{1A}$/CHO membrane preparation (25 μg/well in terms of the amount of the protein) were added to a buffer solution containing 50 mM Tris-HCl (pH=7.4) and 4 mM CaCl$_2$, and 200 μl in total of the reaction solution was used in measurement. The reaction solution was reacted at room temperature for 30 minutes and then rapidly filtered by suction at a low pressure through glass fiber filter paper. The glass fiber filter paper was washed twice with 250 μl of 50 mM Tris-HCl (pH=7.4) and then added to a counting vial containing 4 ml of ACS-II (manufactured by Amersham Biosciences). Receptor binding radioactivity remaining on the filter paper was measured using a liquid scintillation counter. The amount of [$^3$H] 8-OH-DPAT bound in the presence of 10 μM 8-OH-DPAT was used as the amount of [$^3$H]8-OH-DPAT bound non-specifically.

An IC$_{50}$ value was calculated according to the Hill analysis [see Hill A. V., J. Physiol., 40, 190-200 (1910)]. A h-5-HT$_{1A}$ binding inhibition constant (Ki) was calculated according to the equation:

$$h\text{-}5\text{-}HT_{1A}\text{ binding inhibition constant}(Ki)=IC_{50}/(1+S/Kd)$$

wherein S represents the concentration of [$^3$H]8-OH-DPAT added; and the Kd value represents the dissociation constant of [$^3$H]8-OH-DPAT, wherein the Kd value used was the value (1.28 nM) calculated by a saturation binding experiment separately conducted using the same cell membrane as above. A smaller value of the h-5-HT$_{1A}$ binding inhibition constant Ki means higher affinity for human serotonin 1A receptors.

The benzylpiperidine compounds of the present invention obtained in Examples were subjected to the tests of Test Examples 1 and 2. The results are shown in Table 6. These test results demonstrated that the benzylpiperidine compound of the present invention or the pharmaceutically acceptable salt thereof not only has a human serotonin reuptake inhibitory effect in combination with binding affinity for human 5-HT1A receptors but also has a high human serotonin reuptake inhibitory effect.

TABLE 6

| Compound (Example No.) | Test Example 1: h-SERT binding inhibition constant (Ki) [nM] | Test Example 2: h-5-HT$_{1A}$ binding inhibition constant (Ki) [nM] |
| --- | --- | --- |
| 1 | 0.87 | 4.5 |
| 2 | 0.70 | 12 |
| 4 | 0.79 | 4.2 |
| 6 | 1.2 | 72 |
| 7 | 2.7 | 4.6 |
| 8 | 2.8 | 3.7 |
| 9 | 3.1 | 13 |
| 10 | 4.2 | 19 |
| 11 | 6.4 | 3.8 |
| 12 | 9.2 | 23 |
| 13 | 7.4 | 8.6 |
| 14 | 8.5 | 55 |
| 15 | 3.2 | 35 |
| 16 | 2.9 | 27 |
| 17 | 4.0 | 30 |
| 18 | 6.2 | 295 |
| 19 | 3.0 | 29 |
| 20 | 2.4 | 57 |

Test Example 3

CYP2D6 Inhibition Screening Test 3-1 Materials

Bufuralol was purchased from Sigma-Aldrich Corp., and Pooled of Human Liver Microsomes was purchased from Xenotech, LLC.

3-2-1 Preparation of 0.5 M Potassium Phosphate Buffer (pH 7.4)

150 mL of a 0.5 M monopotassium phosphate solution and 700 mL of a 0.5 M dipotassium phosphate solution were mixed to adjust pH 7.4.

3-2-2 Preparation of 165 mM Magnesium Chloride Solution

Magnesium chloride hexahydrate was dissolved at a concentration of 3.35 g (MgCl$_2$.6H$_2$O)/100 mL in distilled water.

3-2-3 Preparation of Human Liver Microsome Solution

150 μL of Pooled Human Liver Microsomes (20 mg/ml), 12 mL of a 0.5 M potassium phosphate buffer, 1.2 mL of a 165 mM magnesium chloride solution, and 34.65 mL of distilled water were mixed.

3-2-4 Preparation of 13 mM β-NADPH Solution

β-NADPH was dissolved at a concentration of 11.75 mg/mL in distilled water.

3-2-5 Preparation of Substrate Solution

Bufuralol was dissolved at a concentration of 2.0 mM in DMSO and then diluted 200-fold with distilled water.

3-3 Experimental Procedures

1. A 10 mM DMSO solution of a test drug was serially diluted 5-fold with DMSO for 4 serial dilutions to prepare 10, 2, 0.4, and 0.08 mM DMSO solutions.

2. Each test drug solution of the step 1. and DMSO were separately diluted 96-fold with a human liver microsome solution, and each dilution was dispensed and 80 μL of each dilution to microplates.

3. 10 μL of a substrate solution and 10 μL of a β-NADPH solution were added to the well of the step 2., followed by incubation at 37° C. for 10 min.

4. The reaction was terminated by the addition of 300 μL of methanol.

5. The reaction mixture was filtered, and LC-MSMS analysis was conducted.

3-4 Quantification and Calculation

The amount of 1'-hydroxybufuralol produced was quantified by LC-MSMS, and this amount was used as a metabolic activity of CYP2D6 for each well. The remaining activity of each sample was determined by comparison with the activity obtained from DMSO as a test drug. An $IC_{50}$ value of CYP2D6 inhibition was determined from the test drug concentration and remaining activity. The $IC_{50}$ value was calculated by linear interpolation between two points that span the remaining activity 50%. A larger value of $IC_{50}$ of CYP2D6 inhibition means weaker CYP2D6 inhibition.

Test Example 4

Screening Test of the Rate of CYP2D6 Contribution in Human Liver Microsomal Metabolism 0.2 mL of a 50 mM potassium phosphate buffer solution (pH 7.4) containing NADPH (final concentration: 3 mM, manufactured by Oriental Yeast Co., Ltd.), 1 mg/mL human liver microsomes (manufactured by XENOTECH, LLC), and a 1 μM test substance was heated on a water bath at 37° C. for metabolic reaction. After the reaction for 15 minutes or 30 minutes, methanol was added in a volume 3 times that of the reaction solution, and the mixture was stirred to terminate the reaction. This reaction solution was centrifuged for protein precipitation. Then, the supernatant was collected and subjected to LC-MS/MS analysis. The results were analyzed as follows:

The test substance was quantified, and time-dependent change in the amount of the substance remaining was logarithmically plotted. A metabolic rate was calculated from the slope.

The ratio of the metabolic rate obtained by the addition of quinidine (final concentration: 4 μM) to the reaction solution to the metabolic rate obtained without the addition was used as the rate of contribution of enzymes other than CYP2D6, and the rate of contribution obtained by subtracting this rate of contribution of other enzymes from the total was used as the rate of CYP2D6 contribution. Specifically, it was calculated according to the equation:

Rate of contribution(%)={1−(metabolic rate [with quinidine]/metabolic rate[without quinidine])}× 100.

A smaller value of the rate of CYP2D6 contribution means smaller CYP2D6 contribution.

The benzylpiperidine compounds of the present invention obtained in Examples were subjected to the tests of Test Examples 3 and 4. The results are shown in Table 7. These test results demonstrated that the benzylpiperidine compound of the present invention or the pharmaceutically acceptable salt thereof has weaker CYP2D6 inhibition and undergoes small CYP2D6 contribution to metabolism.

TABLE 7

| Compound (Example No.) | Test Example 3: CYP2D6 Inhibition $IC_{50}$ [μM] | Test Example 4: Rate of CYP2D6 Contribution [%] |
|---|---|---|
| 1 | 27.9 | 36 |
| 2 | 12.8 | 12 |
| 4 | 22.9 | 0 |
| 6 | 24.7 | 4.2 |
| 7 | 17.5 | 54 |
| 8 | 31.0 | 9.6 |
| 9 | 33.7 | 7.8 |
| 10 | 21.5 | 49 |
| 11 | 24.6 | —*) |
| 12 | 27.9 | 17 |
| 13 | 26.9 | —*) |
| 14 | 34.8 | —*) |
| 15 | 36.1 | 11 |
| 16 | 26.3 | 9.2 |
| 17 | 24.6 | 14 |
| 18 | 27.5 | 0 |
| 19 | 20.4 | 16 |
| 20 | 23.4 | 24 |

*)The rate of CYP2D6 contribution was indeterminable in the present test due to high stability for human microsomal metabolism.

Test Example 5

Serotonin Transporter Function Inhibition Test Using [$^3$H]5-HT 1-1 Cells Used and Preparation of Cell Suspension CHO cells containing a human serotonin transporter (h-SERT) expressed therein (h-SERT/CHO) were used in the experiment. The cells were cultured in F12 containing 10% FCS, 500 μg/ml Geneticin, and 100 U/ml penicillin-100 μg/ml streptomycin (all manufactured by Sigma-Aldrich Corp.) in a 5% $CO_2$ incubator and dissociated/collected on the day of use using Cell Dissociation Buffer (Enzyme-free, PBS-based, manufactured by GIBCO). The collected cells were suspended in a buffer solution containing 0.1 mM $CaCl_2$ and 1 mM $MgCl_2$ in PBS (hereinafter, referred to as PBSCM) and stored in ice until use.

1-2 [$^3$H]5-HT Uptake Test

[$^3$H]5-HT uptake was measured according to the method of Roman et al. [Roman D. L. et al., J. Pharmacol. Exp. Ther., 308, 679-687 (2004); and Hill A. V., J. Physiol., 40, 190-200 (1910)]. Specifically, 149 μl of the cell suspension (10×10$^4$ cells/well) and 1 μl of a solution of a test drug dissolved in dimethyl sulfoxide were preincubated at 37° C. for 10 minutes. Then, 50 μl of [$^3$H]5-HT (final concentration: approximately 10 nM) diluted with PBSCM was added thereto to prepare 200 μl in total of a solution. This solution was reacted at 37° C. for 10 minutes and then rapidly filtered by suction at a low pressure through glass fiber filter paper coated with a 0.3% aqueous polyethyleneimine solution. The glass fiber filter paper was washed twice with 250 μl of an ice-cold saline and then transferred to a glass vial containing 4 ml of ACS-II (manufactured by Amersham Biosciences). Radioactivity remaining on the filter paper was measured using a liquid scintillation counter. The amount of [$^3$H]5-HT uptaken in the presence of 13.3 μM paroxetine was used as the amount of [$^3$H]5-HT uptaken non-specifically.

An IC$_{50}$ value was calculated according to the Hill analysis [see Hill A. V., J. Physiol., 40, 190-200 (1910)]. An uptake inhibition constant (Ki) was calculated according to the following equation:

Uptake inhibition constant$(Ki)$=IC$_{50}$/(1+S/Km)

wherein S represents the concentration of [$^3$H]5-HT added; and the Km value represents the Michaelis constant of [$^3$H] 5-HT, wherein the Km value used was the value (441 nM) calculated by a saturation experiment separately conducted using the same cell preparation as above. The results are shown in Table 8.

TABLE 8

| Compound (Example No.) | Test Example 5: h-SERT Function Inhibition Constant (Ki) [nM] |
|---|---|
| 1 | 8.9 |
| 2 | 1.6 |
| 4 | 4.2 |
| 6 | 1.6 |
| 7 | 16 |
| 10 | 44 |
| 13 | 51 |
| 17 | 18 |

The test results of Table 8 demonstrated that the benzylpiperidine compound of the present invention or the pharmaceutically acceptable salt thereof acts on serotonin transporters in serotonergic neurons and thereby strongly inhibit serotonin reuptake.

Test Example 6

X-Ray Powder Diffraction (XRPD) Analysis

An X-ray powder diffraction (XRPD) analyzer used was X'Pert Pro manufactured by Spectris Co., Ltd. The measurement was conducted under conditions involving a diffraction angle (2θ) in the range of 4° to 40°, Cu Kα1 radiation (wavelength: 1.54060 Å), an X-ray tube current of 40 mA, a voltage of 45 kV, a step of 0.01700°, and a measurement time of 101.41770 seconds/step. The measurement was conducted using approximately 5 mg of a sample in a non-reflective sample plate made of silicon single crystals (Si single crystals).

Each crystal obtained in Examples 27 to 32 was subjected to the present analysis. The obtained X-ray powder diffraction patterns are shown in FIGS. 1 to 6. Their crystal forms can be identified by determination from a diffraction peak characteristic of each crystal based on the diffraction pattern. The diffraction peak characteristic of each crystal identified from the diffraction pattern will be described later. In this context, a peak angle at the diffraction angle 2θ may have an error range to a certain degree depending on a measurement instrument or measurement conditions or the like. Specifically, a measurement error range of ±0.2, preferably ±0.1, is acceptable. On the other hand, the value of relative intensity may vary depending on the manner of sample preparation, measurement conditions, or the like.

Table 9 shows a peak angle, d-spacing, and relative intensity thereof in the X-ray powder diffraction of the Form 1-type crystal of 6-(2-{4-[4-bromo-3-(2-methoxyethoxy) benzyl]piperidin-1-yl}ethyl)-2,3-dihydro-4H-chromen-4-one hydrochloride of Example 27.

TABLE 9

| No. | Peak Angle (2θ) [°] | d-Spacing [Å] | Relative Intensity [%] |
|---|---|---|---|
| 1 | 4.3 | 20.4 | 6.1 |
| 2 | 8.7 | 10.2 | 4.6 |
| 3 | 10.8 | 8.2 | 5.1 |
| 4 | 12.6 | 7.0 | 86.9 |
| 5 | 13.0 | 6.8 | 38.1 |
| 6 | 14.0 | 6.3 | 13.8 |
| 7 | 16.0 | 5.5 | 92.4 |
| 8 | 16.3 | 5.4 | 48.0 |
| 9 | 16.6 | 5.4 | 34.9 |
| 10 | 17.1 | 5.2 | 13.2 |
| 11 | 19.3 | 4.6 | 13.4 |
| 12 | 19.7 | 4.5 | 44.1 |
| 13 | 20.2 | 4.4 | 77.1 |
| 14 | 21.7 | 4.1 | 19.3 |
| 15 | 23.4 | 3.8 | 100.0 |
| 16 | 24.3 | 3.7 | 71.1 |
| 17 | 24.9 | 3.6 | 41.2 |
| 18 | 26.5 | 3.4 | 31.7 |
| 19 | 27.3 | 3.3 | 15.7 |
| 20 | 28.3 | 3.2 | 12.5 |
| 21 | 30.6 | 2.9 | 7.8 |
| 22 | 32.3 | 2.8 | 19.2 |
| 23 | 33.0 | 2.7 | 14.1 |
| 24 | 34.2 | 2.6 | 7.9 |
| 25 | 36.8 | 2.4 | 4.2 |

Of the peaks shown in Table 9, the diffraction peak characteristic of the Form 1-type crystal of the present hydrochloride include peaks that give diffraction angles 2θ of 4.3°, 8.7°, 10.8°, 12.6°, 13.0°, 16.0°, 17.1°, 19.3°, 19.7°, and 20.2°.

Table 10 shows a peak angle, d-spacing, and relative intensity thereof in the X-ray powder diffraction of the Form A-type crystal of 6-(2-{4-[4-bromo-3-(2-methoxyethoxy) benzyl]piperidin-1-yl}ethyl)-2,3-dihydro-4H-chromen-4-one benzenesulfonate of Example 28.

TABLE 10

| No. | Peak Angle (2θ) [°] | d-Spacing [Å] | Relative Intensity [%] |
|---|---|---|---|
| 1 | 8.7 | 10.2 | 100.0 |
| 2 | 9.9 | 8.9 | 1.5 |
| 3 | 11.9 | 7.5 | 2.7 |
| 4 | 13.0 | 6.8 | 5.8 |
| 5 | 14.2 | 6.2 | 1.8 |
| 6 | 14.9 | 5.9 | 11.3 |
| 7 | 15.3 | 5.8 | 11.3 |
| 8 | 15.8 | 5.6 | 1.7 |
| 9 | 17.4 | 5.1 | 43.4 |
| 10 | 17.7 | 5.0 | 6.3 |
| 11 | 18.2 | 4.9 | 6.5 |
| 12 | 18.5 | 4.8 | 4.5 |
| 13 | 19.3 | 4.6 | 7.9 |
| 14 | 19.9 | 4.5 | 5.1 |
| 15 | 20.4 | 4.4 | 12.5 |
| 16 | 21.6 | 4.1 | 7.2 |
| 17 | 21.8 | 4.1 | 5.2 |
| 18 | 22.1 | 4.0 | 8.0 |

TABLE 10-continued

| No. | Peak Angle (2θ) [°] | d-Spacing [Å] | Relative Intensity [%] |
|---|---|---|---|
| 19 | 22.4 | 4.0 | 35.2 |
| 20 | 22.5 | 3.9 | 28.4 |
| 21 | 22.8 | 3.9 | 5.1 |
| 22 | 23.1 | 3.8 | 2.6 |
| 23 | 23.8 | 3.7 | 2.0 |
| 24 | 24.2 | 3.7 | 9.3 |
| 25 | 24.8 | 3.6 | 4.9 |
| 26 | 25.1 | 3.5 | 2.9 |
| 27 | 25.3 | 3.5 | 3.4 |
| 28 | 26.0 | 3.4 | 4.7 |
| 29 | 27.1 | 3.3 | 2.9 |
| 30 | 27.4 | 3.2 | 2.0 |
| 31 | 28.3 | 3.1 | 5.5 |
| 32 | 30.1 | 3.0 | 6.3 |
| 33 | 30.7 | 2.9 | 7.2 |
| 34 | 32.0 | 2.8 | 2.7 |
| 35 | 33.8 | 2.7 | 8.5 |
| 36 | 34.3 | 2.6 | 1.7 |
| 37 | 35.4 | 2.5 | 1.6 |
| 38 | 35.9 | 2.5 | 1.8 |
| 39 | 37.5 | 2.4 | 0.7 |
| 40 | 38.2 | 2.4 | 3.8 |
| 41 | 38.6 | 2.3 | 4.0 |
| 42 | 39.4 | 2.3 | 4.5 |
| 43 | 39.8 | 2.3 | 3.1 |
| 44 | 40.2 | 2.2 | 2.0 |
| 45 | 43.8 | 2.1 | 3.1 |
| 46 | 44.1 | 2.1 | 2.7 |
| 47 | 44.5 | 2.0 | 2.7 |
| 48 | 45.4 | 2.0 | 0.6 |
| 49 | 47.1 | 1.9 | 1.1 |
| 50 | 47.6 | 1.9 | 1.2 |
| 51 | 48.1 | 1.9 | 1.9 |
| 52 | 49.2 | 1.8 | 1.0 |
| 53 | 53.9 | 1.7 | 1.4 |

Of the peaks shown in Table 10, the diffraction peak characteristic of the Form A-type crystal of the present benzenesulfonate include peaks that give diffraction angles 2θ of 8.7°, 11.9°, 13.0°, 14.9°, 15.3°, 17.4°, 17.7°, 18.2°, 19.3°, and 20.4°.

Table 11 shows a peak angle, d-spacing, and relative intensity thereof in the X-ray powder diffraction of the Form B-type crystal of 6-(2-{4-[4-bromo-3-(2-methoxyethoxy)benzyl]piperidin-1-yl}ethyl)-2,3-dihydro-4H-chromen-4-one benzenesulfonate of Example 29.

TABLE 11

| No. | Peak Angle (2θ) [°] | d-Spacing [Å] | Relative Intensity [%] |
|---|---|---|---|
| 1 | 8.9 | 10.0 | 100.0 |
| 2 | 10.0 | 8.8 | 7.3 |
| 3 | 11.2 | 7.9 | 3.0 |
| 4 | 12.0 | 7.4 | 3.4 |
| 5 | 12.5 | 7.1 | 5.3 |
| 6 | 13.3 | 6.7 | 1.2 |
| 7 | 14.0 | 6.3 | 7.6 |
| 8 | 14.4 | 6.1 | 2.7 |
| 9 | 15.3 | 5.8 | 18.2 |
| 10 | 16.9 | 5.3 | 12.1 |
| 11 | 17.0 | 5.2 | 15.3 |
| 12 | 17.6 | 5.0 | 76.0 |
| 13 | 17.9 | 5.0 | 8.2 |
| 14 | 18.9 | 4.7 | 12.1 |
| 15 | 19.4 | 4.6 | 5.3 |
| 16 | 20.1 | 4.4 | 5.4 |
| 17 | 20.6 | 4.3 | 12.6 |
| 18 | 21.0 | 4.2 | 2.0 |
| 19 | 21.3 | 4.2 | 4.6 |

TABLE 11-continued

| No. | Peak Angle (2θ) [°] | d-Spacing [Å] | Relative Intensity [%] |
|---|---|---|---|
| 20 | 21.6 | 4.1 | 12.4 |
| 21 | 21.9 | 4.1 | 10.2 |
| 22 | 22.6 | 3.9 | 39.7 |
| 23 | 22.9 | 3.9 | 50.6 |
| 24 | 24.3 | 3.7 | 4.9 |
| 25 | 24.6 | 3.6 | 21.8 |
| 26 | 25.2 | 3.5 | 9.8 |
| 27 | 25.7 | 3.5 | 10.5 |
| 28 | 26.8 | 3.3 | 10.4 |
| 29 | 27.4 | 3.3 | 3.1 |
| 30 | 28.4 | 3.1 | 2.8 |
| 31 | 28.8 | 3.1 | 5.6 |
| 32 | 29.1 | 3.1 | 5.3 |
| 33 | 29.3 | 3.0 | 7.7 |
| 34 | 30.8 | 2.9 | 1.7 |
| 35 | 31.4 | 2.8 | 5.2 |
| 36 | 33.1 | 2.7 | 6.5 |
| 37 | 34.3 | 2.6 | 11.3 |
| 38 | 36.0 | 2.5 | 11.9 |
| 39 | 36.7 | 2.4 | 3.0 |
| 40 | 37.4 | 2.4 | 6.1 |
| 41 | 38.3 | 2.3 | 1.9 |
| 42 | 39.9 | 2.3 | 2.7 |
| 43 | 40.6 | 2.2 | 1.8 |
| 44 | 41.8 | 2.2 | 1.5 |
| 45 | 42.5 | 2.1 | 2.0 |
| 46 | 43.4 | 2.1 | 4.8 |
| 47 | 43.9 | 2.1 | 3.7 |
| 48 | 44.7 | 2.0 | 4.3 |
| 49 | 45.4 | 2.0 | 4.1 |
| 50 | 46.3 | 2.0 | 4.1 |
| 51 | 46.8 | 1.9 | 1.9 |
| 52 | 48.1 | 1.9 | 1.4 |
| 53 | 49.7 | 1.8 | 1.7 |
| 54 | 51.0 | 1.8 | 1.1 |
| 55 | 54.0 | 1.7 | 1.3 |
| 56 | 54.6 | 1.7 | 1.3 |
| 57 | 57.3 | 1.6 | 0.5 |
| 58 | 59.6 | 1.6 | 1.6 |

Of the peaks shown in Table 11, the diffraction peak characteristic of the Form B-type crystal of the present benzenesulfonate include peaks that give diffraction angles 2θ of 8.9°, 10.0°, 12.0°, 12.5°, 14.0°, 16.9°, 17.0°, 17.6°, 18.9°, and 20.6°.

Table 12 shows a peak angle, d-spacing, and relative intensity thereof in the X-ray powder diffraction of the Form C-type crystal of 6-(2-{4-[4-bromo-3-(2-methoxyethoxy)benzyl]piperidin-1-yl}ethyl)-2,3-dihydro-4H-chromen-4-one benzenesulfonate of Example 30.

TABLE 12-1

| No. | Peak Angle (2θ) [°] | d-Spacing [Å] | Relative Intensity [%] |
|---|---|---|---|
| 1 | 8.6 | 10.2 | 100.0 |
| 2 | 9.9 | 8.9 | 14.2 |
| 3 | 11.9 | 7.4 | 6.3 |
| 4 | 12.6 | 7.0 | 16.8 |
| 5 | 13.0 | 6.8 | 64.9 |
| 6 | 13.2 | 6.7 | 3.6 |
| 7 | 13.4 | 6.6 | 6.9 |
| 8 | 14.4 | 6.1 | 21.3 |
| 9 | 14.6 | 6.1 | 21.0 |
| 10 | 14.9 | 6.0 | 4.0 |
| 11 | 15.9 | 5.6 | 0.7 |
| 12 | 17.4 | 5.1 | 2.7 |
| 13 | 17.8 | 5.0 | 6.7 |
| 14 | 18.0 | 4.9 | 63.8 |
| 15 | 18.4 | 4.8 | 20.4 |

TABLE 12-1-continued

| No. | Peak Angle (2θ) [°] | d-Spacing [Å] | Relative Intensity [%] |
|---|---|---|---|
| 16 | 18.5 | 4.8 | 14.7 |
| 17 | 19.0 | 4.7 | 4.0 |
| 18 | 19.3 | 4.6 | 9.0 |
| 19 | 19.6 | 4.5 | 45.2 |
| 20 | 19.8 | 4.5 | 34.4 |
| 21 | 21.2 | 4.2 | 14.3 |
| 22 | 21.3 | 4.2 | 17.5 |
| 23 | 21.6 | 4.1 | 39.7 |
| 24 | 21.7 | 4.1 | 23.5 |
| 25 | 22.0 | 4.0 | 14.3 |
| 26 | 22.3 | 4.0 | 6.0 |
| 27 | 22.9 | 3.9 | 13.5 |
| 28 | 23.3 | 3.8 | 9.8 |
| 29 | 23.5 | 3.8 | 32.1 |
| 30 | 23.9 | 3.7 | 23.8 |
| 31 | 24.2 | 3.7 | 25.8 |
| 32 | 24.5 | 3.6 | 19.5 |
| 33 | 24.9 | 3.6 | 74.7 |
| 34 | 25.1 | 3.6 | 11.5 |
| 35 | 25.7 | 3.5 | 12.7 |
| 36 | 25.9 | 3.4 | 6.5 |
| 37 | 26.2 | 3.4 | 31.8 |
| 38 | 26.8 | 3.3 | 8.0 |
| 39 | 27.0 | 3.3 | 7.2 |
| 40 | 28.1 | 3.2 | 7.2 |
| 41 | 28.2 | 3.2 | 6.4 |
| 42 | 28.5 | 3.1 | 12.3 |
| 43 | 29.0 | 3.1 | 6.2 |
| 44 | 29.4 | 3.0 | 32.9 |
| 45 | 29.7 | 3.0 | 13.0 |
| 46 | 30.1 | 3.0 | 15.9 |
| 47 | 30.5 | 2.9 | 11.1 |
| 48 | 31.7 | 2.8 | 7.1 |
| 49 | 32.6 | 2.7 | 9.4 |
| 50 | 33.1 | 2.7 | 4.5 |
| 51 | 34.3 | 2.6 | 7.0 |
| 52 | 34.6 | 2.6 | 2.1 |
| 53 | 35.1 | 2.6 | 7.0 |
| 54 | 35.5 | 2.5 | 4.6 |
| 55 | 36.2 | 2.5 | 5.1 |
| 56 | 36.8 | 2.4 | 2.4 |
| 57 | 37.5 | 2.4 | 5.1 |
| 58 | 38.0 | 2.4 | 9.7 |
| 59 | 38.3 | 2.4 | 7.5 |
| 60 | 38.5 | 2.3 | 5.4 |
| 61 | 39.0 | 2.3 | 8.5 |
| 62 | 39.6 | 2.3 | 6.2 |
| 63 | 39.9 | 2.3 | 2.4 |
| 64 | 40.3 | 2.2 | 9.0 |
| 65 | 40.5 | 2.2 | 3.0 |
| 66 | 41.7 | 2.2 | 1.9 |
| 67 | 42.2 | 2.1 | 5.9 |
| 68 | 43.1 | 2.1 | 19.6 |
| 69 | 43.4 | 2.1 | 4.3 |
| 70 | 43.8 | 2.1 | 2.6 |
| 71 | 44.1 | 2.1 | 4.9 |
| 72 | 44.3 | 2.0 | 6.5 |
| 73 | 44.5 | 2.0 | 5.0 |
| 74 | 44.7 | 2.0 | 4.4 |
| 75 | 45.2 | 2.0 | 5.9 |
| 76 | 46.2 | 2.0 | 2.4 |
| 77 | 47.1 | 1.9 | 4.2 |
| 78 | 47.7 | 1.9 | 18.0 |
| 79 | 48.5 | 1.9 | 7.2 |
| 80 | 48.8 | 1.9 | 3.1 |
| 81 | 50.1 | 1.8 | 1.3 |
| 82 | 50.9 | 1.8 | 1.9 |
| 83 | 53.6 | 1.7 | 1.5 |
| 84 | 54.4 | 1.7 | 2.4 |
| 85 | 57.1 | 1.6 | 2.3 |
| 86 | 58.5 | 1.6 | 3.8 |
| 87 | 58.9 | 1.6 | 0.9 |
| 88 | 62.9 | 1.5 | 0.6 |
| 89 | 63.5 | 1.5 | 3.2 |

Of the peaks shown in Table 12, the diffraction peak characteristic of the Form C-type crystal of the present benzenesulfonate include peaks that give diffraction angles 2θ of 8.6°, 9.9°, 12.6°, 13.0°, 14.4°, 14.6°, 18.0°, 18.4°, 19.6°, and 19.8°.

Table 13 shows a peak angle, d-spacing, and relative intensity thereof in the X-ray powder diffraction of the Form A-type crystal of 6-(2-{4-[4-bromo-3-(2-methoxyethoxy)benzyl]piperidin-1-yl}ethyl)-2,3-dihydro-4H-chromen-4-one monofumarate of Example 31.

TABLE 13

| No. | Peak Angle (2θ) [°] | d-Spacing [Å] | Relative Intensity [%] |
|---|---|---|---|
| 1 | 7.6 | 11.6 | 26.5 |
| 2 | 10.0 | 8.9 | 53.6 |
| 3 | 11.5 | 7.7 | 30.4 |
| 4 | 11.8 | 7.5 | 52.5 |
| 5 | 12.8 | 6.9 | 15.8 |
| 6 | 13.4 | 6.6 | 32.4 |
| 7 | 13.7 | 6.5 | 51.5 |
| 8 | 14.1 | 6.3 | 17.1 |
| 9 | 14.6 | 6.0 | 29.2 |
| 10 | 15.3 | 5.8 | 35.3 |
| 11 | 16.0 | 5.5 | 24.1 |
| 12 | 16.8 | 5.3 | 46.3 |
| 13 | 17.1 | 5.2 | 28.5 |
| 14 | 17.4 | 5.1 | 53.7 |
| 15 | 18.3 | 4.8 | 89.4 |
| 16 | 19.4 | 4.6 | 67.9 |
| 17 | 19.6 | 4.5 | 69.4 |
| 18 | 20.2 | 4.4 | 40.7 |
| 19 | 20.9 | 4.3 | 75.3 |
| 20 | 21.3 | 4.2 | 43.4 |
| 21 | 22.0 | 4.0 | 40.8 |
| 22 | 22.6 | 3.9 | 71.1 |
| 23 | 23.2 | 3.8 | 100.0 |
| 24 | 23.8 | 3.7 | 26.4 |
| 25 | 24.9 | 3.6 | 62.8 |
| 26 | 25.2 | 3.5 | 37.0 |
| 27 | 25.7 | 3.5 | 98.0 |
| 28 | 26.5 | 3.4 | 16.5 |
| 29 | 28.2 | 3.2 | 18.4 |
| 30 | 30.3 | 2.9 | 17.9 |
| 31 | 34.1 | 2.6 | 7.9 |

Of the peaks shown in Table 13, the diffraction peak characteristic of the Form A-type crystal of the present fumarate include peaks that give diffraction angles 2θ of 7.6°, 10.0°, 11.5°, 11.8°, 14.6°, 15.3°, 16.0°, 17.4°, 18.3°, 19.6°, 20.9°, 22.0°, and 23.2°.

Table 14 shows a peak angle, d-spacing, and relative intensity thereof in the X-ray powder diffraction of the Form A+-type crystal of 6-(2-{4-[(4-bromo-3-(2-methoxyethoxy)benzyl]piperidin-1-yl}ethyl)-2,3-dihydro-4H-chromen-4-one monofumarate of Example 32.

TABLE 14

| No. | Peak Angle (2θ) [°] | d-Spacing [Å] | Relative Intensity [%] |
|---|---|---|---|
| 1 | 7.4 | 12.0 | 1.4 |
| 2 | 10.1 | 8.8 | 2.4 |
| 3 | 11.1 | 8.0 | 5.9 |
| 4 | 12.8 | 6.9 | 2.4 |
| 5 | 13.8 | 6.4 | 1.0 |
| 6 | 14.7 | 6.0 | 17.1 |
| 7 | 16.0 | 5.5 | 5.6 |
| 8 | 17.1 | 5.2 | 1.1 |
| 9 | 17.6 | 5.0 | 1.8 |
| 10 | 18.4 | 4.8 | 84.7 |
| 11 | 19.5 | 4.6 | 7.1 |

TABLE 14-continued

| No. | Peak Angle (2θ) [°] | d-Spacing [Å] | Relative Intensity [%] |
|---|---|---|---|
| 12 | 19.8 | 4.5 | 11.1 |
| 13 | 21.2 | 4.2 | 1.5 |
| 14 | 22.2 | 4.0 | 23.0 |
| 15 | 23.4 | 3.8 | 8.0 |
| 16 | 25.1 | 3.5 | 3.5 |
| 17 | 25.9 | 3.4 | 100.0 |
| 18 | 26.7 | 3.3 | 7.5 |
| 19 | 28.7 | 3.1 | 1.6 |
| 20 | 29.7 | 3.0 | 2.7 |
| 21 | 30.3 | 2.9 | 7.2 |
| 22 | 33.0 | 2.7 | 1.2 |
| 23 | 33.5 | 2.7 | 6.4 |
| 24 | 34.4 | 2.6 | 2.5 |
| 25 | 35.9 | 2.5 | 1.3 |
| 26 | 38.2 | 2.4 | 2.2 |
| 27 | 39.5 | 2.3 | 1.6 |
| 28 | 43.2 | 2.1 | 4.0 |
| 29 | 49.3 | 1.8 | 3.7 |
| 30 | 53.3 | 1.7 | 4.4 |

Of the peaks shown in Table 14, the diffraction peak characteristic of the Form A+-type crystal of the present fumarate include peaks that give diffraction angles 2θ of 7.4°, 10.1°, 11.1°, 14.7°, 16.0°, 18.4°, 19.8°, 22.2°, 23.4°, 25.9°, and 26.7°.

Preparation Example 1

Production of Tablets 6-(2-{4-[4-Bromo-3-(2-methoxyethoxy)benzyl]piperidin-1-yl}ethyl)-2,3-dihydro-1H-inden-1-one (5 g), lactose (80 g), corn starch (30 g), crystalline cellulose (25 g), hydroxypropylcellulose (3 g), light anhydrous silicic acid (0.7 g), and magnesium stearate (1.3 g) are mixed and granulated by a standard method and compressed into 1000 tablets of 145 mg each.

Preparation Example 2

Production of Powders 6-(2-{4-[4-Bromo-3-(2-methoxyethoxy)benzyl]piperidin-1-yl}ethyl)-2,3-dihydro-4H-chromen-4-one benzenesulfonate (10 g), lactose (960 g), hydroxypropylcellulose (25 g), and light anhydrous silicic acid (5 g) are mixed by a standard method and then prepared into powders.

INDUSTRIAL APPLICABILITY

A benzylpiperidine compound of the present invention represented by the formula (1) and a pharmaceutically acceptable salt thereof are characterized in terms of a chemical structure by having a di-substituted benzyl group having a 2-methoxyethoxy or 2-hydroxyethoxy group at 3-position of the benzene ring moiety and having, at 1-position of piperidine, a phenylethyl group of which the benzene ring moiety fused with a saturated ring comprising an oxo group. The benzylpiperidine compound of the present invention or the pharmaceutically acceptable salt thereof is a novel serotonin reuptake inhibitor that has an improved human serotonin reuptake inhibitory effect in combination with affinity for human serotonin 1A receptors, has a weaker inhibitory effect on CYP2D6, one of the molecular species of human cytochrome P450, and undergoes small CYP2D6 contribution to drug metabolism in humans. Therefore, it can be used as, for example, a highly safe therapeutic or preventive drug excellent in therapeutic effect on diseases such as depression and anxiety (anxiety disorder).

Figure 1:
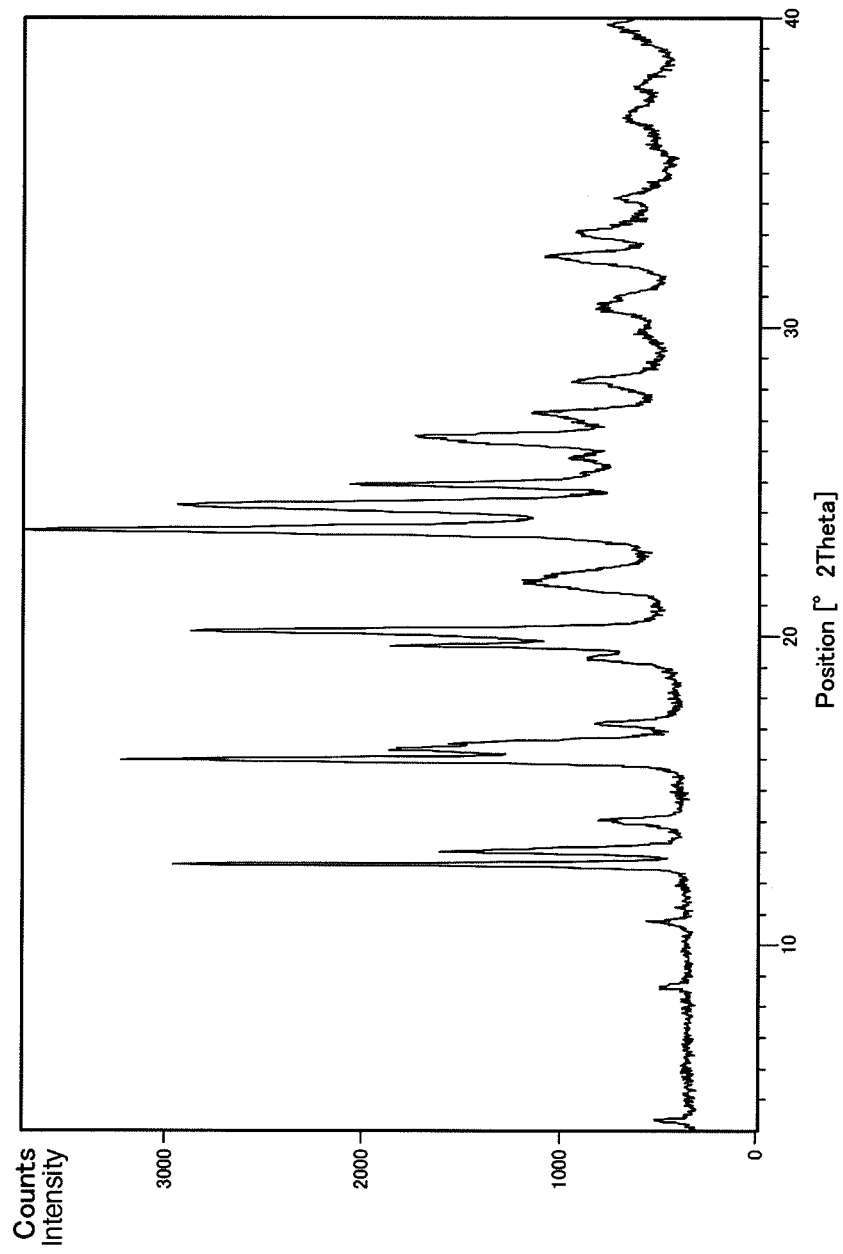
FIG. 1 is an X-ray powder diffraction pattern of a Form 1-type crystal of 6-(2-{4-[4-Bromo-3-(2-methoxyethoxy)benzyl]piperidin-1-yl}ethyl)-2,3-dihydro-4H-chromen-4-one hydrochloride of Example 27 obtained in X-ray powder diffraction analysis of Test Example 6.
Figure 2:
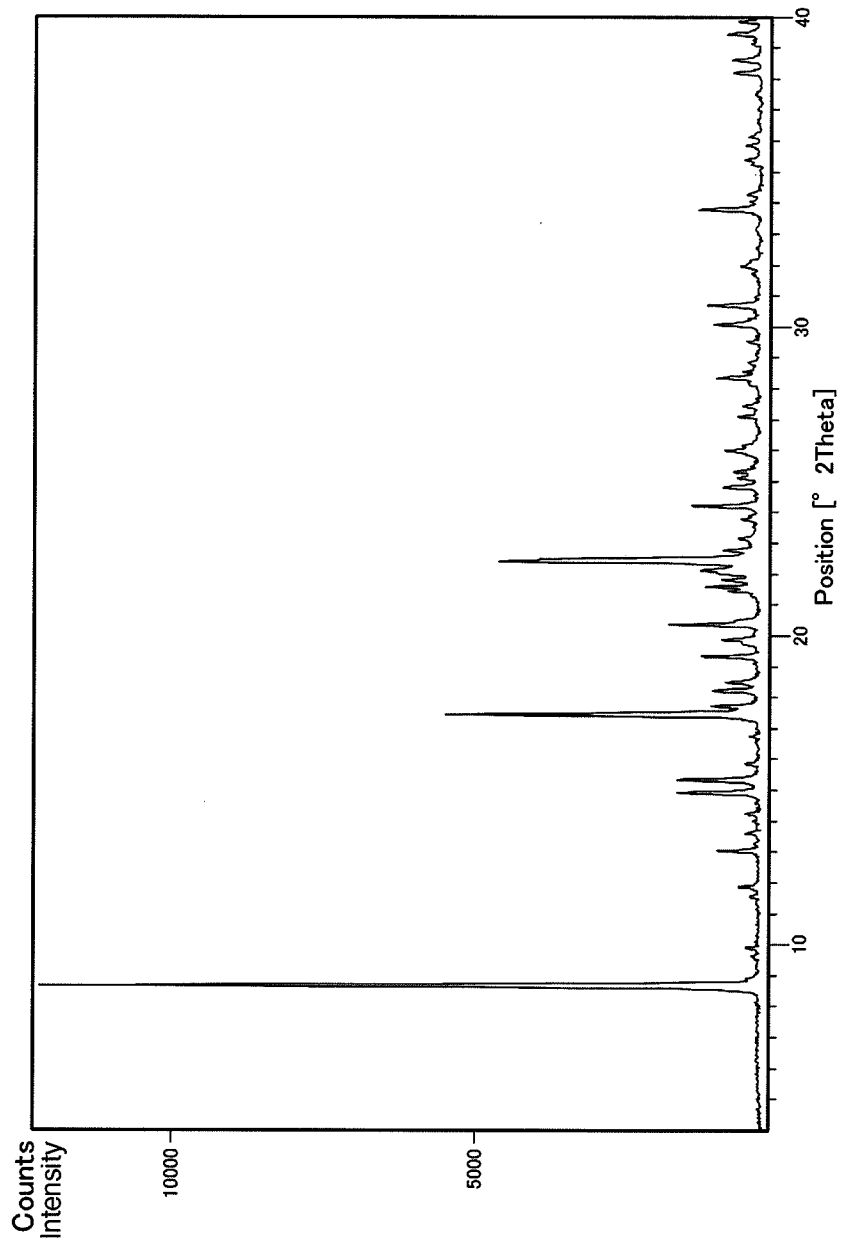
FIG. 2 is an X-ray powder diffraction pattern of a Form A-type crystal of 6-(2-{4-[4-Bromo-3-(2-methoxyethoxy)benzyl]piperidin-1-yl}ethyl)-2,3-dihydro-4H-chromen-4-one benzenesulfonate of Example 28 obtained in X-ray powder diffraction analysis of Test Example 6.
Figure 3:
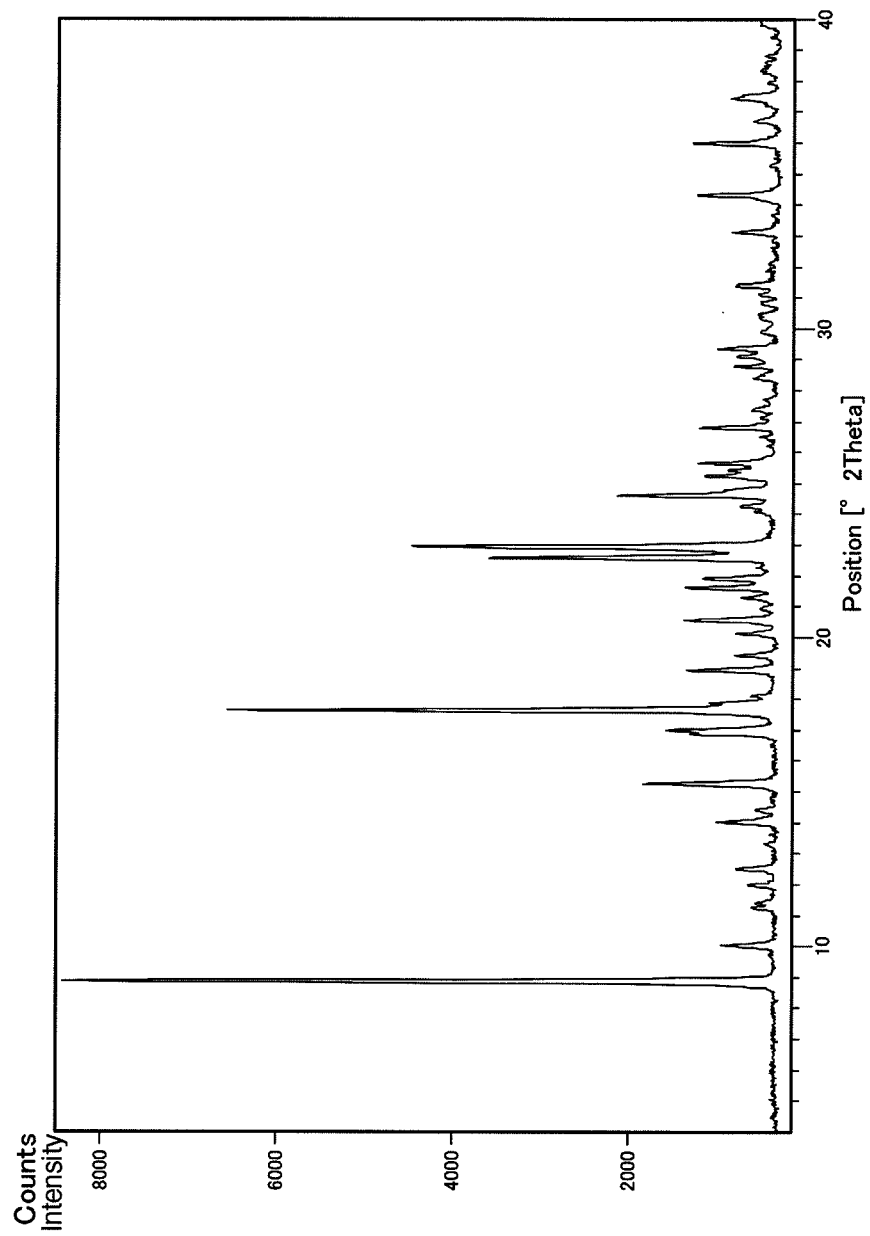
FIG. 3 is an X-ray powder diffraction pattern of a Form B-type crystal of 6-(2-{4-[4-Bromo-3-(2-methoxyethoxy)benzyl]piperidin-1-yl}ethyl)-2,3-dihydro-4H-chromen-4-one benzenesulfonate of Example 29 obtained in X-ray powder diffraction analysis of Test Example 6.
Figure 4:
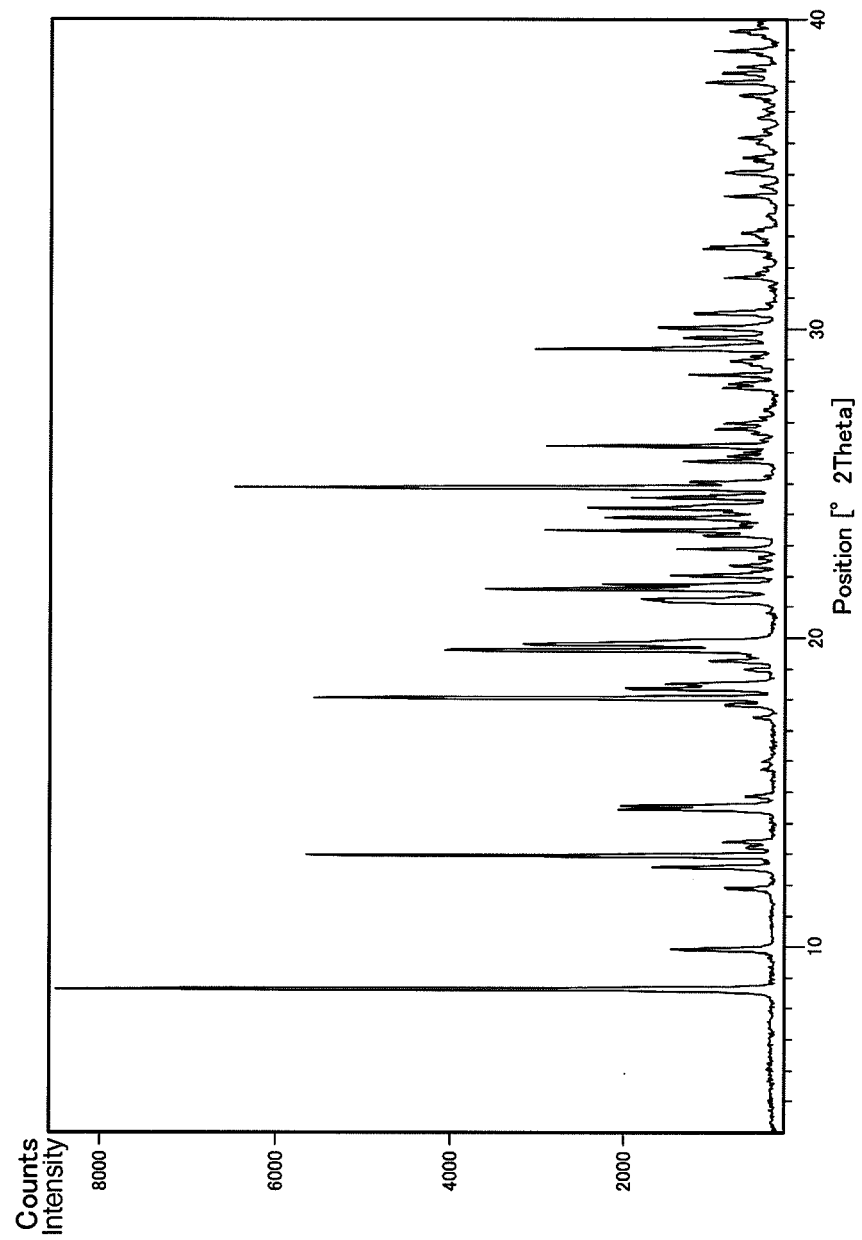
FIG. 4 is an X-ray powder diffraction pattern of a Form C-type crystal of 6-(2-{4-[4-Bromo-3-(2-methoxyethoxy)benzyl]piperidin-1-yl}ethyl)-2,3-dihydro-4H-chromen-4-one benzenesulfonate of Example 30 obtained in X-ray powder diffraction analysis of Test Example 6.
Figure 5:
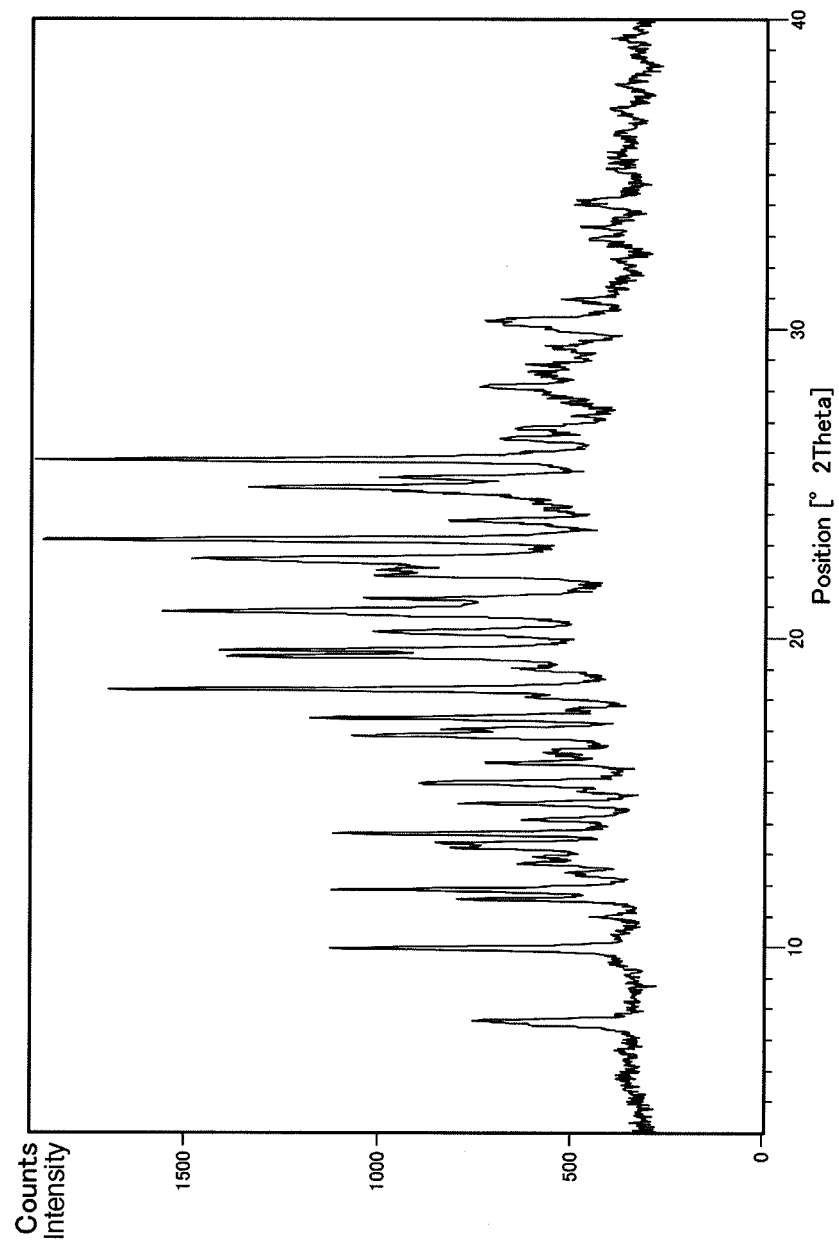
FIG. 5 is an X-ray powder diffraction pattern of a Form A-type crystal of 6-(2-{4-[4-Bromo-3-(2-methoxyethoxy)benzyl]piperidin-1-yl}ethyl)-2,3-dihydro-4H-chromen-4-one monofumarate of Example 31 obtained in X-ray powder diffraction analysis of Test Example 6.
Figure 6:
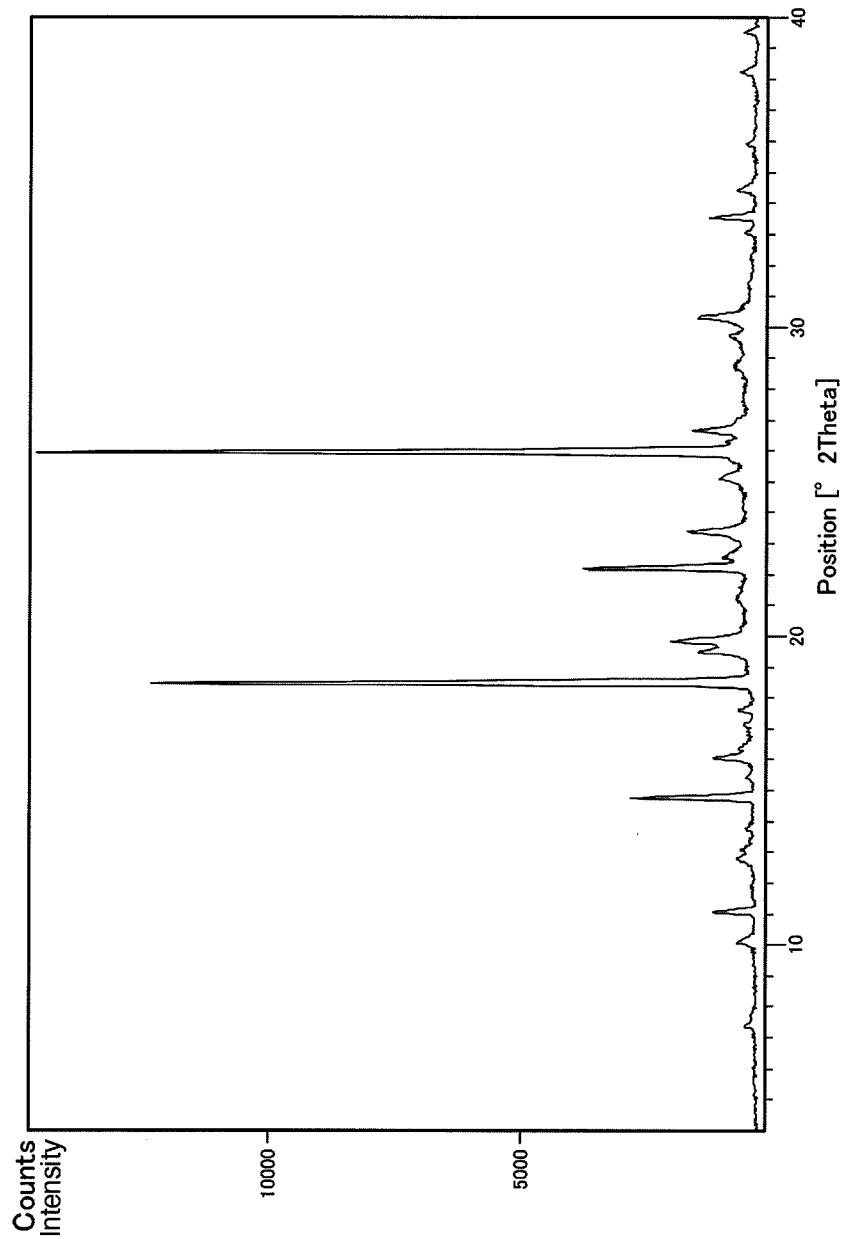
FIG. 6 is an X-ray powder diffraction pattern of a Form A+-type crystal of 6-(2-{4-[4-Bromo-3-(2-methoxyethoxy)benzyl]piperidin-1-yl}ethyl)-2,3-dihydro-4H-chromen-4-one monofumarate of Example 32 obtained in X-ray powder diffraction analysis of Test Example 6.

The invention claimed is:

1. A compound represented by the formula (11) or a pharmaceutically acceptable salt thereof:

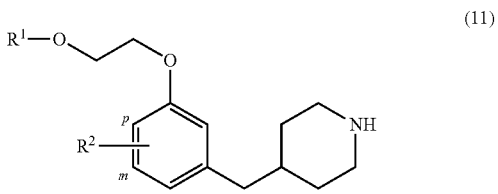

(11)

wherein $R^1$ represents a hydrogen atom or a methyl group; and $R^2$ represents a group bonded at a p- or m-position in relation to a methylene group bonded to the piperidine ring, specifically, a chlorine atom bonded at the p-position, a bromine atom bonded at the p-position, a methyl group bonded at the p-position, a chlorine atom bonded at the m-position, or a bromine atom bonded at the m-position.

2. The compound according to claim 1 or a pharmaceutically acceptable salt thereof, wherein the compound represented by the formula (11) is selected from the group consisting of the following compounds:
4-[3-Bromo-5-(2-methoxyethoxy)benzyl]piperidine,
4-[3-Chloro-5-(2-methoxyethoxy)benzyl]piperidine,
4-[4-Bromo-3-(2-methoxyethoxy)benzyl]piperidine,
4-[4-Chloro-3-(2-methoxyethoxy)benzyl]piperidine, (2-[2-Bromo-5-(piperidin-4-ylmethyl)phenoxy]-ethanol, and 4-[3-(2-Methoxyethoxy)-4-methylbenzyl]piperidine.

3. The compound according to claim 1 or a pharmaceutically acceptable salt thereof, wherein the compound represented by the formula (11) is selected from the group consisting of the following compounds:

4-[4-Bromo-3-(2-methoxyethoxy)benzyl]piperidine, and
(2-[2-Bromo-5-(piperidin-4-ylmethyl)phenoxy] ethanol.

* * * * *